US007612089B2

(12) United States Patent
Song et al.

(10) Patent No.: US 7,612,089 B2
(45) Date of Patent: Nov. 3, 2009

(54) TETRAHYDROISOQUINOLINES AS FACTOR XA INHIBITORS

(75) Inventors: Yonghong Song, Foster City, CA (US); Bing-Yan Zhu, Palo Alto, CA (US); Shumei Wang, Foster, CA (US); Shawn Bauer, Pacifica, CA (US); Robert M. Scarborough, Half Moon Bay, CA (US)

(73) Assignee: Portola Pharmaceuticals, Inc., So. San Francisco, CA (US)

( * ) Notice: Subject to any disclaimer, the term of this patent is extended or adjusted under 35 U.S.C. 154(b) by 316 days.

(21) Appl. No.: 11/284,805

(22) Filed: Nov. 21, 2005

(65) Prior Publication Data

US 2006/0160840 A1 Jul. 20, 2006

Related U.S. Application Data

(60) Provisional application No. 60/629,836, filed on Nov. 19, 2004.

(51) Int. Cl.
*C07D 498/02* (2006.01)
*C07D 217/12* (2006.01)
*C07D 217/02* (2006.01)
*C07D 209/42* (2006.01)
*A61K 31/4743* (2006.01)
*A61K 31/47* (2006.01)
*A61K 31/405* (2006.01)

(52) U.S. Cl. .................. 514/301; 514/310; 514/419; 546/114; 546/146; 548/492

(58) Field of Classification Search ................ 546/146, 546/114; 514/304, 301, 310, 419; 548/492
See application file for complete search history.

(56) References Cited

U.S. PATENT DOCUMENTS

| 4,588,587 A | 5/1986 | Gasic |
| 5,246,943 A * | 9/1993 | Blankley et al. ............ 514/307 |
| 2004/0038858 A1 | 2/2004 | Dorsch et al. |
| 2005/0137230 A1 | 6/2005 | Dorsch et al. |

FOREIGN PATENT DOCUMENTS

| EP | 0798295 | 10/1997 |
| WO | WO 94/13693 | 6/1994 |
| WO | WO 98/28269 | 7/1998 |
| WO | WO 99/10316 | 3/1999 |
| WO | 01/70684 * | 9/2001 |
| WO | WO 01/70684 A2 | 9/2001 |
| WO | WO 97/21437 | 4/2002 |
| WO | WO 02/48099 | 6/2002 |

OTHER PUBLICATIONS

Charton et al., Tetrahedron Letters, 2001, vol. 42, pp. 7559-7561.*
Kazmierski et al., Journal of Organic Chemistry (1994), 59(7), 1789-95.*

Berge et al., "Pharmaceutical Salts," *Journal of Pharmaceutical Sciences*, Jan. 1977, vol. 66, No. 1, pp. 1-19.

Claeson, "Synthetic Peptides and Peptidomimetics as Substrates and Inhibitors of Thrombin and other Proteases in the Blood Coagulation System", *Blood Coagulation and Fibrinolyisis*, 1994, vol. 5, pp. 411-436.

Elödi et al., "Optimization of Conditions for the Catalytic Effect of the Factor IXa-Factor VIII Complex: Probable Role of the Complex in the Amplification of Blood Coagulation", *Thrombosis Research*, 1979, vol. 15, pp. 617-629.

Fressinaud et al., "Therapeutic monitoring of Von Willebrand Disease: Interest and Limits of a Platelet Function Analyser at High Shear Rates", *British Journal of Haematology*, 1999, vol. 106, No. 3, pp. 777-783.

Hauptmann et al., "Comparison of the Anticoagulant and Antithrombotic Effects of Synthetic Thrombin and Factor Xa Inhibitors", *Thrombosis and Haemostasis*, 1990, vol. 63, pp. 220-223.

Hitomi et al., "Inhibitory Effect of New Synthetic Protease Inhibitor (fut-175) on the Coagulation System", *Haemostasis*, 1985, vol. 15, pp. 164-168.

Kam et al., "Mechanism Based Isocoumarin Inhibitors for Trypsin and Blood Coagulation Serine Proteases: New Anticoagulants", *Biochemistry*, 1988, vol. 27, pp. 2547-2557.

Maugeri, et al., "Transcellular Metabolism of Arachidonic Acid: Increased Platelet Thromboxane Generation in the Presence of Activated Polymorphonuclear Leukocytes", *Blood*, 1992, vol. 80, No. 2, pp. 447-451.

Nutt et al., "The Amino Acid sequence of Antistasin, a Potent Inhibitor of Factor Xa Reveals a Repeated Internal Structure", *Journal Biological Chemistry*, 1988, vol. 263, No. 21, pp. 10162-10167.

Rocca et al., "Cyclooxygenase-2 Expression is Induced During Human Megakaryopoiesis and Characterizes Newly Formed Platelets", *Proceedings of National Academy of Sciences*, 2002, vol. 99, No. 11, pp. 7634-7639.

Sturzebecher et al., "Synthetic Inhibitors of Bovine Factor Xa and Thrombin. Comparison of Their Anticoagulant Efficiency", *Thrombosis Research*, 1989, vol. 54, pp. 245-252.

Tidwell et al., "Strategies for Anticoagulation With Synthetic Protease Inhibitors. Xa Inhibitors Versus Thrombin Inhibitors", *Thrombosis Research*, 1980, vol. 19, pp. 339-349.

(Continued)

*Primary Examiner*—D. Margaret Seaman
*Assistant Examiner*—Niloofar Rahmani
(74) *Attorney, Agent, or Firm*—Townsend and Townsend and Crew LLP

(57) ABSTRACT

The present invention is directed to compounds represented by Formula I and pharmaceutically acceptable salts, solvates, hydrates, and prodrugs thereof which are inhibitors of Factor Xa. The present invention is also directed to and intermediates used in making such compounds, pharmaceutical compositions containing such compounds, methods to prevent or treat a number of conditions characterized by undesired thrombosis and methods of inhibiting the coagulation of a blood sample.

16 Claims, No Drawings

OTHER PUBLICATIONS

Turner et al., "*p*-Amidino Esters as Irreversible Inhibitors of Factor IXa and Xa and Thrombin", *Biochemistry*, 1986; vol. 25, pp. 4929-4935.

Valles et al., "Erythrocytes Metabolically Enhance Collagen-Induced Platelet Responsiveness Via Increased Thromboxane Production, Adenosine Diphosphate Release, and Recruitment", *Blood*, 1991, vol. 78, No. 1, pp. 154-162.

Wang et al., "Immunological Characterization of Urinary 8-epi-Prostaglandin F2 Alpha Excretion in Man", *Journal of Pharmacology and Experimental Therapeutics*, 1995, vol. 275, No. 1, pp. 94-100.

Wang et al., "Incidence of Aspirin Nonresponsiveness Using the Ultegra Rapid Platelet Function Assay-ASA", *American Journal of Cardioliology*, 2003, vol. 92, No. 12, pp. 1492-1494.

Waxman et al., "Tick Anticoagulant peptide (TAP) is a Novel Inhibitor of Blood Coagulation Factor Xa", *Science*, 1990; vol. 248, pp. 593-596.

Yin et al., "Antiaggregatory Activity of 8-Epi-Prostaglandin F2 Alpha and Other F-Series Prostanoids and Their Binding to Thromboxane A2/Prostaglandin H2 Receptors in Human Platelets", *The Journal of Pharmacology and Experimental Therapeutics*. 1994, vol. 270, No. 3, pp. 1192-1196.

\* cited by examiner

TETRAHYDROISOQUINOLINES AS FACTOR XA INHIBITORS

CROSS-REFERENCES TO RELATED APPLICATIONS

This application claims the benefit of U.S. Patent Application No. 60/629,836, filed Nov. 19, 2004, the content of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", *Blood Coag. Fibrinol.*, 5:411-436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., *Thromb. Res.* 15:617-619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", *J. Biol. Chem.*, 263:10162-10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa", *Science*, 248:593-596 (1990).

Factor Xa inhibitory compounds which are not large polypeptide-type inhibitors have also been reported (see e.g. Tidwell, R. R. et al., "Strategies for Anticoagulation With Synthetic Protease Inhibitors. Xa Inhibitors Versus Thrombin Inhibitors", *Thromb. Res.*, 19:339-349 (1980); Turner, A. D. et al., "p-Amidino Esters as Irreversible Inhibitors of Factor IXa and Xa and Thrombin", *Biochemistry*, 25:4929-4935 (1986); Hitomi, Y. et al., "Inhibitory Effect of New Synthetic Protease Inhibitor (FUT-175) on the Coagulation System", *Haemostasis*, 15:164-168 (1985); Sturzebecher, J. et al., "Synthetic Inhibitors of Bovine Factor Xa and Thrombin. Comparison of Their Anticoagulant Efficiency", *Thromb. Res.*, 54:245-252 (1989); Kam, C. M. et al., "Mechanism Based Isocoumarin Inhibitors for Trypsin and Blood Coagulation Serine Proteases: New Anticoagulants", *Biochemistry*, 27:2547-2557 (1988); Hauptmann, J. et al., "Comparison of the Anticoagulant and Antithrombotic Effects of Synthetic Thrombin and Factor Xa Inhibitors", *Thromb. Haemost.*, 63:220-223 (1990)).

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal $C(=NH)—NH_2$ group; WO 97/21437 describes benzimidazole compounds substituted by a basic radical which are connected to a naphthyl group via a straight or branched chain alkylene, CO or $SO_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

BRIEF SUMMARY OF THE INVENTION

The present invention provides in one aspect, compounds having the formula:

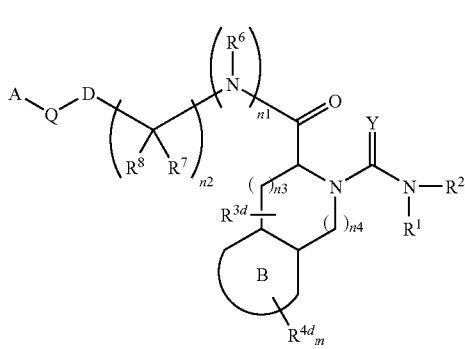

(I)

and pharmaceutically acceptable salts, hydrates, solvates and prodrugs thereof. In formula (I), the letter Y represents O or S and the ring B represents a 5-7 membered aryl or heteroaryl comprising 1 to 3 heteroatoms selected from the group consisting of N, O, and S, each aryl or heteroaryl optionally substituted with 1 to 3 $R^{4d}$ substituents.

The symbol $R^1$ represents a member selected from the group consisting of: hydrogen, —$C_{1-6}$alkyl, —$C_{0-6}$alkyl-aryl, heteroaryl and —$C_{2-6}$alkenyl. The symbol $R^2$ represents a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The letter D represents a member selected from the group consisting of: a direct bond, aryl, heteroaryl, $C_{3-8}$cycloalkyl, $C_{3-8}$cycloalkylene, heteromonocyclyl, unfused heterobicyclyl, and fused heterobicyclyl; each of which is optionally substituted with 1 to 3 $R^9$ substituents, wherein each heterocyclyl comprises from 5 to 10 ring atoms, 1-4 of which are selected from the group consisting of N, O and S.

The symbol Q is selected from the group consisting of: a direct bond, —$C(R^{10a}R^{10b})$—, —$C(O)$—, —$C(S)$—, $C(=NR^{10a})$—, —O—, —$N(R^{10a})$—, —$N(R^{10a})CH_2$—, —$CH_2N(R^{10a})$—, —$C(O)N(R^{10a})$—, —$N(R^{10a})C(O)$—, —$SO_2$—, —SO—, —$SO_2N(R^{10a})$—, and —$N(R^{10a})$—$SO_2$—; and at least one of D and Q is not a direct bond.

The symbol A is selected from the group consisting of: —$NR^{11c}R^{11d}$, —$C(=NR^{11c})NR^{11a}R^{11b}$, —$C(=NR^{11e}R^{11f})NR^{11a}R^{11b}$, —$N(R^{11d})C(=NR^{11c})NR^{11a}R^{11b}$, —$N(R^{11d})C(=NR^{11c})R^{11a}$, —$N(R^{11c})NR^{11a}R^{11b}$, —$N(R^{11c})OR^{11d}$; $C_{1-6}$alkyl, $C_{2-6}$alkenyl, aryl, heteroaryl, —$C_{3-8}$cycloalkyl, —$C_{3-6}$cycloalkenyl, heteromonocyclyl, and fused heterobicyclyl; each of aryl, heteroaryl, heteromonocyclyl and fused heterobicyclyl, optionally substituted with 1 to 3 $R^{11g}$; wherein each hetercyclyl comprises 5 to 10 ring atoms, 1-4 of which are selected from the group consisting of N, O and S; wherein each hetercyclyl comprises from 5 to 10 ring atoms, 1-4 of which are selected from the group consisting of N, O and S. Each $R^{2a}$, $R^{3d}$, $R^{4d}$, $R^9$ and $R^{11g}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, $C_{0-2}$alkyl-$SR^{12a}$, —O—$CH_2$—$CH_2$—$OR^{12a}$, —O—$CH_2$—$CO_2R^{12a}$, —$N(R^{12a})$—$CH_2$—$CH_2$—$OR^{12b}$, —$C_{0-2}$alkyl-C(O)$NR^{12a}R^{12b}$, —$C_{0-2}$alkyl-$CO_2R^{12a}$, —$(CH_2)_mN(R^{12a})$—C(O)$R^{12b}$, —$C_{0-2}$alkyl-$N(R^{12c})$—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-$N(R^{12d})$C(=$NR^{12c}$)$NR^{12a}R^{12b}$, —$C_{0-2}$alkyl-$N(R^{12a})$—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CONR^{12a}R^{12b}$, =O, =S, —OH, —CN and —$NO_2$; wherein each heteroaryl or heterocyclyl comprises 1 to 4 heteroatoms, independently selected from the group consisting of N, O and S. Each of the symbols $R^{11a}$, $R^{11b}$, $R^{11c}$, $R^{11d}$, $R^{11e}$, $R^{11f}$, $R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$SO_2$—$C_{1-4}$alkyl, —$C_{0-6}$alkyl-$SO_2$—$N(C_{1-4}$alkyl, $C_{1-4}$alkyl), —$C_{0-6}$alkyl-$N(C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$. Each of the symbols $R^6$, $R^7$, $R^8$, $R^{10a}$ and $R^{10b}$ is a member independently selected from the group consisting of: hydrogen, $C_{1-6}$alkyl, $C_{2-6}$alkenyl, $C_{2-6}$alkynyl and $C_{0-4}$alkyl$C_{3-8}$cycloalkyl, —$C_{0-6}$alkyl-aryl and —$C_{0-6}$alkyl-heteraryl.

Each subscript n1 and n2 represents an integer of 0 to 1; and each subscript n3 and n4 represents an integer of 0 to 2.

The present invention further provides chemical intermediates, pharmaceutical compositions and methods for preventing or treating a condition in a mammal characterized by undesired thrombosis comprising the step of administering to said mammal a therapeutically effective amount of a compound of the present invention. Such conditions include but are not limited to acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

The present invention further provides methods for inhibiting the coagulation of a blood sample comprising contacting said sample with a compound of the present invention.

BRIEF DESCRIPTION OF THE DRAWINGS

Not applicable

DETAILED DESCRIPTION OF THE INVENTION

Abbreviations and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-8}$cycloalkyl) and being fully saturated or having no more than one double bond between ring vertices. When "cycloalkyl" is used in combination with "alkyl", as in $C_{3-8}$cycloalkyl-alkyl, the cycloalkyl portion is meant to have from three to five carbon atoms, while the alkyl portion is an alkylene moiety having from one to three carbon atoms (e.g., —$CH_2$—, —$CH_2CH_2$— or —$CH_2CH_2CH_2$—).

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups (typically provided as —$NR^aR^b$ or a variant thereof), the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. If not specifically stated, substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The terms "heterocycle" and "heterocyclyl" refers to a saturated or unsaturated non-aromatic cyclic group containing at least one sulfur, nitrogen or oxygen heteroatom. Each heterocycle can be attached at any available ring carbon or heteroatom. Each heterocycle may have one ("heteromonocyclyl") or more rings (e.g. "heterobicyclyl"). When multiple rings are present, they can be fused together or linked covalently. Each heterocycle must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Non-limiting examples of heterocycle groups include pyrrolidine, piperidine, imidazolidine, pyrazolidine, butyrolactam, valerolactam, imidazolidinone, hydantoin, dioxolane, phthalimide, 1,4-dioxane, morpholine, thiomorpholine, thiomorpholine-S,S-dioxide, piperazine, pyran, pyridone, 3-pyrroline, thiopyran, pyrone, tetrahydrofuran, tetrahydrothiophene and the like.

The above terms (e.g., "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below.

Substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=N—H, —NR'C($NH_2$)=NH, —NH—C($NH_2$)=NR', —S(O)R', —$SO_2$R', —$SO_2$NR'R", —NR'$SO_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R'" is independently selected from hydrogen, $C_{1-6}$alkyl, $C_{3-8}$cycloalkyl, $C_{2-6}$alkenyl, $C_{2-6}$alkynyl, unsubstituted aryl and heteroaryl, (unsubstituted aryl)-$C_{1-4}$alkyl, and unsubstituted aryloxy-$C_{1-4}$alkyl. Other suitable substituents include each of the above aryl substituents attached to a ring atom by an alkylene tether of from 1-4 carbon atoms.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

EMBODIMENTS OF THE INVENTION

Compounds

In one aspect, the present invention provides compounds having the formula:

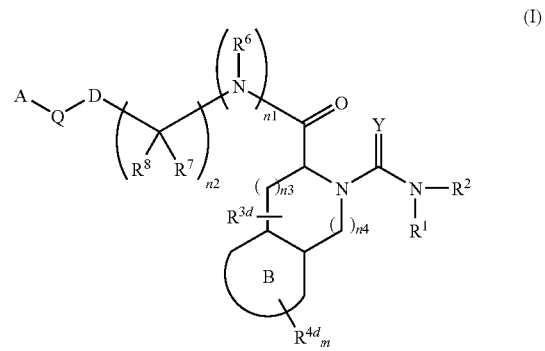

(I)

and pharmaceutically acceptable salts, hydrates, solvates and prodrugs thereof. In formula (I), the letter Y represents O or S and the ring B represents a 5-7 membered aryl or heteroaryl comprising 1 to 3 heteroatoms selected from the group consisting of N, O, and S, each aryl or heteroaryl optionally substituted with 1 to 3 $R^{4d}$ substiuents.

The symbol $R^1$ represents a member selected from the group consisting of: hydrogen, —$C_{1-6}$alkyl, —$C_{0-6}$alkylaryl, heteroaryl and —$C_{2-6}$alkenyl. The symbol $R^2$ represents a member selected from the group consisting of: —$C_{0-6}$alkylaryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The letter D represents a member selected from the group consisting of: a direct bond, aryl, heteroaryl, $C_{3-8}$cycloalkyl, $C_{3-8}$cycloalkylene, heteromonocyclyl, unfused heterobicyclyl, and fused heterobicyclyl; each of which is optionally substituted with 1 to 3 $R^9$ substituents, wherein each heterocyclyl comprises from 5 to 10 ring atoms, 1-4 of which are selected from the group consisting of N, O and S.

The symbol Q is selected from the group consisting of: a direct bond, —C(R$^{10a}$R$^{10b}$)—, —C(O)—, —C(S)—, —C(=NR$^{10a}$)—, —O—, —N(R$^{10a}$)—, —N(R$^{10a}$)CH$_2$—, —CH$_2$N(R$^{10a}$)—, —C(O)N(R$^{10a}$)—, —N(R$^{10a}$)C(O)—, —SO$_2$—, —SO—, —SO$_2$N(R$^{10a}$)—, and —N(R$^{10a}$)—SO$_2$—; and at least one of D and Q is not a direct bond.

The symbol A is selected from the group consisting of: —NR$^{11c}$R$^{11d}$, —C(=N$^{11c}$)NR$^{11a}$R$^{11b}$, —C(=NR$^{11e}$R$^{11f}$)NR$^{11a}$R$^{11b}$, —N(R$^{11d}$)C(=NR$^{11c}$)NR$^{11a}$R$^{11b}$, —N(R$^{11d}$)C(=NR$^{11c}$)R$^{11a}$, —N(R$^{11c}$)NR$^{11a}$R$^{11b}$, —N(R$^{11c}$)OR$^{11d}$, C$_{1-6}$alkyl, C$_{2-6}$alkenyl, aryl, heteroaryl, —C$_{3-8}$cycloalkyl, —C$_{3-8}$cycloalkenyl, heteromonocyclyl, and fused heterobicyclyl; each of aryl, heteroaryl, heteromonocyclyl and fused heterobicyclyl, optionally substituted with 1 to 3 R$^{11g}$; wherein each hetercyclyl comprises from 5 to 10 ring atoms, 1-4 of which are selected from the group consisting of N, O and S; wherein each hetercyclyl comprises from 5 to 10 ring atoms, 1-4 of which are selected from the group consisting of N, O and S. Each R$^{2a}$, R$^{3d}$, R$^{4d}$, R$^9$ and R$^{11g}$ is a member independently selected from the group consisting of: H, halo, C$_{1-6}$alkyl, C$_{2-6}$alkenyl, C$_{2-6}$alkynyl, C$_{0-4}$alkylC$_{3-8}$cycloalkyl, —O—C$_{0-2}$alkyl-CF$_3$, —C$_{0-2}$alkyl-CF$_3$, —C$_{0-2}$alkyl-CN, —C$_{0-2}$alkyl-NO$_2$, —C—C$_{0-2}$alkyl-SO$_2$NR$^{12a}$R$^{12b}$, —C$_{0-2}$alkyl-SO$_2$R$^{12a}$, —C$_{0-2}$alkyl-SOR$^{12a}$, —C$_{0-2}$alkyl-CF$_3$, —C$_{0-2}$alkyl-OR$^{12a}$, —C$_{0-2}$alkyl-SR$^{12a}$, —O—CH$_2$—CH$_2$—OR$^{12a}$, —O—CH$_2$—CO$_2$R$^{12a}$, —N(R$^{12a}$)—CH$_2$—CH$_2$—OR$^{12b}$, —C$_{0-2}$alkyl-C(O)NR$^{12a}$R$^{12b}$, —C$_{0-2}$alkyl-CO$_2$R$^{12a}$, —(CH$_2$)$_m$N(R$^{12a}$)—C(O)R$^{12b}$, —C$_{0-2}$alkyl-N(R$^{12c}$)—C(O)NR$^{12a}$R$^{12b}$, —C$_{0-2}$alkyl-C(=NR$^{12c}$)NR$^{12a}$R$^{12b}$, —C$_{0-2}$alkyl-C(=NR$^{12a}$)R$^{12b}$, —C$_{0-2}$alkyl-N(R$^{12d}$)C(=NR$^{12c}$)NR$^{12a}$R$^{12b}$, —C$_{0-2}$alkyl-N(R$^{12a}$)—SO$_2$—R$^{12b}$, =O, =S, =NR$^{12a}$, 5- or 6-membered aryl, 5- or 6-membered heteroaryl and 5- to 7-membered heterocyclyl, each of which is optionally substituted with a member independently selected from the group consisting of halo, CF$_3$, OCF$_3$, SCF$_3$, C$_{1-6}$alkyl, C$_{2-6}$alkenyl, C$_{2-6}$alkynyl, C$_{0-4}$alkylC$_{3-8}$cycloalkyl, C$_{1-4}$alkoxy, —CO$_2$H, —CO$_2$C$_{1-4}$alkyl, —CONR$^{12a}$R$^{12b}$, =O, =S, —OH, —CN and —NO$_2$; wherein each heteroaryl or heterocyclyl comprises 1 to 4 heteroatoms, independently selected from the group consisting of N, O and S. Each of the symbols R$^{11a}$, R$^{11b}$, R$^{11c}$, R$^{11d}$, R$^{11e}$, R$^{11f}$, R$^{12a}$, R$^{12b}$, R$^{12c}$ and R$^{12d}$ are members independently selected from the group consisting of: H, C$_{1-6}$alkyl, C$_{2-6}$alkenyl, C$_{2-6}$alkynyl, C$_{0-4}$alkylC$_{3-8}$cycloalkyl, C$_{0-4}$alkylaryl, C$_{0-4}$alkyl-heteroaryl, —C$_{0-6}$alkyl-COC$_{1-4}$alkyl, —C$_{0-6}$alkyl-SO$_2$—C$_{1-4}$alkyl, —C$_{0-6}$alkyl-SO$_2$—N(C$_{1-4}$alkyl, C$_{1-4}$alkyl), —C$_{0-6}$alkyl-N(C$_{1-4}$alkyl, C$_{1-4}$alkyl) and —C$_{1-6}$alkyl-O—C$_{0-6}$alkyl, wherein 1-3 hydrogen atoms on the aryl or heteroaryl ring may be independently replaced with a member selected from the group consisting of halo, C$_{1-6}$alkyl, C$_{2-6}$alkenyl, C$_{2-6}$alkynyl, C$_{0-4}$alkylC$_{3-8}$cycloalkyl, C$_{1-4}$alkoxy, —CO$_2$H, —CO$_2$C$_{1-4}$alkyl, —CON(C$_{1-4}$alkyl, C$_{1-4}$alkyl), —OH, —CN and NO$_2$; or can be taken together with the nitrogen atom to which they are attached to form a 3-8 membered heterocyclyl group, comprising 1 to 4 heteroatoms selected from the group consisting of N, O and S, optionally substituted with 1 to 4 R$^{13}$ substituents selected from the group consisting of halo, C$_{1-6}$alkyl, C$_{2-6}$alkenyl, C$_{2-6}$alkynyl, C$_{0-4}$alkylC$_{3-8}$cycloalkyl, C$_{1-4}$alkoxy, —CO$_2$H, —CO$_2$C$_{1-4}$alkyl, —CON(C$_{1-4}$alkyl, C$_{1-4}$alkyl), =O, =S, —OH, —CN and NO$_2$. Each of the symbols R$^6$, R$^7$, R$^8$, R$^{10a}$ and R$^{10b}$ is a member independently selected from the group consisting of: hydrogen, C$_{1-6}$alkyl, C$_{2-6}$alkenyl, C$_{2-6}$alkynyl and C$_{0-4}$alkylC$_{3-8}$cycloalkyl, —C$_{0-6}$alkyl-aryl and —C$_{0-6}$alkyl-heteraryl.

Each subscript n1 and n2 represents an integer of 0 to 1; and each subscript n3 and n4 represents an integer of 0 to 2.

With the above formula are a number of specific embodiments of the invention. In one group of embodiments, R$^1$ is H. In a specific group of embodiments, R$^2$ is aryl, optionally substituted with 1 to 3 R$^{2a}$. More preferably, R$^2$ is thienyl or phenyl. More preferably, R$^{2a}$ is halo. For these embodiments, a preferred group of embodiments are those in which R$^{2a}$ is attached to the phenyl ring at a position para to the rest of the molecule.

In one group of embodiments, the moiety:

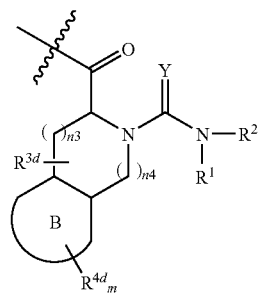

is selected from the group consisting of:

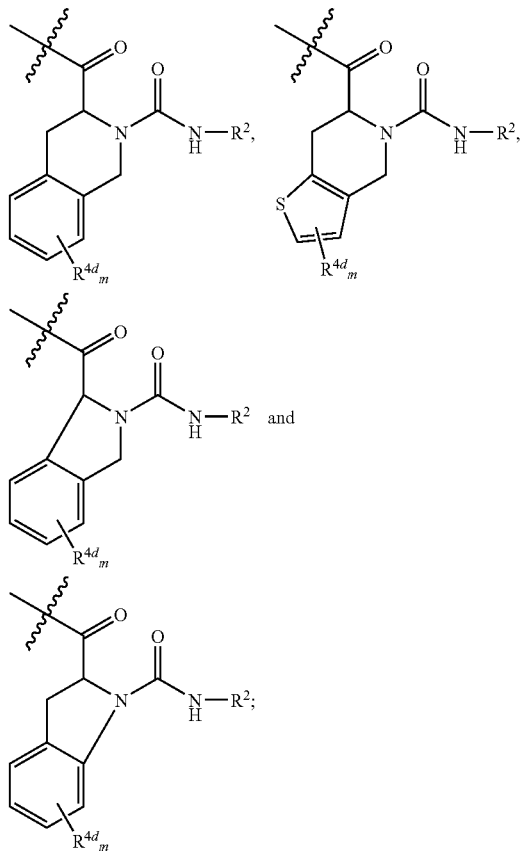

wherein the subscript m is an integer of 0 to 3. In a specific group of embodiments the moiety:

is selected from the group consisting of:

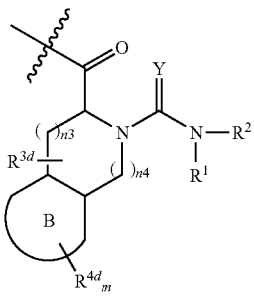

is selected from the group consisting of:

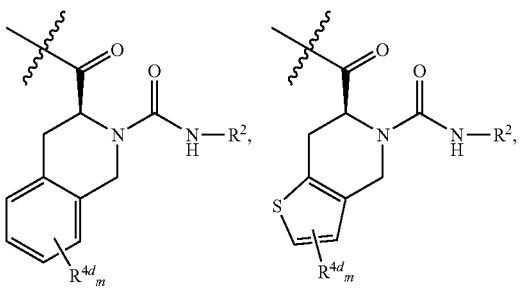

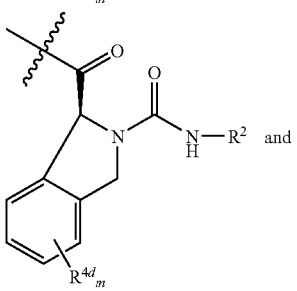

wherein the subscript m is an integer of 0 to 3. In another group of embodiments the moiety:

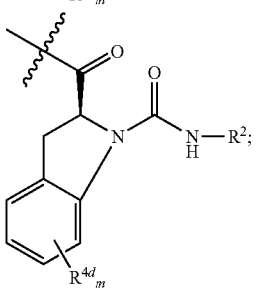

is selected from the group consisting of:

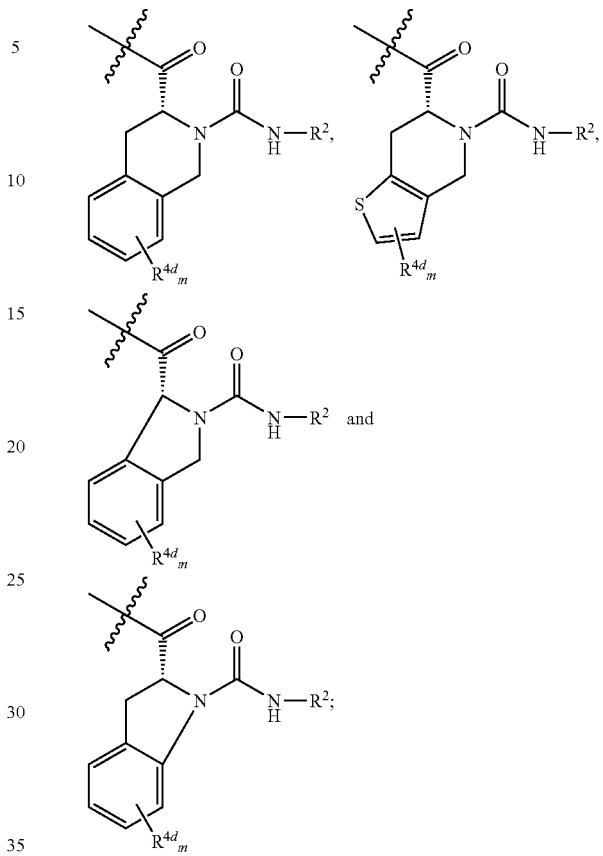

wherein the subscript m is an integer of 0 to 3.

In one group of embodiments, the subscript n1 is 0. In another group of embodiments the subscript n1 is 1. In a specific group of embodiments $R^6$ is H. In one group of embodiments, the subscript n2 is 0. In another group of embodiments the subscript n2 is 1. In a specific group of embodiments each $R^7$ and $R^8$ is H.

In one group of embodiments, D is aryl or heteromonocyclyl, wherein each heterocyclyl comprises from 5 to 7 ring atoms, 1 to 2 of which are N or O. More preferably, D is phenyl, piperidinyl, or piperazinyl. In another group of embodiments, Q is a direct bond, —C(=NH)—, —C(O)— or —N($R^{10a}$)—. More preferably, Q is attached to the phenyl, piperidinyl or piperazinyl ring at a position para to the rest of the molecule.

In another group of embodiments, A is selected from the group consisting of: —N$R^{11a}R^{11b}$, aryl, heteroaryl and heteromonocyclyl; each of aryl, heteroaryl, heteromonocyclyl and fused heterobicyclyl, optionally substituted with 1 to 3 $R^{11g}$; wherein each hetercyclyl comprises from 5 to 7 ring atoms, 1 to 2 of which are N, O or S. More preferably, A is a member selected from the group consisting of dihydroimidazolyl, pyridinyl, pyrrolidinyl, homopiperazinyl, piperazinyl, morpholinyl, thiazolidinyl, piperidinyl and oxazolidinyl. Still further preferred are those embodiments in which each optional substituent $R^{11g}$ is independently selected from the group consisting of $C_{1-6}$alkyl, —$C_{0-2}$alkyl-N$R^{12a}R^{12b}$ and =O. Still further preferred are those embodiments in wherein A-Q-D-(C$R^7R^8$)$_{n2}$—N$R^6_{n1}$ selected from the group consisting of:

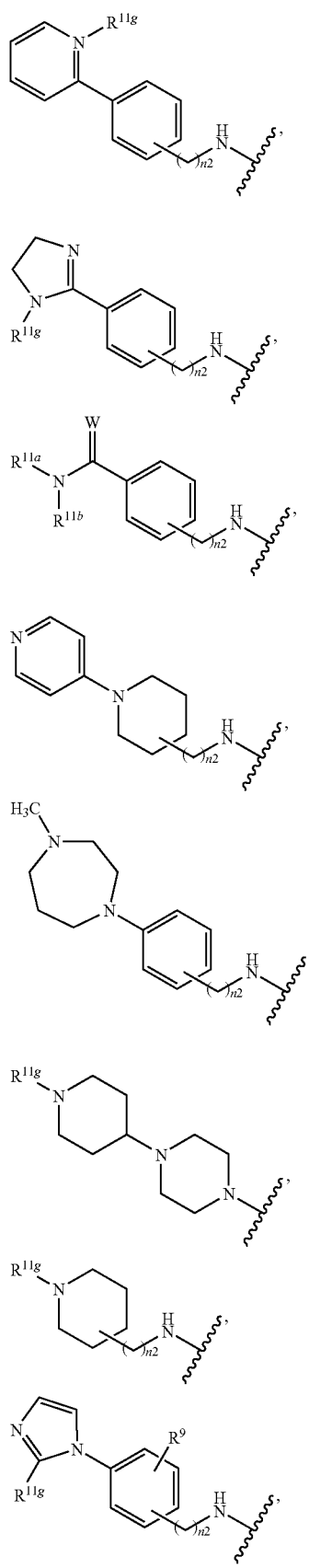
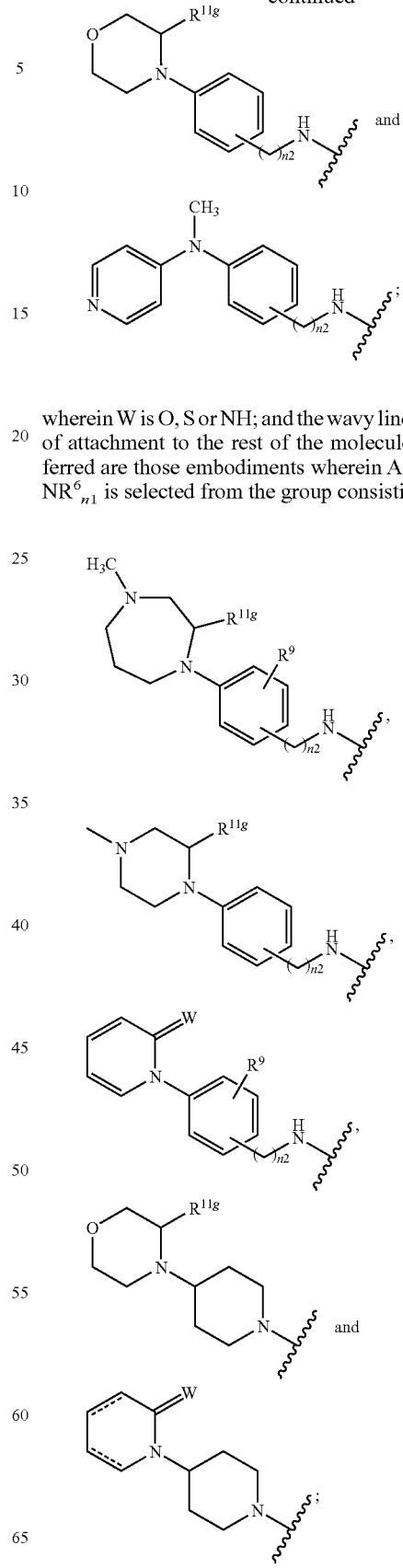
wherein W is O, S or NH; and the wavy line indicates the point of attachment to the rest of the molecule. Still further preferred are those embodiments wherein A-Q-D-(CR$^7$R$^8$)$_{n2}$—NR$^6_{n1}$ is selected from the group consisting of:

wherein W is O, S or NH; each dashed line independently indicates a single or double bond; and the wavy line indicates the point of attachment to the rest of the molecule. Still further preferred are those embodiments wherein A-Q- is selected from the group consisting of:

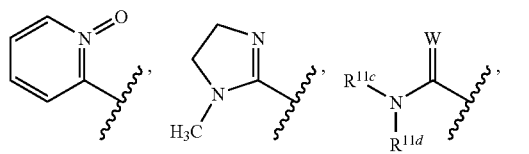

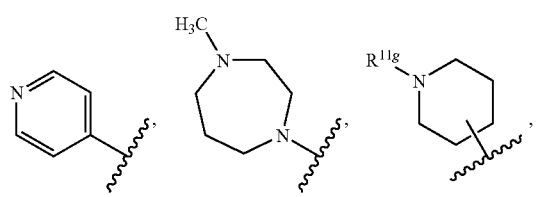

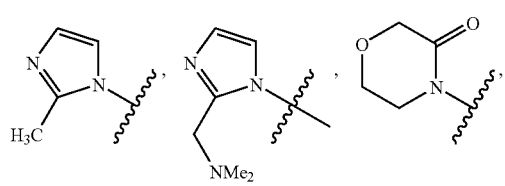

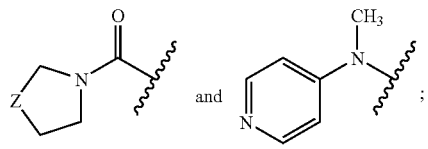

wherein W is O, S or NH; Z is O, S, or NH; and the wavy line indicates the point of attachment to the rest of the molecule. Still further preferred are those embodiments wherein A-Q- is selected from the group consisting of:

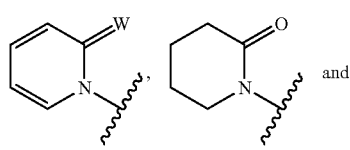

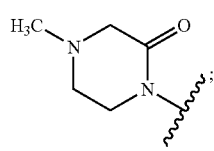

wherein W is O, S or NH; and the wavy line indicates the point of attachment to the rest of the molecule.

In other embodiments, compounds of formula I are provided which have the formula:

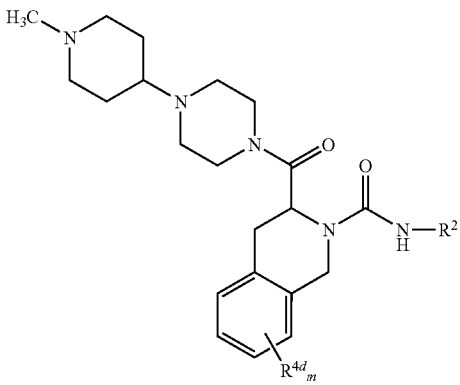

wherein $R^2$ is aryl, optionally substituted with 1 to 3 $R^{2a}$. Within this group, specific embodiments are provided in which $R^2$ is thienyl or phenyl. Preferably, the optional substituent $R^{2a}$ is halo. Still further preferred are embodiments, wherein $R^{2a}$ is attached to the phenyl ring at a position para to the rest of the molecule. In other embodiments, compounds are provided in which each $R^{4d}$ is independently selected from the group consisting of: hydrogen, $C_{1-6}$alkyl and $C_{0-2}$alkyl-$OR^{12a}$. In a specific group of embodiments the moiety:

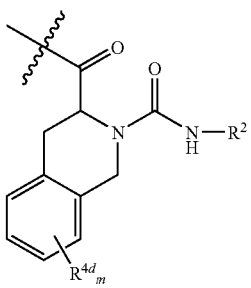

is:

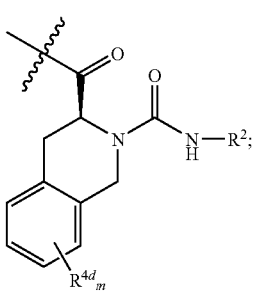

wherein the subscript m is an integer of 0 to 3. In another group of embodiments the moiety:

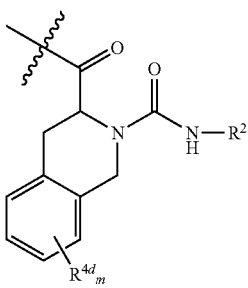

is:

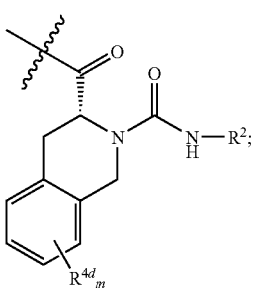

wherein the subscript m is an integer of 0 to 3.

In other embodiments, compounds of formula I are provided which have the formula:

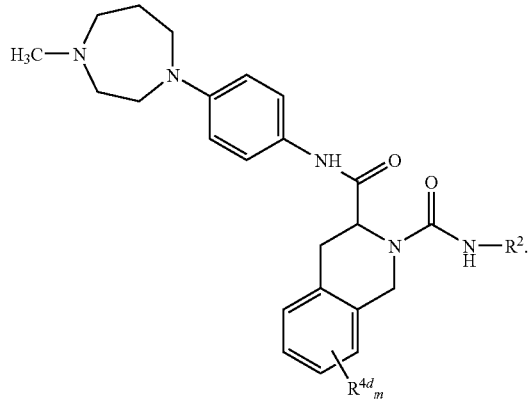

Within this group, specific embodiments are provided in which $R^2$ is aryl, optionally substituted with 1 to 3 $R^{2a}$. Preferably, $R^2$ is thienyl or phenyl. Still further preferred are embodiments wherein each optional substituent $R^{2a}$ is halo. Still further preferred are embodiments wherein $R^{2a}$ is attached to the phenyl ring at a position para to the rest of the molecule. In other embodiments, compounds are provided in which each $R^{4d}$ is independently selected from the group consisting of: hydrogen, $C_{1-6}$alkyl and $C_{0-2}$alkyl-$OR^{12a}$. In a specific group of embodiments the moiety:

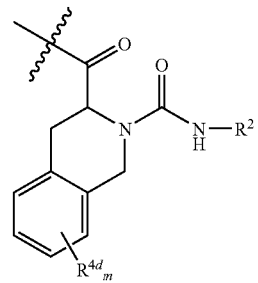

is:

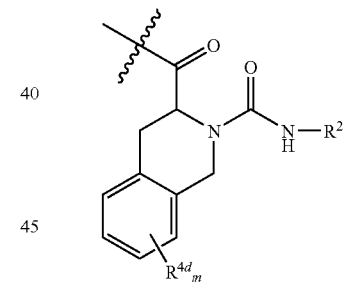

wherein the subscript m is an integer of 0 to 3. In another group of embodiments the moiety:

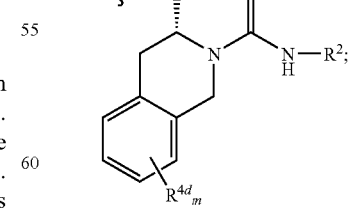

is:

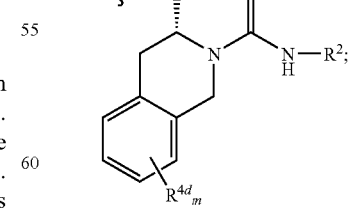

wherein the subscript m is an integer of 0 to 3.

In other embodiments, compounds of formula I are provided which have the formula:

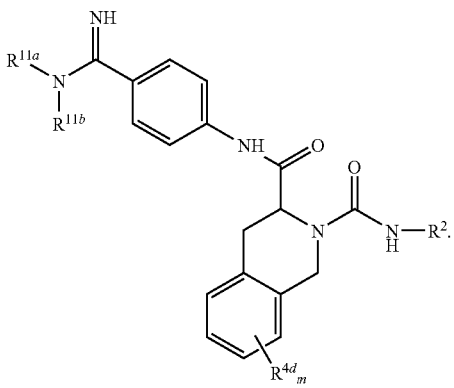

Within this group, specific embodiments are provided in which $R^2$ is aryl, optionally substituted with 1 to 3 $R^{2a}$. Preferably, $R^2$ is thienyl or phenyl. Still further preferred are embodiments wherein each optional substituent $R^{2a}$ are halo. Still further preferred are embodiments wherein $R^{2a}$ is attached to the phenyl ring at a position para to the rest of the molecule. In other embodiments, compounds are provided in which each $R^{4d}$ is independently selected from the group consisting of: hydrogen, $C_{1-6}$alkyl and $C_{0-2}$alkyl-$OR^{12a}$. In a specific group of embodiments the moiety:

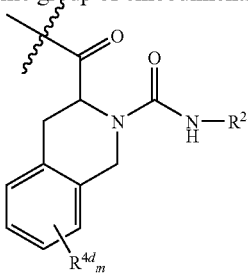

is:

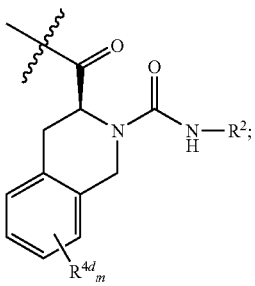

wherein the subscript m is an integer of 0 to 3. In another group of embodiments the moiety:

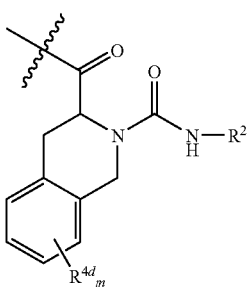

is:

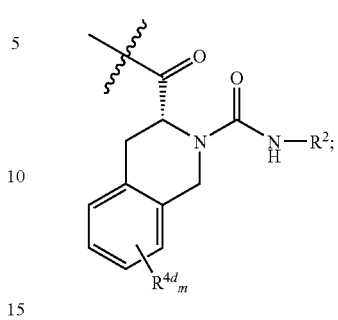

wherein the subscript m is an integer of 0 to 3.

In other embodiments, compounds are provided in which each $R^{11a}$ and $R^{11b}$ is $C_{1-6}$alkyl.

Within the present invention, the compounds provided in the examples below are each preferred embodiments, along with their pharmaceutically acceptable salts, hydrates, solvates and prodrugs thereof. Preferred examples of compounds of formula (I) include:

N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide;

N-[4-(1N-oxo-pyridin-2-yl)phenyl]-2N-(4-chlorophenylaminocarbonyl)-1,2,3,4-tetrahydroisoquinoline-3-carboxamide;

(3S)-N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide;

N-[4-(pyrrolidinylimino)phenyl]-2N-(4-chlorophenylaminocarbonyl)-1,2,3,4-tetrahydroisoquinoline-3-carboxamide;

N-[4-(dimethylaminoimino)phenyl]-2N-(4-chlorophenylaminocarbonyl)-1,2,3,4-tetrahydroisoquinoline-3-carboxamide;

N-[3-(dimethylaminoimino)benzyl]-2N-(4-chlorophenylaminocarbonyl)-1,2,3,4-tetrahydroisoquinoline-3-carboxamide;

N-[3-(1-methyl-4,5-dihydro-1H-imidazol-2-yl)benzyl]-2N-(4-chlorophenylaminocarbonyl)-1,2,3,4-tetrahydroisoquinoline-3-carboxamide;

N-[4-(pyrrolidinylcarbonyl)phenyl]-2N-(4-chlorophenylaminocarbonyl)-1,2,3,4-tetrahydroisoquinoline-3-carboxamide;

N-[1-(pyridin-4-yl)piperidin-4-yl]methyl-2N-(4-chlorophenylaminocarbonyl)-1,2,3,4-tetrahydroisoquinoline-3-carboxamide;

N-[4-(4-methyl-homopiperazinyl)]phenyl-2N-(4-chlorophenylaminocarbonyl)-1,2,3,4-tetrahydroisoquinoline-3-carboxamide;

4-(1-methylpiperidin-4-yl)piperazinyl 2N-(4-chlorophenylaminocarbonyl)-1,2,3,4-tetrahydroisoquinoline-3-carboxamide;

N-(1-isopropylpiperidin-4-yl)2N-(4-chlorophenylaminocarbonyl)-1,2,3,4-tetrahydroisoquinoline-3-carboxamide;

N-[4-(2-dimethylaminomethyl-imidazol-1-yl)-2-fluorophenyl]-2N-(4-chlorophenylaminocarbonyl)-1,2,3,4-tetrahydroisoquinoline-3-carboxamide;

N-[4-(3-oxo-morpholin-4-yl)phenyl]-2N-(4-chlorophenylaminocarbonyl)-1,2,3,4-tetrahydroisoquinoline-3-carboxamide;

N-[4-(3-thiazolidinylcarbonyl)phenyl]-2N-(4-chlorophenylaminocarbonyl)-1,2,3,4-tetrahydroisoquinoline-3-carboxamide;
N-[4-(3-oxazolidinylcarbonyl)phenyl]-2N-(4-chlorophenylaminocarbonyl)-1,2,3,4-tetrahydroisoquinoline-3-carboxamide;
N-[4-(N-methyl-N-pyridin-4-yl-amino)phenyl]-2N-(4-chlorophenylaminocarbonyl)-1,2,3,4-tetrahydroisoquinoline-3-carboxamide;
N-[4-(1-methyl-4,5-dihydro-1H-imidazol-2-yl)phenyl]-2N-(4-chlorophenylaminocarbonyl)-5-methyl-1,2,3,4-tetrahydroisoquinoline-3-carboxamide;
N-[4-(pyrrolidinylimino)phenyl]-2N-(4-chlorophenylaminocarbonyl)-5-methyl-1,2,3,4-tetrahydroisoquinoline-3-carboxamide;
N-[4-(dimethylaminoimino)phenyl]-2N-(4-chlorophenylaminocarbonyl)-5-methyl-1,2,3,4-tetrahydroisoquinoline-3-carboxamide;
(3S)-N-[4-(1-methyl-4,5-dihydro-1H-imidazol-2-yl)phenyl]-2N-(4-chlorophenylaminocarbonyl)-6,7-dimethoxy-1,2,3,4-tetrahydroisoquinoline-3-carboxamide;
(3S)-N-[4-(pyrrolidinylimino)phenyl]-2N-(4-chlorophenylaminocarbonyl)-6,7-dimethoxy-1,2,3,4-tetrahydroisoquinoline-3-carboxamide;
(3S)-N-[4-(dimethylaminoimino)phenyl]-2N-(4-chlorophenylaminocarbonyl)-6,7-diemthoxy-1,2,3,4-tetrahydroisoquinoline-3-carboxamide;
N-[4-(1-methyl-4,5-dihydro-1H-imidazol-2-yl)phenyl]-2N-(4-chlorophenylaminocarbonyl)-6-hydroxy-1,2,3,4-tetrahydroisoquinoline-3-carboxamide;
N-[4-(1-methyl-4,5-dihydro-1H-imidazol-2-yl)phenyl]-5N-(4-chlorophenylaminocarbonyl)-4,5,6,7-tetrahydro-thieno[3,2-c]pyridine-6-carboxamide;
N-[4-(dimethylaminoimino)phenyl]-5N-(4-chlorophenylaminocarbonyl)-4,5,6,7-tetrahydro-thieno[3,2-c]pyridine-6-carboxamide;
N-[4-(4-methyl-homopiperazinyl)]phenyl-5N-(4-chlorophenylaminocarbonyl)-4,5,6,7-tetrahydro-thieno[3,2-c]pyridine-6-carboxamide;
N-[4-(1-methyl-4,5-dihydro-1H-imidazol-2-yl)phenyl]-2N-(4-chlorophenylaminocarbonyl)-2,3-dihydro-1H-isoindole-1-carboxamide;
N-[4-(1N-oxo-pyridin-2-yl)phenyl]-2N-(4-chlorophenylaminocarbonyl)-2,3-dihydro-1H-isoindole-1-carboxamide;
N-[4-(4-methyl-homopiperazinyl)phenyl]-2N-(4-chlorophenylaminocarbonyl)-2,3-dihydro-1H-isoindole-1-carboxamide;
N-[4-(3-oxo-morpholin-4-yl)phenyl]-2N-(4-chlorophenylaminocarbonyl)-2,3-dihydro-1H-isoindole-1-carboxamide;
N-[4-(1N-oxo-pyridin-2-yl)phenyl]-1N-(4-chlorophenylaminocarbonyl)-indoline-2-carboxamide;
(3R) N-[4-(4-methyl-homopiperazinyl)]phenyl-2N-(4-chlorophenylaminocarbonyl)-1,2,3,4-tetrahydroisoquinoline-3-carboxamide;
(3S)N-[4-(4-methyl-homopiperazinyl)]phenyl-2N-(4-chlorophenylaminocarbonyl)-1,2,3,4-tetrahydroisoquinoline-3-carboxamide;
(3R) N-[4-(4-methyl-homopiperazinyl)-2-fluorophenyl]-2N-(4-chlorophenylaminocarbonyl)-1,2,3,4-tetrahydroisoquinoline-3-carboxamide;
(3R) N-[4-(2-pyridon-1-yl)phenyl]-2N-(4-chlorophenylaminocarbonyl)-1,2,3,4-tetrahydroisoquinoline-3-carboxamide;
(3S)N-[4-(2-pyridon-1-yl)phenyl]-2N-(4-chlorophenylaminocarbonyl)-1,2,3,4-tetrahydroisoquinoline-3-carboxamide;
(3R) N-[4-(2-pyridon-1-yl)-2-fluorophenyl]-2N-(4-chlorophenylaminocarbonyl)-1,2,3,4-tetrahydroisoquinoline-3-carboxamide;
N-[4-(2-pyridon-1-yl)phenyl]-2N-(4-chlorophenylaminocarbonyl)-6-hydroxy-1,2,3,4-tetrahydroisoquinoline-3-carboxamide;
N-[4-(4-methyl-homopiperazinyl)phenyl]-2N-(4-chlorophenylaminocarbonyl)-6-hydroxy-1,2,3,4-tetrahydroisoquinoline-3-carboxamide;
N-[4-(2-thiopyridon-1-yl)phenyl]-2N-(4-chlorophenylaminocarbonyl)-6-hydroxy-1,2,3,4-tetrahydroisoquinoline-3-carboxamide;
(3R) 4-(2-piperidinon-1-yl)piperidin-1-yl 2N-(4-chlorophenylaminocarbonyl)-1,2,3,4-tetrahydroisoquinoline-3-carboxamide;
(3R) 4-(2-pyridon-1-yl)piperidin-1-yl 2N-(4-chlorophenylaminocarbonyl)-1,2,3,4-tetrahydroisoquinoline-3-carboxamide;
(3R) 4-(3-morpholinon-4-yl)piperidin-1-yl 2N-(4-chlorophenylaminocarbonyl)-1,2,3,4-tetrahydroisoquinoline-3-carboxamide;
(3R) N-[4-(4-methyl-2-piperazinon-1-yl)phenyl]-2N-(4-chlorophenylaminocarbonyl)-1,2,3,4-tetrahydroisoquinoline-3-carboxamide;
(3R) N-[4-(4-methyl-2-homopiperazinon-1-yl)phenyl]-2N-(4-chlorophenylaminocarbonyl)-1,2,3,4-tetrahydroisoquinoline-3-carboxamide;
(3R) N-[4-(2-pyridon-1-yl)phenyl]-2N-(4-fluorophenylaminocarbonyl)-1,2,3,4-tetrahydroisoquinoline-3-carboxamide;
(3R) N-[4-(2-pyridon-1-yl)phenyl]-2N-[5-(2-chlorothiophene)aminocarbonyl]-1,2,3,4-tetrahydroisoquinoline-3-carboxamide; and
(3R) N-[4-(4-methyl-homopiperazin-1-yl)phenyl]-2N-[5-(2-chlorothiophene)aminocarbonyl]-1,2,3,4-tetrahydroisoquinoline-3-carboxamide.

All the preferred, more preferred, and most preferred compounds listed above are selective inhibitors of Factor Xa.

Compositions

The present invention further provides compositions comprising one or more compounds of formula (I) or a tautomer or a pharmaceutically acceptable salt thereof, and a pharmaceutically acceptable carrier. It will be appreciated that the compounds of formula (I) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be in any orally acceptable dosage form, including capsules, tablets, aqueous suspensions or solutions. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

The pharmaceutical compositions of this invention may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

Any of the above dosage forms containing effective amounts are within the bounds of routine experimentation and within the scope of the invention. A therapeutically effective dose may vary depending upon the route of administration and dosage form. The preferred compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

Methods of Use

The invention provides methods of inhibiting or decreasing Factor Xa activity as well as treating or ameliorating a Factor Xa associated state, symptom, disorder or disease in a patient in need thereof (e.g., human or non-human). "Treating" within the context of the invention means an alleviation of symptoms associated with a disorder or disease, or halt of further progression or worsening of those symptoms, or prevention or prophylaxis of the disease or disorder.

The term "mammal" includes organisms which express Factor Xa. Examples of mammals include mice, rats, cows, sheep, pigs, goats, horses, bears, monkeys, dogs, cats and, preferably, humans. Transgenic organisms which express Factor Xa are also included in this definition.

The inventive methods comprise administering an effective amount of a compound or composition described herein to a mammal or non-human animal. As used herein, "effective amount" of a compound or composition of the invention includes those amounts that antagonize or inhibit Factor Xa. An amount which antagonizes or inhibits Factor Xa is detectable, for example, by any assay capable of determining Factor Xa activity, including the one described below as an illustrative testing method. Effective amounts may also include those amounts which alleviate symptoms of a Factor Xa associated disorder treatable by inhibiting Factor Xa. Accordingly, "antagonists of Factor Xa" include compounds which interact with the Factor Xa and modulate, e.g., inhibit or decrease, the ability of a second compound, e.g., another Factor Xa ligand, to interact with the Factor Xa. The Factor Xa binding compounds are preferably antagonists of Factor Xa. The language "Factor Xa binding compound" (e.g., exhibits binding affinity to the receptor) includes those compounds which interact with Factor Xa resulting in modulation of the activity of Factor Xa. Factor Xa binding compounds may be identified using an in vitro (e.g., cell and non-cell based) or in vivo method. A description of an in vitro method is provided below.

The amount of compound present in the methods and compositions described herein should be sufficient to cause a detectable decrease in the severity of the disorder, as measured by any of the assays described in the examples. The amount of Factor Xa modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt or solvate according to the formula I, another therapeutic agent (e.g., methotrexate) or a pharmaceutically acceptable salt or solvate thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where Factor Xa plays a role.

EXAMPLES

Example 1

N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide

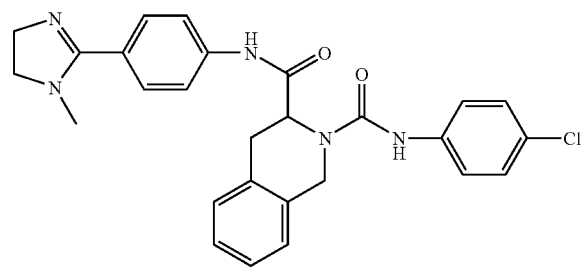

A. Preparation of 2n-(4-chlorophenylaminocarbonyl)-1,2,3,4-tetrahydroisoquinoline-3-carboxylic acid To a solution of 1,2,3,4-tetrahydroisoquinoline-3-carboxylic acid hydrochloride (508 mg, 2.38 mmol) in 1N aq. NaOH (10 mL), a solution of 4-chlorophenylisocyanate (715 mg, 4.65 mmol) in dioxane (10 mL) was added. The mixture was stirred at room temperature overnight. It was then washed with Et₂O (2×). The aqueous layer was separated, acidified with 4N HCl to pH 1 to 2. The product was extracted with EtOAc. The EtOAc solution was dried over Na₂SO₄, concentrated in vacuo to give a solid (530 mg), which was sufficiently pure to be used in the next reaction.

B. Preparation of 4-(1-Methyl-4,5-dihydro-1H-imidazol-2-yl)-phenylamine

To a solution of 4-aminobenzonitrile (5.1 g, 43 mmol) in dry methanol (60 mL) at 0° C., hydrogen chloride gas was bubbled through until saturation was reached. The mixture was then stirred at room temperature overnight. It was concentrated in vacuo. The residue was dissolved in dry methanol (60 mL). To the solution, N-methyl ethylenediamine (19 mL, 216 mmol) was added. The mixture was then heated to reflux for 3 h. After being cooled in fridge overnight, the precipitated product was collected by filtration, then was dried on vacuum to give white solids (3.7 g). MS 176.0 (M+H).

C. Preparation of N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (68 mg, 0.21 mmol) and 4-(1-Methyl-4,5-dihydro-1H-imidazol-2-yl)-phenylamine (75 mg, 0.43 mmol) in DMF (3 mL) and H₂O (1 mL) at room temperature, EDC (157 mg, 0.82 mmol) was added. The mixture was stirred at room temperature overnight. It was concentrated in vacuo. The residue was purified by HPLC to give a white solid (58 mg). MS 488.4 and 490.4 (M+H, Cl pattern).

Example 2

N-[4-(1N-oxo-pyridin-2-yl)phenyl]-2N-(4-chlorophenylaminocarbonyl)-1,2,3,4-tetrahydroisoquinoline-3-carboxamide

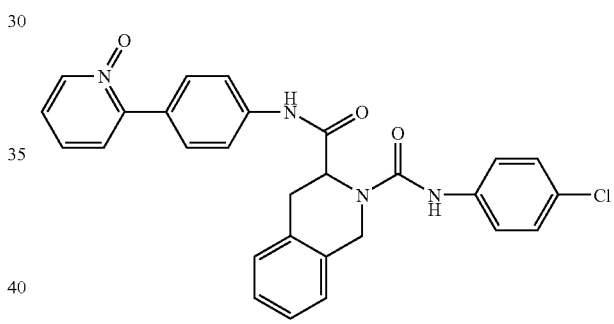

A. Preparation of 4-(2-pyridinyl)phenylamine

To a solution of 4-(4,4,5,5-tetramethyl-1,3,2-dioxaborolan-2-yl)aniline (2.66 g, 12.1 mmol) in toluene (20 mL) and n-butanol (7 mL), a solution of 2-bromopyridine (0.991 g, 6.27 mmol) and Cs₂CO₃ (6.10 g, 18.7 mmol) in H₂O (20 mL) was added. The mixture was degassed three times with Ar/vacuum cycle before being charged with Pd(Ph₃P)₄ (540 mg, 0.46 mmol, 7% mol). It was then heated at reflux under Ar overnight. The reaction mixture was allowed to cool at room temperature, and then in an ice-bath. The precipitates were collected, dried on vacuum to give a solid (0.840 g)

B. Preparation of N-BOC-[4-(1N-oxo-pyridin-2-yl)]phenylamine

To a solution of 4-(2-pyridinyl)phenylamine (0.840 g, 4.94 mmol) and TEA (2.06 mL, 14.8 mmol) in CH₂Cl₂ (20 mL), di-t-butyl dicarbonate (1.36 mL, 5.93 mmol) was added. After being stirred at room temperature for 2 days, the mixture was concentrated in vacuo. The residue was purified by a silica gel column to give a solid (1.06 g), which was then dissolved in acetone (20 mL). To the solution, mCPBA (ca. 70%, 1.45 g, 5.87 mmol) was added. After being stirred at room temperature overnight, the mixture was concentrated in vacuo. The residue was purified by a silica gel column to give the desired product as an off-white solid (0.673 g).

C. Preparation of 4-(1N-oxo-pyridin-2-yl)phenylamine

A solution of N-BOC-[4-(1N-oxo-pyridin-2-yl)]phenylamine (0.673 g, 2.35 mmol) in 4N HCl in dioxane (10 mL) was stirred at room temperature overnight. It was then concentrated in vacuo to give a solid (0.481 g). MS 187.0 (M+H) and 209.0 (M+Na)

D. Preparation of N-[4-(1N-oxo-pyridin-2-yl)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (60 mg, 0.18 mmol) and 4-(1N-oxo-pyridin-2-yl)phenylamine (50 mg, 0.22 mmol) in DMF (4 mL) and H$_2$O (1 mL) at room temperature, EDC (100 mg, 0.52 mmol) was added. The mixture was stirred at room temperature overnight. It was concentrated in vacuo. The residue was purified by HPLC to give a white solid (24 mg). MS 499.5 and 501.5 (M+H, Cl pattern).

Example 3

(3S)-N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide

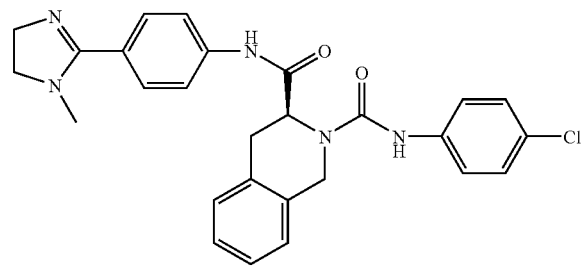

A. Preparation of (3S)-2N-(4-chlorophenylaminocarbonyl)-12,3,4-tetrahydroisoquinoline-3-carboxylic acid The intermediate was prepared analogously to the procedures described in step A of Example 1, starting from (3S)-1,2,3,4-tetrahydroisoquinoline-3-carboxylic acid.

B. Preparation of (3S)-N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide The final product was prepared analogously to the procedure described in step C of Example 1, starting from (3S)-2N-(4-chlorophenylaminocarbonyl)-1,2,3,4-tetrahydroisoquinoline-3-carboxylic acid. MS 488.6 and 490.6 (M+H, Cl pattern).

Example 3

(3R)-N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide

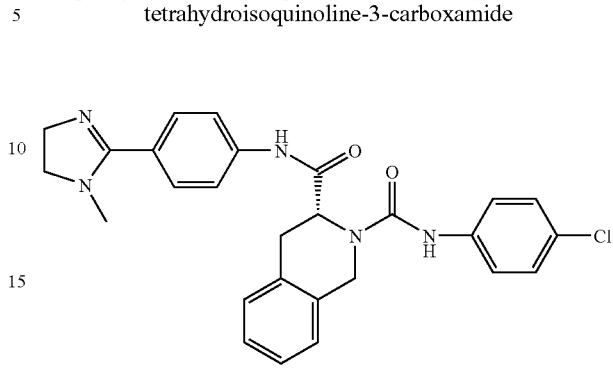

A. Preparation of (3R)-2N-(4-chlorophenylaminocarbonyl)-1,2,3,4-tetrahydroisoquinoline-3-carboxylic acid The intermediate was prepared analogously to the procedures described in step A of Example 1, starting from (3R)-1,2,3,4-tetrahydroisoquinoline-3-carboxylic acid.

B. Preparation of (3R)-N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide The final product was prepared analogously to the procedure described in step C of Example 1, starting from (3R)-2N-(4-chlorophenylaminocarbonyl)-1,2,3,4-tetrahydroisoquinoline-3-carboxylic acid. MS 488.2 and 490.2 (M+H, Cl pattern).

Example 4

N-[4-(pyrrolidinylimino)phenyl]-2N-(4-chlorophenylaminocarbonyl)-1,2,3,4-tetrahydroisoquinoline-3-carboxamide

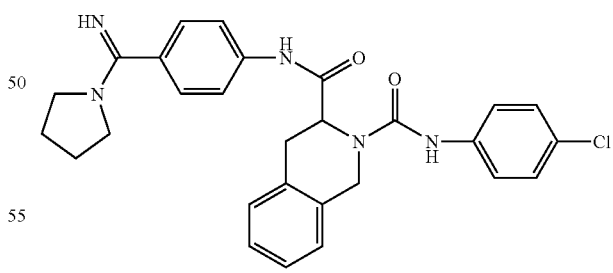

A. Preparation of 4-(pyrrolidinylimino)phenylamine

To a solution of 4-aminobenzonitrile (5.1 g, 43 mmol) in dry methanol (70 mL) at 0° C., hydrogen chloride gas was bubbled through until saturation was reached. The mixture was then stirred at room temperature overnight. It was concentrated in vacuo. The residue was suspended in dry methanol (80 mL). To the solution, pyrrolidine (22 mL, 264 mmol)

was added. The mixture was then heated to reflux for 30 min, during which time the mixture became clear. It was then stirred at room temperature overnight. It was concentrated in vacuo. The residue was dissolved in methanol (90 mL). To the solution, Et$_2$O (170 mL) was added. After being cooled in fridge overnight, the precipitated product was collected by filtration. It was then dried on vacuum to give white solids (4.5 g). MS 190 (M+H)

B. Preparation of N-[4-(pyrrolidinylimino)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (75 mg, 0.23 mmol) and 4-(pyrrolidinylimino)phenylamine (86 mg, 0.46 mmol) in DMF (4 mL) and H$_2$O (1 mL) at room temperature, EDC (89 mg, 0.46 mmol) was added. The mixture was stirred at room temperature overnight. It was concentrated in vacuo. The residue was purified by HPLC to give a white solid (55 mg). MS 502.2 and 504.2 (M+H, Cl pattern).

Example 5

N-[4-(dimethylaminoimino)phenyl]-2N-(4-chlorophenylaminocarbonyl)-1,2,3,4-tetrahydroisoquinoline-3-carboxamide

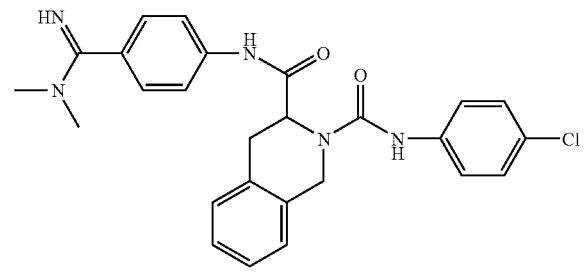

A. Preparation of 4-(dimethylaminoimino)phenylamine

To a solution of 4-aminobenzonitrile (5.1 g, 43 mmol) in dry methanol (70 mL) at 0° C., hydrogen chloride gas was bubbled through until saturation was reached. The mixture was then stirred at room temperature overnight. It was concentrated in vacuo. The residue was suspended in dry methanol (80 mL). To the solution, dimethylamine (2M in THF, 120 mL, 240 mmol) was added. The mixture was then heated to reflux for 30 min, during which time the mixture became clear. It was then stirred at room temperature overnight. It was concentrated in vacuo. The residue was dissolved in methanol (140 mL). To the solution, Et$_2$O (140 mL) was added. After being cooled in fridge overnight, the precipitated product was collected by filtration. It was then dried on vacuum to give white solids (5.6 g). MS 164 (M+H)

B. Preparation of N-[4-(dimethylaminoimino)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (85 mg, 0.26 mmol) and 4-(dimethylaminoimino)phenylamine (84 mg, 0.52 mmol) in DMF (4 mL) and H$_2$O (1 mL) at room temperature, EDC (101 mg, 0.52 mmol) was added. The mixture was stirred at room temperature overnight. It was concentrated in vacuo. The residue was purified by HPLC to give a white solid (55 mg). MS 476.1 and 478.2 (M+H, Cl pattern).

Examples 6 and 7

N-[3-(dimethylaminoimino)benzyl]-2N-(4-chlorophenylaminocarbonyl)-1,2,3,4-tetrahydroisoquinoline-3-carboxamide, and N-[3-(1-methyl-4,5-dihydro-1H-imidazol-2-yl)benzyl]-2N-(4-chlorophenylaminocarbonyl)-1,2,3,4-tetrahydroisoquinoline-3-carboxamide

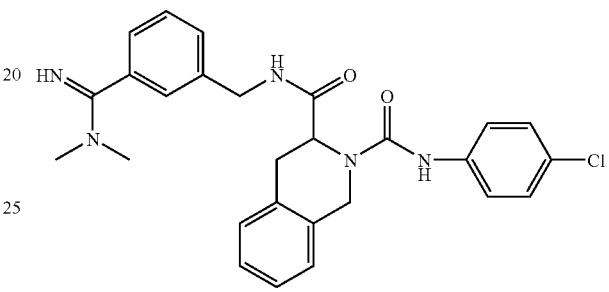

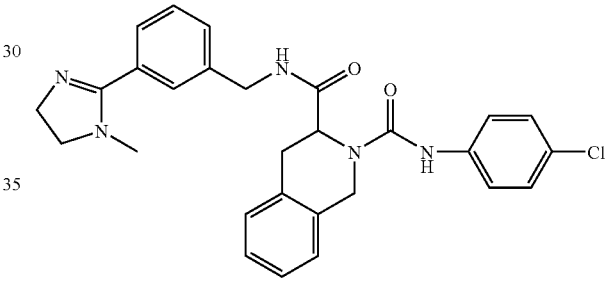

A. Preparation of 3-cyanobenzylamine

A mixture of potassium phthalimide (2.48 g, 13.4 mmol) and m-bromo-tolunitrile (2.63 g, 13.4 mmol) in DMF (40 mL) was stirred at room temperature overnight. H$_2$O and EtOAc were added. The organic layer was separated, dried over Na$_2$SO$_4$, concentrated in vacuo to give a solid (2.70 g), which was pure enough for the next reaction.

A solution of the N-(3-cyanobenzyl)phthalimide (2.70 g, 10.4 mmol) and hydrazine hydrate (2.5 mL, 51 mmol) in MeOH (50 mL) was heated to reflux for 1 h. After cooling at room temperature, CH$_2$Cl$_2$ and aq. 1N NaOH were added. The CH$_2$Cl$_2$ layer was separated, washed with brine, dried over Na$_2$SO$_4$, concentrated in vacuo to give an oil (1.10 g), which was pure enough for the next reaction. MS 133 (M+H) and 116 (M−NH2)

B. Preparation of N-(3-cyanobenzyl)-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (291 mg, 0.880 mmol) and 3-cyanobenzylamine (140 mg, 1.06 mmol) in DMF (7 mL), EDC (254 mg, 1.32 mmol) was added. The mixture was then stirred at room temperature overnight. H$_2$O and EtOAc were added. The organic layer was separated, washed with 1N HCl, dried over Na₂SO₄, concentrated in vacuo to give a solid. After being triturated with EtOAc/MeOH/CH₂Cl₂, the white solid was collected, dried on vacuum (148 mg), which was pure enough for the next reaction.

C. Preparation of N-[3-(dimethylaminoimino)benzyl]-2N-(4-chlorophenylaminocarbonyl)-1,2,3,4-tetrahydroisoquinoline-3-carboxamide, and N-[3-(1-methyl-4,5-dihydro-1H-imidazol-2-yl)benzyl]-2N-(4-chlorophenylaminocarbonyl)-1,2,3,4-tetrahydroisoquinoline-3-carboxamide To the solution of the nitrile compound from B (144 mg, 0.324 mmol) in pyridine (6 mL) and TEA (0.6 mL), H₂S gas was bubbled until saturation was reached. The solution was then stirred at room temperature overnight. It was concentrated in vacuo.

The residue was dissolved in acetone (8 mL). Iodomethane (0.202 mL, 3.24 mmol) was added. It was heated at reflux for 30 min, then concentrated in vacuo. The residue was dissolved in MeOH (12 mL). The solution was divided equally into two flasks. To one flask, a pre-mixed dimethylamine (2M in THF, 0.400 mL, 0.800 mmol) and HOAc (0.070 mL, 1.2 mmol) were added. The mixture was stirred at room temperature overnight. It was then concentrated in vacuo. The residue was purified by HPLC to give white powder (36 mg). MS 490.6 and 492.6 (M+H, Cl pattern).

To another flask, a pre-mixed N-methylethylenediamine (0.071 mL, 0.81 mmol) and HOAc (0.070 mL, 1.2 mmol) were added. The mixture was heated at reflux for 30 min. It was then stirred at room temperature overnight. After being concentrated in vacuo, the residue was purified by HPLC to give white powder (8 mg). MS 502.6 and 504.6 (M+H, Cl pattern).

Examples 8

N-[4-(pyrrolidinylcarbonyl)phenyl]-2N-(4-chlorophenylaminocarbonyl)-1,2,3,4-tetrahydroisoquinoline-3-carboxamide

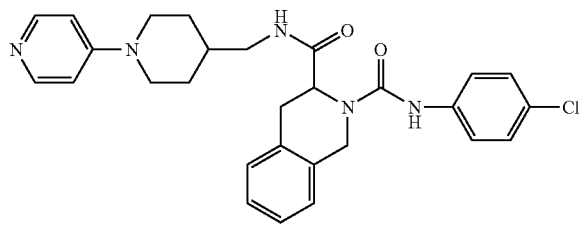

A. Preparation of 4-(pyrrolidinylcarbonyl)phenylamine hydrochloride

To a suspension of 4-nitrobenzoyl chloride (18.5 g, 100 mmol) in CH₂Cl₂ (200 mL) cooled in ice-bath, a solution of pyrrolidine (8.30 mL, 100 mmol) and TEA (28.0 mL, 200 mmol) in CH₂Cl₂ (50 mL) was added dropwise. After being stirred at room temperature overnight, the reaction solution was washed sequentially with sat. NaHCO₃, H₂O, 1N HCl, H₂O, dried over MgSO₄, concentrated in vacuo to give a solid (15 g), which was pure enough for the next reaction.

A mixture of the solid (10 g, 45 mmol) and Pd—C (10%, 0.80 g) in MeOH (200 mL) containing 4N HCl (12 mL) was hydrogenated under 50 psi on a Parr shaker overnight. It was then filtered, and the filtrate was concentrated in vacuo to give the titled compound as a solid. MS 191.1 (M+H).

B. Preparation of N-[4-(pyrrolidinylcarbonyl)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (50 mg, 0.15 mmol) and 4-(pyrrolidinylcarbonyl)phenylamine hydrochloride (41 mg, 0.18 mmol) in pyridine (4 mL) cooled in ice-bath, POCl₃ (0.14 mL, 1.5 mmol) was added. The mixture was stirred at room temperature overnight. It was then concentrated in vacuo. The residue was purified by HPLC to give a white powder (15 mg). MS 503.4 and 505.4 (M+H, Cl pattern).

Example 9

N-[1-(pyridin-4-yl)piperidin-4-yl]methyl-2N-(4-chlorophenylaminocarbonyl)-1,2,3,4-tetrahydroisoquinoline-3-carboxamide

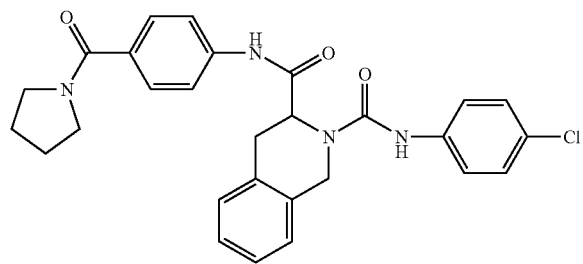

A. Preparation of 4-[1-(pyridin-4-yl)piperidinyl]methylamine hydrochloride

To a solution of 4-N-Boc-aminomethyl piperidine (1.32 g, 6.17 mmol) and sodium t-butoxide (0.741 g, 7.71 mmol) in dioxane (10 mL), 4-bromopyridine hydrochloride (1.00 g, 5.14 mmol) in H₂O (2 mL) was added, then Pd₂(dba)₃ (47 mg, 0.05 mmol) and BINAP (96 mg, 0.15 mmol) were added. The mixture was stirred at 80° C. for 8 h. The mixture was filtered, and the filtrate was concentrated in vacuo. The residue was purified by HPLC to give the desired product (1.2 g).

Alternatively, a mixture of 4-N-Boc-aminomethyl piperidine (132 mg, 0.617 mmol), 4-bromopyridine hydrochloride (100 mg, 0.514 mmol) and K₂CO₃ (142 mg, 1.03 mmol) in DMF (5 mL) was heated at 80° C. overnight. A clean product was also obtained.

The product (120 mg) was dissolved in 4 N HCl in dioxane (3 mL). The solution was stirred at room temperature for 2 h. It was then concentrated in vacuo to give the titled compound (100 mg). MS 192.3 (M+H).

B. Preparation of N-[1-(pyridin-4-yl)piperidin-4-yl]methyl-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (25 mg, 0.077 mmol), 4-[1-(pyridin-4-yl)piperidinyl]methylamine hydrochloride (35 mg, 0.15 mmol) and TEA (0.043 mL, 0.31 mmol) in DMF (3 mL), BOP (51 mg, 0.12 mmol) was added. The mixture was stirred at room temperature for 40 min. It was then concentrated in vacuo. The residue was purified by HPLC to give the titled product (15 mg). MS 504.4 and 506.4 (M+H, Cl pattern)

Example 10

N-[4-(4-methyl-homopiperazinyl)]phenyl-2N-(4-chlorophenylaminocarbonyl)-1,2,3,4-tetrahydroisoquinoline-3-carboxamide

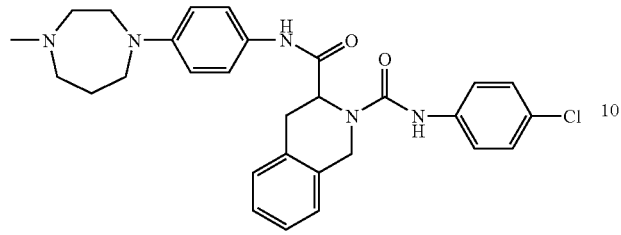

A. Preparation of 4-(4-methyl-homopiperazinyl)phenylamine

A mixture of 1-fluoro-4-nitrobenzene (1.00 g, 7.09 mmol), 1-methylhomopiperazine (0.882 mL, 7.09 mmol) and $K_2CO_3$ (1.96 g, 14.2 mmol) in DMF (8 mL) was heated at 100° C. for 7 h. After cooling to room temperature, $H_2O$ and EtOAc were added. The organic layer was separated, dried over $MgSO_4$, and concentrated in vacuo. The residue was diluted with $H_2O$, and acidified with 4N HCl to pH=1-2. The aqueous solution was then washed with EtOAc, neutralized with 5 N NaOH to pH=9. The aqueous solution was concentrated in vacuo. The product in the residue was taken up in MeOH. The insoluble inorganic salt was filtered off, the filtrate was concentrated in vacuo to give a solid (0.88 g). MS 236.1 (M+H)

A mixture of the solid (0.80 g, 3.4 mmol) and Pd—C (5%, 0.080 g) in MeOH (10 mL) was stirred under balloon H2 overnight. It was then filtered, and the filtrate was concentrated in vacuo to give the desired product as an oil (0.59 g).

B. Preparation of N-[4-(4-methyl-homopiperazinyl)]phenyl-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (265 mg, 0.802 mmol) and 4-(4-methyl-homopiperazinyl)phenylamine (360 mg, 1.76 mmol) in DMF (7 mL), EDC (337 mg, 1.76 mmol) was added. The mixture was stirred at room temperature overnight. It was then concentrated in vacuo. The residue was purified by HPLC to give the titled product (190 mg). MS 518.2 and 520.2 (M+H, Cl pattern)

Example 11

4-(1-methylpiperidin-4-yl)piperazinyl 2N-(4-chlorophenylaminocarbonyl)-1,2,3,4-tetrahydroisoquinoline-3-carboxamide

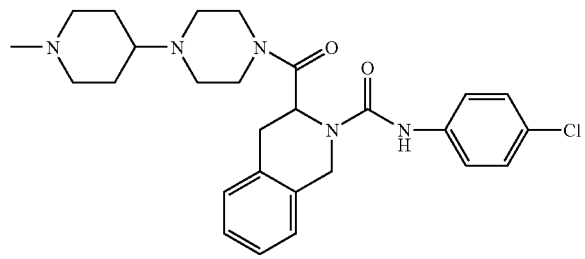

To a solution of 2N-(4-chlorophenylaminocarbonyl)-1,2,3,4-tetrahydroisoquinoline-3-carboxylic acid (50 mg, 0.15 mmol) and 1-(1-methylpiperidin-4-yl)piperazine (55 mg, 0.30 mmol) in DMF (3 mL), EDC (58 mg, 0.30 mmol) was added. The mixture was stirred at room temperature for 1 h. It was then concentrated in vacuo. The residue was purified by HPLC to give the titled product (35 mg). MS 496.4 and 498.4 (M+H, Cl pattern).

Example 12

N-(1-isopropylpiperidin-4-yl)2N-(4-chlorophenylaminocarbonyl)-1,2,3,4-tetrahydroisoquinoline-3-carboxamide

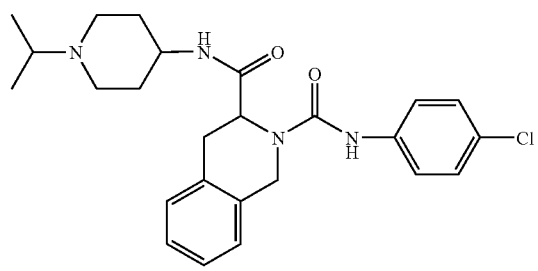

A. Preparation of 1-isopropyl-4-aminopiperidine

To a solution of 4-N-Boc-aminopiperidine (1.50 g, 7.49 mmol) and acetone (2.8 mL, 37.5 mmol) in MeOH (10 mL) and HOAc (0.5 mL), $NaBH_3CN$ (1.89 g, 15.0 mmol) was added. The mixture was stirred at room temperature for 6 h. It was then concentrated in vacuo. The residue was purified by a flash column using $MeOH/CH_2Cl_2/NH_3$ (5/95/1) as eluents to afford an off-white solid (1.5 g). MS 244.4 (M+H)

The solid (1.0 g, 4.1 mmol) was dissolved in 4 N HCl in dioxane (10 mL). The solution was stirred at room temperature for 3 h. It was then concentrated in vacuo to give the desired product as hydrochloride salt (0.71 g).

B. Preparation of N-(1-isopropylpiperidin-4-yl)2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (100 mg, 0.302 mmol), 1-isopropyl-4-aminopiperidine (108 mg, 0.604 mmol) and TEA (0.168 mL, 1.21 mmol) in DMF (4 mL), BOP (174 mg, 0.393 mmol) was added. The reaction mixture was stirred at room temperature for 1 h. It was then concentrated, and the residue was purified by HPLC to give a titled compound as a powder (25 mg). MS 455.2 and 457.2 (M+H, Cl pattern).

Example 13

N-[4-(2-dimethylaminomethyl-imidazol-1-yl)-2-fluorophenyl]-2N-(4-chlorophenylaminocarbonyl)-1,2,3,4-tetrahydroisoquinoline-3-carboxamide

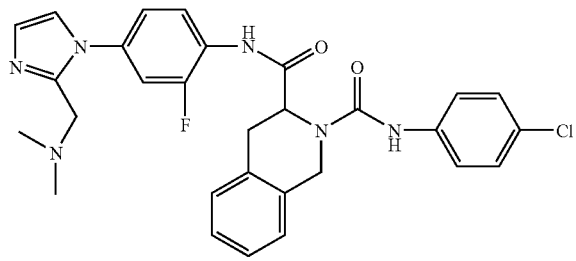

A. Preparation of 4-(2-dimethylaminomethyl-imidazol-1-yl)-2-fluorophenylamine To suspension of 2-imidazolecarboxaldehyde (1.06 g, 11.0 mmol) and dimethylamine (2M in THF, 7 mL, 14 mmol) in MeOH (10 mL) and HOAc (7 mL), NaBH$_3$CN (1.04 g, 16.5 mmol) was added. The reaction mixture was then stirred at room temperature overnight, during which time the suspension became clear. The solution was concentrated in vacuo, and the residue was partitioned between 1N NaOH and nBuOH. The nBuOH solution was separated, concentrated in vacuo to give gum-like residue (0.89 g), which was pure enough for the next reaction. MS 126.1 (M+H)

A suspension of the residue (0.790 g, 6.32 mmol), 2-fluoro-4-iodoaniline (1.24 g, 5.23 mmol), K$_2$CO$_3$ (0.794 g, 5.75 mmol) and 8-hydroxyquinoline (114 mg, 0.786 mmol) in DMSO (20 mL) was degassed with vacuum/Ar cycle (3×), before being charged with CuI (170 mg, 0.895 mmol). The mixture was then heated at 130° C. overnight. EtOAc and 14% NH$_4$OH were added. The organic layer was separated, filtered, dried over Na$_2$SO$_4$, concentrated in vacuo. The residue was purified by HPLC to give an oil, which was then dissolved in EtOAc. The EtOAc solution was washed with sat. NaHCO$_3$ to remove TFA, dried over Na$_2$SO$_4$, concentrated in vacuo to give a solid (0.32 g). MS 235.1 (M+H) and 190.0 (M–Me$_2$N).

B. Preparation of N-[4-(2-dimethylaminomethyl-imidazol-1-yl)-2-fluorophenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (50 mg, 0.15 mmol) and 4-(2-dimethylaminomethyl-imidazol-1-yl)-2-fluorophenylamine (54 mg, 0.23 mmol) in pyridine (3 mL) cooled in an ice-bath, POCl$_3$ (0.028 mL, 0.30 mmol) was added. The reaction mixture was stirred at room temperature overnight. It was then concentrated in vacuo. The residue was purified by HPLC to give the desired product as a powder (15 mg). MS 547.4 and 549.4 (M+H, Cl pattern).

Example 14

N-[4-(3-oxo-morpholin-4-yl)phenyl]-2N-(4-chlorophenylaminocarbonyl)-1,2,3,4-tetrahydroisoquinoline-3-carboxamide

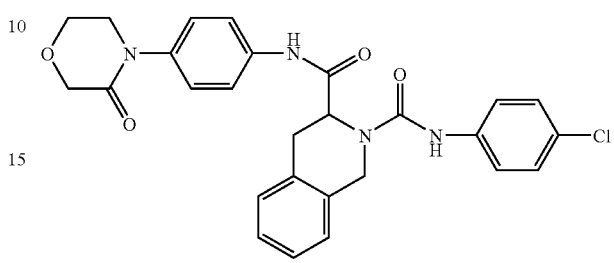

A. Preparation of 3-morpholinone

NaH (60%, 3.2 g, 80 mmol) in a flask was washed with hexane. To the flask cooled in an ice-bath, a solution of ethanolamine (4.4 mL, 73 mmol) in dioxane (40 mL) was added. The mixture was heated at reflux for 10 min until no H$_2$ gas evolved. The thick slurry was then cooled in an ice-bath, and a solution of ethyl chloroacetate (8.9 g, 73 mmol) in dioxane (15 mL) was added. The reaction mixture was heated at reflux for 1 h. It was then filtered. The filtrate was concentrated in vacuo to give an oil, which was purified by a short flash column, eluted with EtOAc/MeOH (95/5) to give a white solid (1.9 g).

B. Preparation of 4-(3-oxo-morpholin-4-yl)phenylamine

To a blue solution of 3-morpholinone (250 mg, 2.48 mmol), 4-iodoaniline (650 mg, 2.97 mmol), CuI (47 mg, 0.25 mmol) and N,N'-dimethylethylenediamine (0.040 mL, 0.372 mmol) in dioxane (5 mL) in a pressure bottle, K$_2$CO$_3$ (683 mg, 4.95 mmol) was added. The mixture was heated at 110° C. overnight. After being cooled to room temperature, the crude dark solution was loaded to two preparative TLC plates, eluted with EtOAc/MeOH (95/5) to give the desired product as off-white solid (240 mg). MS 193.1 (M+H).

C. Preparation of N-[4-(3-oxo-morpholin-4-yl)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (68 mg, 0.21 mmol) and 4-(3-oxo-morpholin-4-yl)phenylamine (40 mg, 0.21 mmol) in DMF (5 mL), EDC (80 mg, 0.42 mmol) was added. The reaction mixture was stirred at room temperature overnight. It was then concentrated in vacuo. The residue was purified by HPLC to give the titled compound as a white powder (66 mg). MS 505.2 and 507.2 (M+H, Cl pattern).

Example 15

N-[4-(3-thiazolidinylcarbonyl)phenyl]-2N-(4-chlorophenylaminocarbonyl)-1,2,3,4-tetrahydroisoquinoline-3-carboxamide

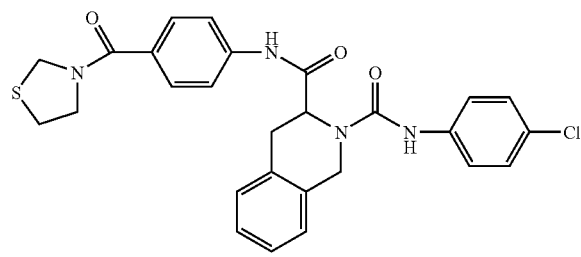

A. Preparation of 4-(3-thiazolidinylcarbonyl)phenylamine

To a suspension of 4-nitrobenzoic acid (1.00 g, 5.99 mmol) in $CH_2Cl_2$ (15 mL) and DMF (4 drops) at room temperature, oxalyl chloride (0.628 mL, 7.19 mmol) was added. The reaction mixture was then stirred for 4 h, during which time the suspension became clear. After being concentrated in vacuo, the residue was dissolved in $CH_2Cl_2$ (15 mL). To the solution, thiazolidine (0.471 mL, 5.99 mmol) and TEA (1.67 mL, 12.0 mmol) were added. It was stirred overnight. The $CH_2Cl_2$ solution was washed with 1N HCl, $H_2O$, and sat. $NaHCO_3$, then dried over $Na_2SO_4$, concentrated in vacuo to give an oil (1.12 g).

A mixture of the oil (1.12 g, 4.71 mmol) and Pd—C (5%, 180 mg) in $CH_2Cl_2$ (5 mL) and MeOH (10 mL) containing TFA (5 drops) was hydrogenated at 45 psi on a Parr shaker for 3 days. The mixture was then filtered, and the filtrate was concentrated in vacuo. One half of the residue was purified by HPLC to give an oil (151 mg). MS 209.0 (M+H) and 231.0 (M+Na).

B. Preparation of N-[4-(3-thiazolidinylcarbonyl)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (50 mg, 0.15 mmol) and 4-(3-thiazolidinylcarbonyl)phenylamine (30 mg, 0.14 mmol) in DMF (2 mL), EDC (54 mg, 0.28 mmol) was added. The reaction mixture was stirred at room temperature overnight. It was then concentrated in vacuo. The residue was purified by HPLC to give the titled compound as a white powder (32 mg). MS 521.0 and 523.0 (M+H, Cl pattern).

Example 16

N-[4-(3-oxazolidinylcarbonyl)phenyl]-2N-(4-chlorophenylaminocarbonyl)-1,2,3,4-tetrahydroisoquinoline-3-carboxamide

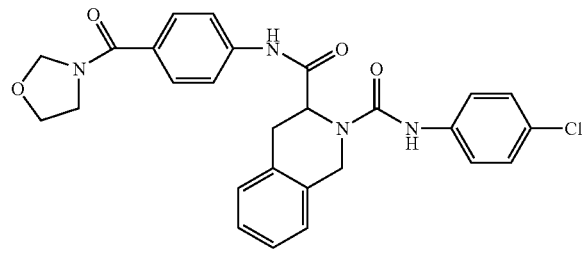

A. Preparation of 4-(3-oxazolidinylcarbonyl)phenylamine

To a suspension of 4-nitrobenzoic acid (2.00 g, 12.0 mmol) in $CH_2Cl_2$ (30 mL) and DMF (5 drops) at room temperature, oxalyl chloride (1.25 mL, 14.3 mmol) was added. It was then stirred overnight. The solution was concentrated in vacuo.

To a solution of ethanolamine (0.866 mL, 14.3 mmol) and TEA (3.9 mL, 28.0 mmol) in $CH_2Cl_2$ (15 mL) at room temperature, a solution of the acid chloride (12 mmol) in $CH_2Cl_2$ (8 mL) was added. After being stirred for 1 h, the reaction mixture was concentrated in vacuo. One third of the residue was purified by HPLC to give a white solid (0.62 g). MS 211.0 (M+H).

A mixture of the solid (230 mg, 1.10 mmol), dimethoxymethane (0.58 mL, 6.6 mmol) and $P_2O_5$ (600 mg, 4.23 mmol) in $CHCl_3$ (5 mL) was heated at 70° C. for 4 h. $CHCl_3$ and 1N HCl were added. The $CHCl_3$ solution was separated, washed with brine, dried over $Na_2SO_4$, concentrated in vacuo to give an oil (138 mg). MS 223.0 (M+H).

A mixture of the oil (138 mg) and Pd—C (5%, 33 mg) in MeOH (5 mL) was stirred under balloon $H_2$ overnight. It was then filtered, and the filtrate was concentrated in vacuo to give titled compound as an oil (105 mg). MS 193.0 (M+H).

B. Preparation of N-[4-(3-oxazolidinylcarbonyl)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (50 mg, 0.15 mmol) and 4-(3-oxazolidinylcarbonyl)phenylamine (25 mg, 0.13 mmol) in DMF (3 mL), EDC (75 mg, 0.39 mmol) was added. The reaction mixture was stirred at room temperature overnight. It was then concentrated in vacuo. The residue was purified by HPLC to give the titled compound as a white powder (26 mg). MS 505.2 and 507.2 (M+H, Cl pattern).

Example 17

N-[4-(N-methyl-N-pyridin-4-yl-amino)phenyl]-2N-(4-chlorophenylaminocarbonyl)-1,2,3,4-tetrahydroisoquinoline-3-carboxamide

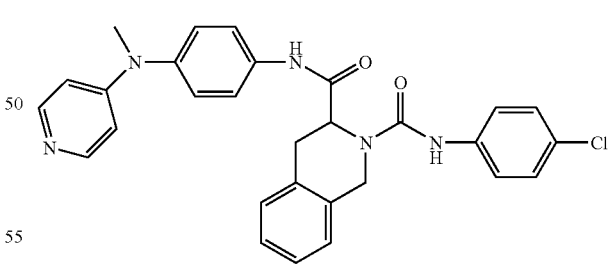

A. Preparation of 4-(N-methyl-N-pyridin-4-yl-amino)phenylamine

A mixture of 4-methylaminopyridine (427 mg, 3.95 mmol), 1-fluoro-nitrobenzene (0.472 mL, 4.45 mmol) and $Cs_2CO_3$ (2.0 g, 6.1 mmol) in DMF (9 mL) was heated at 80° C. for 3 h. It was then filtered, and the filtrate was concentrated in vacuo. The residue was purified by HPLC to give an oil (230 mg). MS 230.0 (M+H).

A mixture of the oil (110 mg, 0.480 mmol) and Pd—C (5%, 35 mg) in MeOH (5 mL) was stirred under balloon H$_2$ for 4 h. It was then filtered, and the filtrate was concentrated in vacuo to give the titled compound (94 mg). MS 200.2 (M+H).

B. Preparation of N-[4-(N-methyl-N-pyridin-4-yl-amino)phenyl]-2N-(4-chlorophenylaminocarbonyl)-1,2,3,4-tetrahydroisoquinoline-3-carboxamide To a solution of 2N-(4-chlorophenylaminocarbonyl)-1,2,3,4-tetrahydroisoquinoline-3-carboxylic acid (63 mg, 0.19 mmol) and 4-(N-methyl-N-pyridin-4-yl-amino)phenylamine (47 mg, 0.24 mmol) in DMF (3 mL), EDC (80 mg, 0.42 mmol) was added. The reaction mixture was stirred at room temperature overnight. It was then concentrated in vacuo. The residue was purified by HPLC to give the titled compound as a white powder (25 mg). MS 512.2 and 514.2 (M+H, Cl pattern).

Example 18

N-[4-(1-methyl-4,5-dihydro-1H-imidazol-2-yl)phenyl]-2N-(4-chlorophenylaminocarbonyl)-5-methyl-1,2,3,4-tetrahydroisoquinoline-3-carboxamide

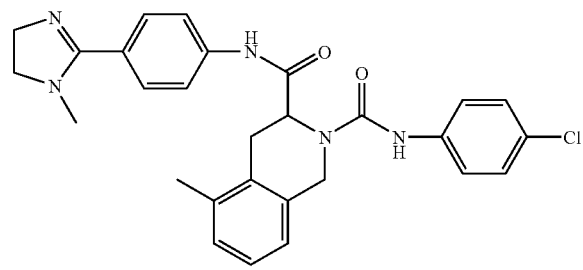

A. Preparation of 2N-(4-chlorophenylaminocarbonyl)-5-methyl-1,2,3,4-tetrahydroisoquinoline-3-carboxylic acid To a solution of D,L-5-methyl-1,2,3,4-tetrahydroisoquinoline-3-carboxylic acid (700 mg, 3.66 mmol) in 1N aq. NaOH (8 mL), a solution of 4-chlorophenylisocyanate (900 mg, 5.86 mmol) in dioxane (8 mL) was added. The mixture was stirred at room temperature overnight. It was then washed with Et$_2$O (2×). The aqueous layer was separated, acidified with 4N HCl to pH 1 to 2. The product was extracted with EtOAc. The EtOAc solution was dried over Na$_2$SO$_4$, concentrated in vacuo to give a solid (1.30 g), which was sufficiently pure to be used in the next reaction. MS 345.1 and 347.1 (M+H, Cl pattern).

B. Preparation of N-[4-(1-methyl-4,5-dihydro-1H-imidazol-2-yl)phenyl]-2N-(4-chlorophenylaminocarbonyl)-5-methyl-1,2,3,4-tetrahydroisoquinoline-3-carboxamide To a solution of 2N-(4-chlorophenylaminocarbonyl)-5-methyl-1,2,3,4-tetrahydroisoquinoline-3-carboxylic acid (50 mg, 0.15 mmol) and 4-(1-Methyl-4,5-dihydro-1H-imidazol-2-yl)-phenylamine (51 mg, 0.29 mmol) in DMF (3 mL) and H$_2$O (1 mL) at room temperature, EDC (111 mg, 0.58 mmol) was added. The mixture was stirred at room temperature overnight. It was concentrated in vacuo. The residue was purified by HPLC to give the titled compound as a white powder (50 mg). MS 502.2 and 504.2 (M+H, Cl pattern).

Example 19

N-[4-(pyrrolidinylimino)phenyl]-2N-(4-chlorophenylaminocarbonyl)-5-methyl-1,2,3,4-tetrahydroisoquinoline-3-carboxamide

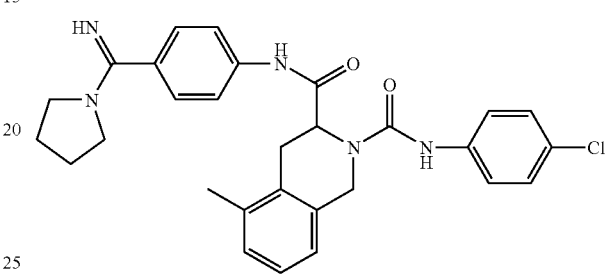

To a solution of 2N-(4-chlorophenylaminocarbonyl)-5-methyl-1,2,3,4-tetrahydroisoquinoline-3-carboxylic acid (60 mg, 0.17 mmol) and 4-(pyrrolidinylimino)phenylamine (66 mg, 0.35 mmol) in DMF (3 mL) and H$_2$O (1 mL) at room temperature, EDC (133 mg, 0.70 mmol) was added. The mixture was stirred at room temperature for 2 h. It was concentrated in vacuo. The residue was purified by HPLC to give the titled compound as a powder (83 mg). MS 516.2 and 518.2 (M+H, Cl pattern).

Example 20

N-[4-(dimethylaminoimino)phenyl]-2N-(4-chlorophenylaminocarbonyl)-5-methyl-1,2,3,4-tetrahydroisoquinoline-3-carboxamide

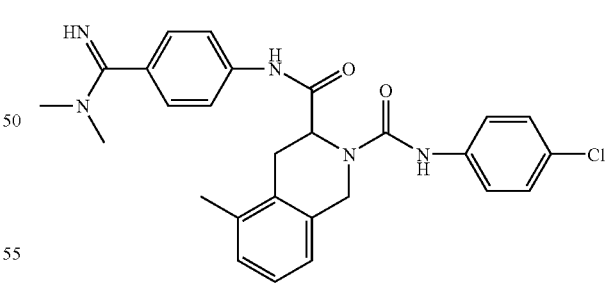

To a solution of 2N-(4-chlorophenylaminocarbonyl)-5-methyl-1,2,3,4-tetrahydroisoquinoline-3-carboxylic acid (80 mg, 0.23 mmol) and 4-(dimethylaminoimino)phenyl (76 mg, 0.46 mmol) in DMF (4 mL) and H$_2$O (1 mL) at room temperature, EDC (178 mg, 0.93 mmol) was added. The mixture was stirred at room temperature for 1 h. It was concentrated in vacuo. The residue was purified by HPLC to give the titled compound as a powder (90 mg). MS 490.2 and 492.1 (M+H, Cl pattern).

Example 21

Preparation of (3S)-N-[4-(1-methyl-4,5-dihydro-1H-imidazol-2-yl)phenyl]-2N-(4-chlorophenylaminocarbonyl)-6,7-dimethoxy-1,2,3,4-tetrahydroisoquinoline-3-carboxamide

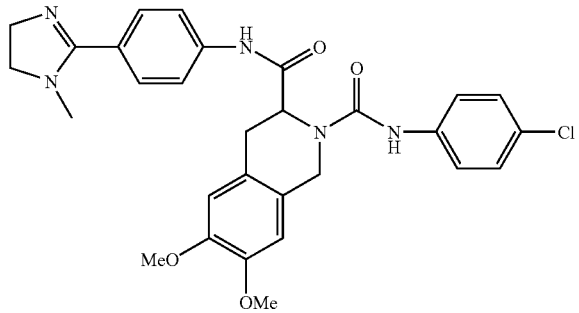

A. Preparation of (3S)-2N-(4-chlorophenylaminocarbonyl)-6,7-dimethoxy-1,2,3,4-tetrahydroisoquinoline-3-carboxylic acid To a solution of (S) 6,7-dimethoxy-1,2,3,4-tetrahydroisoquinoline-3-carboxylic acid (1.00 g, 2.44 mmol) in 1N aq. NaOH (10 mL), a solution of 4-chlorophenylisocyanate (563 mg, 3.66 mmol) in dioxane (8 mL) was added. The mixture was stirred at room temperature overnight. More 4-chlorophenylisocyanate (600 mg, 3.91 mmol) in dioxane (5 mL) was added. It was stirred for another day. It was then washed with Et$_2$O (2×). The aqueous layer was separated, acidified with 4N HCl to pH 1 to 2. The product was extracted with EtOAc. The EtOAc solution was dried over Na$_2$SO$_4$, concentrated in vacuo to give a solid (1.50 g), which was sufficiently pure to be used in the next reaction. MS 391.1 and 393.1 (M+H, Cl pattern).

B. Preparation of (3S)-N-[4-(1-methyl-4,5-dihydro-1H-imidazol-2-yl)phenyl]-2N-(4-chlorophenylaminocarbonyl)-6,7-dimethoxy-1,2,3,4-tetrahydroisoquinoline-3-carboxamide To a solution of (3S)-2N-(4-chlorophenylaminocarbonyl)-6,7-dimethoxy-1,2,3,4-tetrahydroisoquinoline-3-carboxylic acid (25 mg, 0.064 mmol) and 4-(1-Methyl-4,5-dihydro-1H-imidazol-2-yl)-phenylamine (23 mg, 0.13 mmol) in DMF (2 mL) and H$_2$O (0.5 mL) at room temperature, EDC (49 mg, 0.26 mmol) was added. The mixture was stirred at room for 2 h. It was concentrated in vacuo. The residue was purified by HPLC to give the titled compound as a white powder (20 mg). MS 548.2 and 550.2 (M+H, Cl pattern).

Example 22

(3S)-N-[4-(pyrrolidinylimino)phenyl]-2N-(4-chlorophenylaminocarbonyl)-6,7-dimethoxy-1,2,3,4-tetrahydroisoquinoline-3-carboxamide

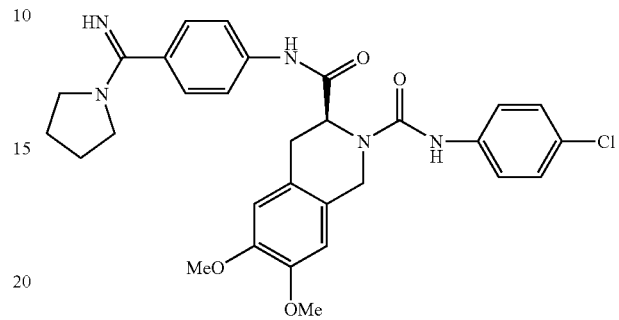

To a solution of (3S)-2N-(4-chlorophenylaminocarbonyl)-6,7-dimethoxy-1,2,3,4-tetrahydroisoquinoline-3-carboxylic acid (100 mg, 0.26 mmol) and 4-(pyrrolidinylimino)phenylamine (97 mg, 0.51 mmol) in DMF (4 mL) and H$_2$O (1 mL) at room temperature, EDC (196 mg, 1.02 mmol) was added. The mixture was stirred at room temperature for 2 h. It was concentrated in vacuo. The residue was purified by HPLC to give the titled compound as a powder (118 mg). MS 562.2 and 564.2 (M+H, Cl pattern).

Example 23

(3S)-N-[4-(dimethylaminoimino)phenyl]-2N-(4-chlorophenylaminocarbonyl)-6,7-diemthoxy-1,2,3,4-tetrahydroisoquinoline-3-carboxamide

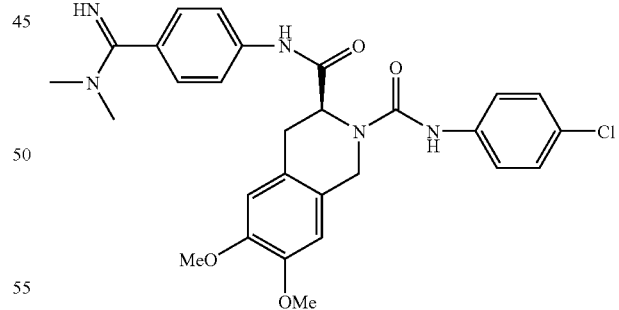

To a solution of (3S)-2N-(4-chlorophenylaminocarbonyl)-6,7-dimethoxy-1,2,3,4-tetrahydroisoquinoline-3-carboxylic acid (30 mg, 0.077 mmol) and 4-(dimethylaminoimino)phenyl (25 mg, 0.15 mmol) in DMF (3 mL) and H$_2$O (1 mL) at room temperature, EDC (59 mg, 0.31 mmol) was added. The mixture was stirred at room temperature for 2 h. It was concentrated in vacuo. The residue was purified by HPLC to give the titled compound as a powder (15 mg). MS 536.2 and 538.2 (M+H, Cl pattern).

Example 24

N-[4-(1-methyl-4,5-dihydro-1H-imidazol-2-yl)phenyl]-2N-(4-chlorophenylaminocarbonyl)-6-hydroxy-1,2,3,4-tetrahydroisoquinoline-3-carboxamide

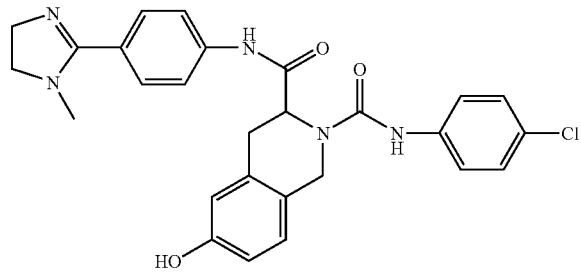

A. Preparation of 2N-(4-chlorophenylaminocarbonyl)-6-hydroxy-1,2,3,4-tetrahydroisoquinoline-3-carboxylic acid To a suspension of (D,L) 6-hydroxy-1,2,3,4-tetrahydroisoquinoline-3-carboxylic acid (500 mg, 2.59 mmol) in DMF (12 mL), 4-chlorophenyl isocyanate (400 mg, 2.60 mmol) was added. The reaction mixture was stirred at room temperature overnight, and the suspension became clear solution. It was then concentrated in vacuo. The residue was dissolved in $CH_2Cl_2$, and the product was extracted with 5N NaOH. The alkaline solution was then separated, acidified with 4N HCl to pH 2-3. The cloudy mixture was extracted with EtOAc. The EtOAc solution was dried over $Na_2SO_4$, concentrated in vacuo to give the titled compound as a solid (841 mg), which was pure enough for the next reaction.

B. Preparation of N-[4-(1-methyl-4,5-dihydro-1H-imidazol-2-yl)phenyl]-2N-(4-chlorophenylaminocarbonyl)-6-hydroxy-1,2,3,4-tetrahydroisoquinoline-3-carboxamide To a solution of 2N-(4-chlorophenylaminocarbonyl)-6-hydroxy-1,2,3,4-tetrahydroisoquinoline-3-carboxylic acid (230 mg, 0.664 mmol) and 4-(1-Methyl-4,5-dihydro-1H-imidazol-2-yl)-phenylamine (232 mg, 1.33 mmol) in DMF (10 mL) and $H_2O$ (1 mL) at room temperature, EDC (260 mg, 1.35 mmol) was added. The mixture was stirred at room temperature overnight. It was concentrated in vacuo. The residue was purified by HPLC to give the titled compound as a powder (35 mg). MS 504.3 and 506.3 (M+H, Cl pattern).

Example 25

N-[4-(1-methyl-4,5-dihydro-1H-imidazol-2-yl)phenyl]-5N-(4-chlorophenylaminocarbonyl)-4,5,6,7-tetrahydro-thieno[3,2-c]pyridine-6-carboxamide

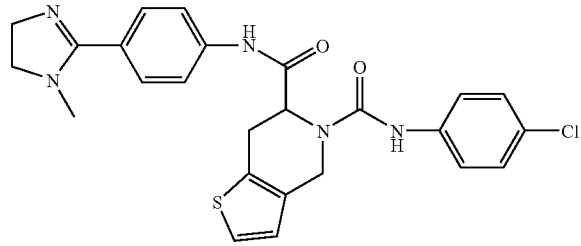

A. Preparation of 4,5,6,7-tetrahydro-thieno[3,2-c]pyridine-6-carboxylic acid A suspension of (D,L) 3-(2-thienyl)-alanine (302 mg, 1.77 mmol) in 37% aq. HCHO (4 mL) was heated at 60° C. for 2 h. The suspension became clear. It was concentrated in vacuo to give the titled compound (323 mg), which was used in the next step without further purification. MS 184.3 (M+H)

B. Preparation of 5N-(4-chlorophenylaminocarbonyl)-4,5,6,7-tetrahydro-thieno[3,2-c]pyridine-6-carboxylic acid To a solution of the crude sample 4,5,6,7-tetrahydro-thieno[3,2-c]pyridine-6-carboxylic acid (323 mg, 1.77 mmol) in DMF (10 mL), 4-chlorophenyl isocyanate (336 mg, 2.19 mmol) was added. It was stirred at room temperature overnight. After being concentrated in vacuo, the residue was purified by HPLC to give the desired product as a powder (130 mg). MS 337.3 and 339.3 (M+H, Cl pattern)

C. Preparation of N-[4-(1-methyl-4,5-dihydro-1H-imidazol-2-yl)phenyl]-5N-(4-chlorophenylaminocarbonyl)-4,5,6,7-tetrahydro-thieno[3,2-c]pyridine-6-carboxamide To a solution of 5N-(4-chlorophenylaminocarbonyl)-4,5,6,7-tetrahydro-thieno[3,2-c]pyridine-6-carboxylic acid (40 mg, 0.12 mmol) and 4-(1-Methyl-4,5-dihydro-1H-imidazol-2-yl)-phenylamine (42 mg, 0.24 mmol) in DMF (3 mL) and $H_2O$ (0.5 mL) at room temperature, EDC (68 mg, 0.35 mmol) was added. The mixture was stirred at room temperature overnight. It was concentrated in vacuo. The residue was purified by HPLC to give the titled compound as a powder (25 mg). MS 494.3 and 496.3 (M+H, Cl pattern).

Example 26

N-[4-(dimethylaminoimino)phenyl]-5N-(4-chlorophenylaminocarbonyl)-4,5,6,7-tetrahydro-thieno[3,2-c]pyridine-6-carboxamide

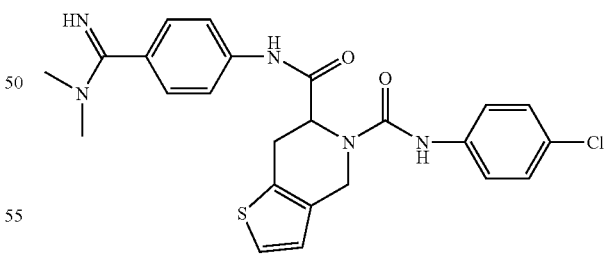

To a solution of 5N-(4-chlorophenylaminocarbonyl)-4,5,6,7-tetrahydro-thieno[3,2-c]pyridine-6-carboxylic acid (42 mg, 0.12 mmol) and 4-(dimethylaminoimino)phenylamine (42 mg, 0.26 mmol) in DMF (3 mL) and $H_2O$ (0.5 mL) at room temperature, EDC (72 mg, 0.38 mmol) was added. The mixture was stirred at room temperature overnight. It was concentrated in vacuo. The residue was purified by HPLC to give the titled compound as a powder (26 mg). MS 482.3 and 484.4 (M+H, Cl pattern).

Example 27

N-[4-(4-methyl-homopiperazinyl)]phenyl-5N-(4-chlorophenylaminocarbonyl)-4,5,6,7-tetrahydro-thieno[3,2-c]pyridine-6-carboxamide

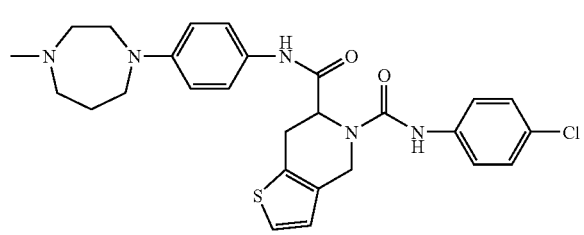

To a solution of 5N-(4-chlorophenylaminocarbonyl)-4,5,6,7-tetrahydro-thieno[3,2-c]pyridine-6-carboxylic acid (47 mg, 0.14 mmol) and 4-(4-methyl-homopiperazinyl)phenylamine (67 mg, 0.28 mmol) in DMF (3 mL) and H$_2$O (0.5 mL) at room temperature, EDC (80 mg, 0.42 mmol) was added. The mixture was stirred at room temperature overnight. It was concentrated in vacuo. The residue was purified by HPLC to give the titled compound as a powder (12 mg). MS 524.4 and 526.4 (M+H, Cl pattern).

Example 28

Preparation of N-[4-(1-methyl-4,5-dihydro-1H-imidazol-2-yl)phenyl]-2N-(4-chlorophenylaminocarbonyl)-2,3-dihydro-1H-isoindole-1-carboxamide

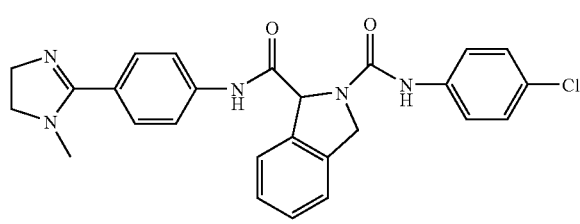

A. Preparation of 2N-(4-chlorophenylaminocarbonyl)-2,3-dihydro-1H-isoindole-1-carboxylic acid To a solution of (D,L) 2,3-dihydro-1H-isoindole-1-carboxylic acid (372 mg, 2.28 mmol) in 3N aq. NaOH (10 mL), a solution of 4-chlorophenylisocyanate (530 mg, 3.66 mmol) in dioxane (6 mL) was added. The mixture was stirred at room temperature overnight. It was then washed with Et$_2$O (2×). The aqueous layer was separated, acidified with 4N HCl to pH 1 to 2. The product was extracted with EtOAc. The EtOAc solution was dried over Na$_2$SO$_4$, concentrated in vacuo to give the titled compound as a solid (550 mg), which was sufficiently pure to be used in the next reaction. MS 317.0 and 319.0 (M+H, Cl pattern).

B. Preparation of N-[4-(1-methyl-4,5-dihydro-1H-imidazol-2-yl)phenyl]-2N-(4-chlorophenylaminocarbonyl)-2,3-dihydro-1H-isoindole-1-carboxamide To a solution of 2N-(4-chlorophenylaminocarbonyl)-2,3-dihydro-1H-isoindole-1-carboxylic acid (62 mg, 0.20 mmol) and 4-(1-Methyl-4,5-dihydro-1H-imidazol-2-yl)-phenylamine (70 mg, 0.40 mmol) in DMF (3 mL) and H$_2$O (1 mL) at room temperature, EDC (100 mg, 0.52 mmol) was added. The mixture was stirred at room temperature for 2 h. It was concentrated in vacuo. The residue was purified by HPLC to give the titled compound as a powder (11 mg). MS 474.4 and 476.4 (M+H, Cl pattern).

Example 29

N-[4-(1N-oxo-pyridin-2-yl)phenyl]-2N-(4-chlorophenylaminocarbonyl)-2,3-dihydro-1H-isoindole-1-carboxamide

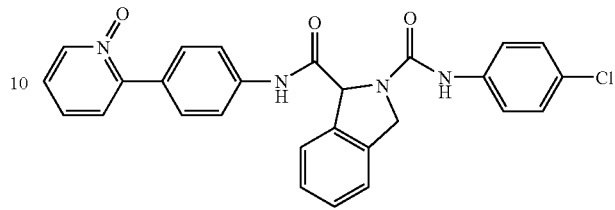

To a solution of 2N-(4-chlorophenylaminocarbonyl)-2,3-dihydro-1H-isoindole-1-carboxylic acid (62 mg, 0.20 mmol) and 4-(1N-oxo-pyridin-2-yl)phenylamine (65 mg, 0.29 mmol) in DMF (3 mL) and H$_2$O (1 mL) at room temperature, EDC (300 mg, 1.56 mmol) was added. The mixture was stirred at room temperature overnight. It was concentrated in vacuo. The residue was purified by HPLC to give the titled compound as a white powder (21 mg). MS 485.5 and 487.5 (M+H, Cl pattern).

Example 30

N-[4-(4-methyl-homopiperazinyl)phenyl]-2N-(4-chlorophenylaminocarbonyl)-2,3-dihydro-1H-isoindole-1-carboxamide

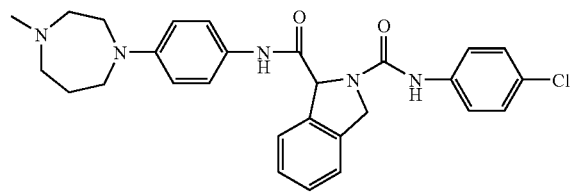

To a solution of 2N-(4-chlorophenylaminocarbonyl)-2,3-dihydro-1H-isoindole-1-carboxylic acid (50 mg, 0.16 mmol) and 1-methyl-homopiperazine (46 mg, 0.22 mmol) in pyridine (3 mL) cooled in an ice-bath, POCl$_3$ (0.042 mL, 0.46 mmol) was added dropwise. After being stirred at room temperature for 2 h, the mixture was concentrated in vacuo. The residue was purified by HPLC to give the titled compound as a powder (10 mg). MS 504.2 and 506.2 (M+H, Cl pattern).

Example 31

N-[4-(3-oxo-morpholin-4-yl)phenyl]-2N-(4-chlorophenylaminocarbonyl)-2,3-dihydro-1H-isoindole-1-carboxamide

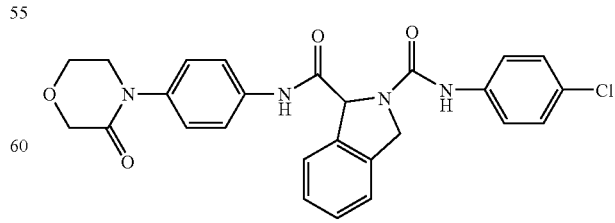

To a solution of 2N-(4-chlorophenylaminocarbonyl)-2,3-dihydro-1H-isoindole-1-carboxylic acid (53 mg, 0.17 mmol) and 4-(3-oxo-morpholin-4-yl)phenylamine (32 mg, 0.17 mmol) in pyridine (3 mL) cooled in an ice-bath, POCl$_3$ (0.040 mL, 0.44 mmol) was added dropwise. After being stirred at room temperature for 1 h, the mixture was concentrated in vacuo. The residue was purified by HPLC to give the titled compound as a powder (5 mg). MS 491.0 and 493.0 (M+H, Cl pattern).

Example 32

N-[4-(1N-oxo-pyridin-2-yl)phenyl]-1N-(4-chlorophenylaminocarbonyl)-indoline-2-carboxamide

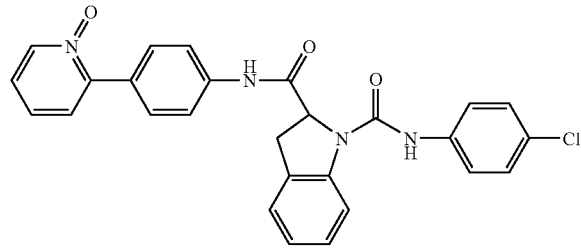

A. Preparation of 1N-(4-chlorophenylaminocarbonyl)-indoline-2-carboxylic acid To a solution of (D,L) indoline-2-carboxylic acid (548 mg, 3.36 mmol) in 1N aq. NaOH (8 mL), a solution of 4-chlorophenylisocyanate (728 mg, 4.74 mmol) in dioxane (8 mL) was added. The mixture was stirred at room temperature overnight. It was then washed with Et$_2$O (2×). The aqueous layer was separated, acidified with 4N HCl to pH 1 to 2. The product was extracted with EtOAc. The EtOAc solution was dried over Na$_2$SO$_4$, concentrated in vacuo. The residue was purified by HPLC to give the desired product as a powder (325 mg).

B. Preparation of N-[4-(1N-oxo-pyridin-2-yl)phenyl]-1N-(4-chlorophenylaminocarbonyl)-indoline-2-carboxamide To a solution of 1N-(4-chlorophenylaminocarbonyl)-indoline-2-carboxylic acid (60 mg, 0.19 mmol) and 4-(1N-oxo-pyridin-2-yl)phenylamine (51 mg, 0.23 mmol) in pyridine (5 mL) cooled in an ice-bath, POCl$_3$ (0.060 mL, 0.66 mmol) was added. The mixture was stirred at 0° C. for 20 min. It was concentrated in vacuo. The residue was purified by HPLC to give the titled compound as a white powder (11 mg). MS 485.5 and 487.5 (M+H, Cl pattern).

Example 33

Preparation of (3R) N-[4-(4-methyl-homopiperazinyl)]phenyl-2N-(4-chlorophenylaminocarbonyl)-1,2,3,4-tetrahydroisoquinoline-3-carboxamide

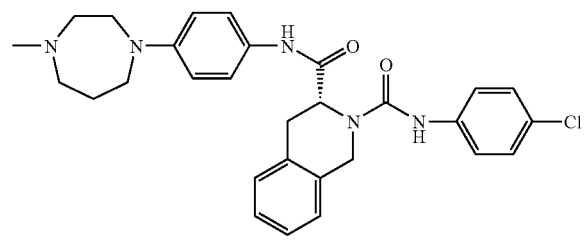

The compound was prepared analogously to the procedure described in Example 10, using (3R) 1,2,3,4-tetrahydroisoquinoline-3-carboxylic acid in the place of the racemic isomers. MS 518.2 and 520.2 (M+H, Cl pattern).

Example 34

Preparation of (3S)N-[4-(4-methyl-homopiperazinyl)]phenyl-2N-(4-chlorophenylaminocarbonyl)-1,2,3,4-tetrahydroisoquinoline-3-carboxamide

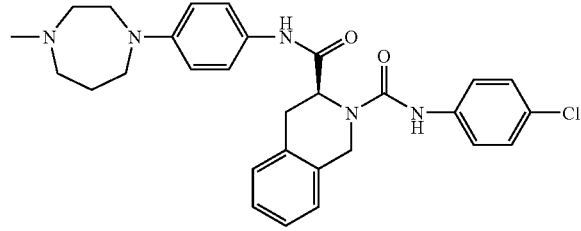

The compound was prepared analogously to the procedure described in Example 10, using (3S)1,2,3,4-tetrahydroisoquinoline-3-carboxylic acid in the place of the racemic isomers. MS 518.2 and 520.2 (M+H, Cl pattern).

Example 35

Preparation of (3R) N-[4-(4-methyl-homopiperazinyl)-2-fluorophenyl]-2N-(4-chlorophenylaminocarbonyl)-1,2,3,4-tetrahydroisoquinoline-3-carboxamide

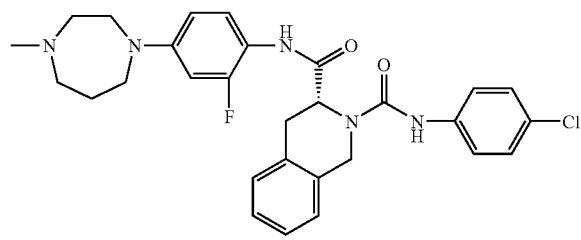

A. Preparation of 4-(4-methyl-homopiperazinyl)-2-fluorophenylamine

A mixture of 2-fluoro-4-iodoaniline (474 mg, 2.00 mmol), 1-methylhomopiperazine (0.372 mL, 3.00 mmol), ethylene glycol (0.222 mL, 4.00 mmol) and K$_3$PO$_4$ (848 mg, 4.00 mmol) in isopropanol (2 mL) was degassed with Ar before being charged with CuI (76 mg, 0.40 mmol). The mixture in a sealed tube was heated at 85° C. for three days. One fifth of the reaction mixture was applied to a silica gel prep TLC plate, which was then developed in CH$_2$Cl$_2$/MeOH/NH$_4$OH (85/15/0.5). The area containing the desired product was scraped out, and the product was extracted out with CH$_2$Cl$_2$/MeOH (2/1) to give a solid (54 mg).

B. Preparation of (3R) N-[4-(4-methyl-homopiperazinyl)-2-fluorophenyl]-2N-(4-chlorophenylaminocarbonyl)-1,2,3,4-tetrahydroisoquinoline-3-carboxamide The titled compound was prepared analogously to the procedure described in step B of Example 10, using 4-(4-methylhomopiperazinyl)-2-fluorophenylamine in the place of 4-(4-methyl-homopiperazinyl)phenylamine. MS 536.2 and 538.3 (M+H, Cl pattern).

Example 36

Preparation of (3R) N-[4-(2-pyridon-1-yl)phenyl]-2N-(4-chlorophenylaminocarbonyl)-1,2,3,4-tetrahydroisoquinoline-3-carboxamide

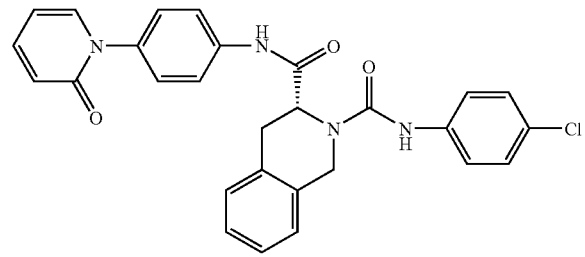

A. Preparation of 4-(2-pyridon-1-yl)phenylamine

A mixture of 4-iodoaniline (1.00 g, 4.57 mmol), 2-hydroxypyridine (0.477 g, 5.02 mmol), 8-hydroxyquinoline (0.110 g, 0.759 mmol) and $K_2CO_3$ (0.945 g, 6.85 mmol) in DMSO (10 mL) was degassed with Ar before being charged with CuI (0.145 g, 0.763 mmol). The mixture in a sealed tube was then heated at 130° C. overnight. Water and n-BuOH were added. The mixture was filtered. The n-BuOH phase was separated, and concentrated in vacuo to give a solid (0.666 g), which was pure enough for subsequent reactions. MS 187.3 (M+H).

B. Preparation of (3R) N-[4-(2-pyridon-1-yl)phenyl]-2N-(4-chlorophenylaminocarbonyl)-1,2,3,4-tetrahydroisoquinoline-3-carboxamide The titled compound was prepared analogously to the procedure described in step C of Example 14, using 4-(2-pyridon-1-yl)phenylamine in the place of 4-(3-oxo-morpholin-4-yl)phenylamine. MS 497.0 and 499.0 (M-H, Cl pattern).

Example 37

Preparation of (3S)N-[4-(2-pyridon-1-yl)phenyl]-2N-(4-chlorophenylaminocarbonyl)-1,2,3,4-tetrahydroisoquinoline-3-carboxamide

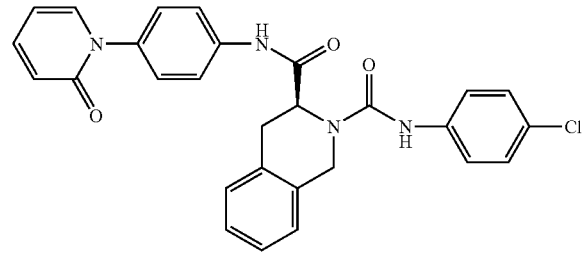

The titled compound was prepared analogously to the procedure described in Example 36, using (3S)2N-(4-chlorophenylaminocarbonyl)-1,2,3,4-tetrahydroisoquinoline-3-carboxylic acid in the place of its (3R) isomer. MS 497.0 and 499.0 (M-H, Cl pattern).

Example 38

Preparation of (3R) N-[4-(2-pyridon-1-yl)-2-fluorophenyl]-2N-(4-chlorophenylaminocarbonyl)-1,2,3,4-tetrahydroisoquinoline-3-carboxamide

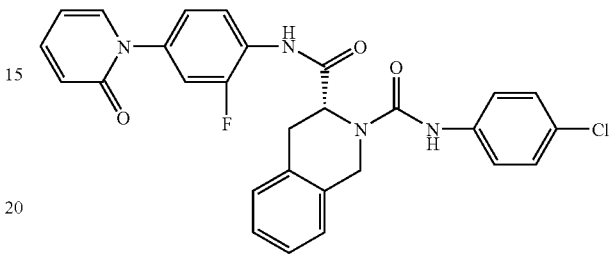

A. Preparation of 4-(2-pyridon-1-yl)-2-fluorophenylamine

A mixture of 2-fluoro-4-iodoaniline (1.08 g, 4.56 mmol), 2-hydroxypyridine (0.477 g, 5.02 mmol), 8-hydroxyquinoline (0.110 g, 0.759 mmol) and $K_2CO_3$ (0.945 g, 6.85 mmol) in DMSO (10 mL) was degassed with Ar before being charged with CuI (0.145 g, 0.763 mmol). The mixture in a sealed tube was then heated at 130° C. overnight. Water and n-BuOH were added. The mixture was filtered. The n-BuOH phase was separated, and concentrated in vacuo to give a solid (0.902 g), which was pure enough for subsequent reactions. MS 205.2 (M+H).

B. Preparation of (3R) N-[4-(2-pyridon-1-yl)-2-fluorophenyl]-2N-(4-chlorophenylaminocarbonyl)-1,2,3,4-tetrahydroisoquinoline-3-carboxamide The titled compound was prepared analogously to the procedure described in step B of Example 36, using 4-(2-pyridon-1-yl)-2-fluorophenylamine in the place of 4-(2-pyridon-1-yl)phenylamine. MS 516.7 and 518.8 (M+H, Cl pattern).

Example 39

Preparation of N-[4-(2-pyridon-1-yl)phenyl]-2N-(4-chlorophenylaminocarbonyl)-6-hydroxy-1,2,3,4-tetrahydroisoquinoline-3-carboxamide

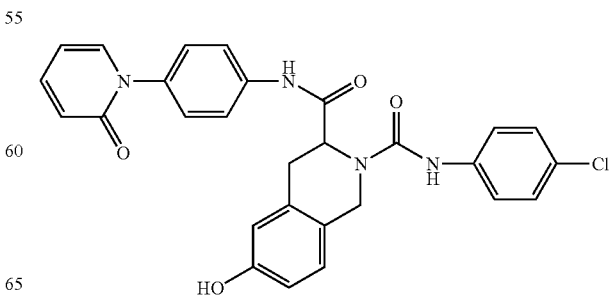

The titled compound was prepared analogously to the procedures described in Example 24, using 4-(2-pyridon-1-yl)phenylamine in the place of 4-(1-Methyl-4,5-dihydro-1H-imidazol-2-yl)-phenylamine. MS 515.2 and 517.3 (M+H, Cl pattern).

Example 40

Preparation of N-[4-(4-methyl-homopiperazinyl)phenyl]-2N-(4-chlorophenylaminocarbonyl)-6-hydroxy-1,2,3,4-tetrahydroisoquinoline-3-carboxamide

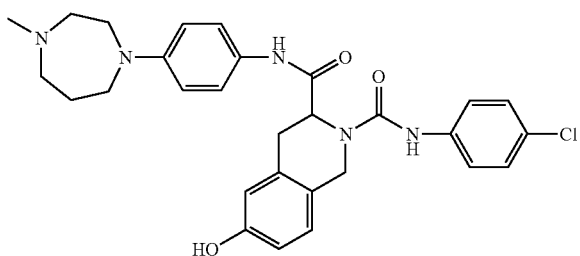

The titled compound was prepared analogously to the procedures described in Example 24, using 4-(4-methyl-homopiperazinyl)phenylamine in the place of 4-(1-Methyl-4,5-dihydro-1H-imidazol-2-yl)-phenylamine. MS 534.2 and 536.2 (M+H, Cl pattern).

Example 41

Preparation of N-[4-(2-thiopyridon-1-yl)phenyl]-2N-(4-chlorophenylaminocarbonyl)-6-hydroxy-1,2,3,4-tetrahydroisoquinoline-3-carboxamide

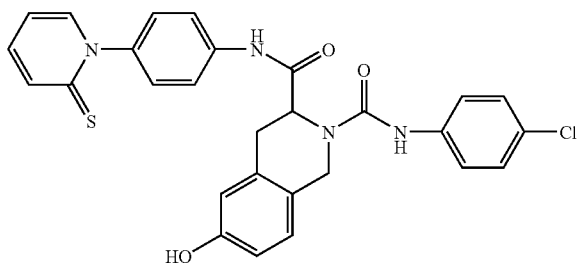

A. Preparation of 1-nitro-4-(2-pyridon-1-yl)benzene

A mixture of 2-hydroxypyridine (337 mg, 3.55 mmol), 1-fluoro-4-nitrobenzene (376 uL, 3.55 mmol) and $Cs_2CO_3$ (1.50 g, 4.60 mmol) in DMF (10 mL) was heated at 120° C. overnight. Water was added to induce precipitation. The precipitate was purified by a silica gel column using 30-100% EtOAc in hexanes as solvents to give the desired product (334 mg). MS 217.3 (M+H).

B. Preparation of 1-nitro-4-(2-thiopyridon-1-yl)benzene

A mixture of 1-nitro-4-(2-pyridon-1-yl)benzene (160 mg, 0.741 mmol), $NaHCO_3$ (622 mg, 7.40 mmol) and $P_2S_5$ (810 mg, 3.65 mmol) in dioxane (8 mL) was heated at 80° C. overnight. The dioxane was removed in vacuo. The residue was partitioned between $H_2O$ and $CH_2Cl_2$. The $CH_2Cl_2$ phase was separated, washed with brine, dried over $Na_2SO_4$, concentrated in vacuo to give a solid (179 mg). MS 233.3 (M+H).

C. Preparation of 4-(2-thiopyridon-1-yl)phenylamine

To a solution of 1-nitro-4-(2-thiopyridon-1-yl)benzene (179 mg, 0.722 mmol) in DMF (5 mL) at 80 C, $SnCl_2$ dihydrate (700 mg, 3.10 mmol) was added. The mixture was stirred at 80° C. for 2 h. The DMF was removed in vacuo. To the residue, MeOH was added. The insoluble was filtered off. The filtrate was purified by a silica gel prep-TLC using $CH_2Cl_2$/MeOH (95/5) as solvents to give the desired product (50 mg). MS 203.2 (M+H).

D. Preparation of N-[4-(2-thiopyridon-1-yl)phenyl]-2N-(4-chlorophenylaminocarbonyl)-6-hydroxy-1,2,3,4-tetrahydroisoquinoline-3-carboxamide The titled compound was prepared analogously to the procedures described in Example 24, using 4-(2-thiopyridon-1-yl)phenylamine in the place of 4-(1-Methyl-4,5-dihydro-1H-imidazol-2-yl)-phenylamine. MS 531.2 and 533.2 (M+H, Cl pattern).

Example 42

Preparation of (3R) 4-(2-piperidinon-1-yl)piperidin-1-yl 2N-(4-chlorophenylaminocarbonyl)-1,2,3,4-tetrahydroisoquinoline-3-carboxamide

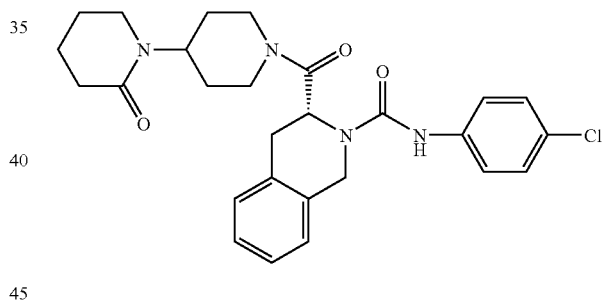

A. Preparation of 4-(2-pyridon-1-yl)pyridine

A mixture of 4-bromopyridine hydrochloride (778 mg, 4.00 mmol), 2-hydroxypyridine (388 mg, 4.08 mmol), $K_3PO_4$ (1.70 g, 8.00 mmol) and 1,2-trans-diaminocyclohexane (200 uL, 1.60 mmol) in dioxane (10 mL) was degassed with Ar before being charged with CuI (152 mg, 0.80 mmol). The mixture in a sealed tube was heated at 110° C. overnight. The mixture was then applied to a silica gel column, which was eluted with $CH_2Cl_2$/MeOH (95/5) to give the desired product (205 mg). MS 173.5 (M+H).

B. Preparation of 4-(2-piperidinon-1-yl)piperidine

A solution of 4-(2-pyridon-1-yl)pyridine (186 mg, 1.08 mmol) and $PtO_2$ (100 mg) in HOAc (8 mL) was hydrogenated under 40 psi on a Parr shaker overnight. The mixture was filtered through Celite. The filtrate was concentrated in vacuo. To the residue, aqueous 1N HCl (3 mL) was added. The solution was then concentrated in vacuo to give the desired product as hydrochloride salt (231 mg). MS 183.5 (M+H).

C. Preparation of (3R) 4-(2-piperidinon-1-yl)piperi-
din-1-yl 2N-(4-chlorophenylaminocarbonyl)-1,2,3,4-
tetrahydroisoquinoline-3-carboxamide To a solution of (3R) 2N-(4-chlorophenylaminocarbonyl)-1,2,3,4-tetrahydroisoquinoline-3-carboxylic acid (50 mg, 0.15 mmol), 4-(2-piperidinon-1-yl) piperidine (20 mg, 0.11 mmol) and triethylamine (30 uL, 0.22 mmol) in DMF (3 mL), BOP (70 mg, 0.16 mmol) was added. The mixture was stirred at room temperature for 30 min. It was then purified by HPLC to give the titled compound (31 mg). MS 495.2 and 497.2 (M+H, Cl pattern).

Example 43

Preparation of (3R) 4-(2-pyridon-1-yl)piperidin-1-yl
2N-(4-chlorophenylaminocarbonyl)-1,2,3,4-tetrahy-
droisoquinoline-3-carboxamide

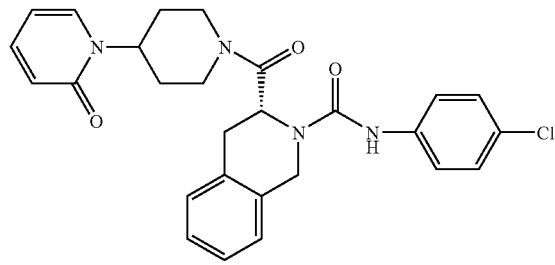

A. Preparation of 4-(2-pyridon-1-yl)piperidine

To a solution of t-butyl 4-hydroxypiperidine carboxylate (1.02 g, 5.07 mmol) in $CH_2Cl_2$ (10 mL) and pyridine (4 mL) at room temperature, methanesulfonyl chloride (1.00 mL, 12.9 mmol) was added. The mixture was stirred at room temperature overnight. Water and $CH_2Cl_2$ were added. The organic phase was separated, washed with 5% $NaHCO_3$, 1N HCl and brine, then it was dried over $Na_2SO_4$, concentrated in vacuo to give a white solid (1.35 g).

A mixture of the white solid (550 mg, 1.97 mmol), 2-hydroxypyridine (207 mg, 2.18 mmol) and $Cs_2CO_3$ (1.37 g, 4.20 mmol) in DMF (10 mL) was heated at 100° C. for 2 h. After being cooled to room temperature, the mixture was filtered. The filtrate was then purified by RP-HPLC to give the desired compound as a minor product (62 mg). MS 223.3 (M−tBu+H) and 279.5 (M+H).

The compound (62 mg) was dissolved in trifluoroacetic acid (6 mL). After being stirred for 30 min, the trifluoroacetic acid was removed in vacuo. The residue was dissolved in $H_2O$ (5 mL), 6N HCl (0.5 mL) was added. The aqueous solution was then lyophilized to give the titled compound as hydrochloride salt (47 mg).

B. Preparation of (3R) 4-(2-pyridon-1-yl)piperidin-
1-yl 2N-(4-chlorophenylaminocarbonyl)-1,2,3,4-
tetrahydroisoquinoline-3-carboxamide The titled compound was prepared analogously to the procedures described in step C of Example 42, using 4-(2-pyridon-1-yl)piperidine in the place of 4-(2-piperidinon-1-yl)piperidine. MS 491.0 and 493.0 (M+H, Cl pattern).

Example 44

Preparation of (3R) 4-(3-morpholinon-4-yl)piperi-
din-1-yl 2N-(4-chlorophenylaminocarbonyl)-1,2,3,4-
tetrahydroisoquinoline-3-carboxamide

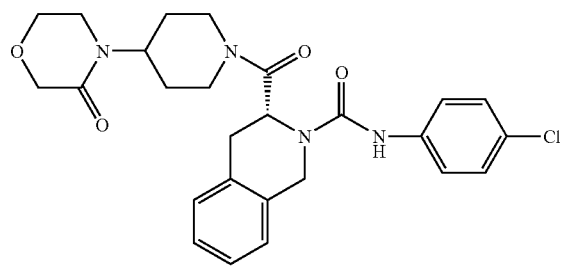

A. Preparation of 4-(3-morpholinon-4-yl)piperidine

A mixture of 4-bromopyridine hydrochloride (778 mg, 4.00 mmol), 3-morpholinone (404 mg, 4.00 mmol), $K_3PO_4$ (1.70 g, 8.00 mmol) and 1,2-trans-diaminocyclohexane (200 uL, 1.60 mmol) in dioxane (10 mL) was degassed with Ar before being charged with CuI (152 mg, 0.80 mmol). The mixture in a sealed tube was heated at 110° C. overnight. The mixture was applied to a silica gel column, which was then eluted with 2-5% MeOH in $CH_2Cl_2$ to give the desired product (85 mg). MS 179.5 (M+H)

A solution of the compound (85 mg, 0.48 mmol) and $PtO_2$ (50 mg) in HOAc (8 mL) was hydrogenated under 40 psi on a Parr shaker overnight. The mixture was filtered through Celite. The filtrate was concentrated in vacuo. To the residue, aqueous 1N HCl (3 mL) was added. The solution was then concentrated in vacuo to give the desired product as hydrochloride salt (91 mg). MS 185.2 (M+H).

B. Preparation of (3R) 4-(3-morpholinon-4-yl)piperi-
din-1-yl 2N-(4-chlorophenylaminocarbonyl)-1,2,3,4-
tetrahydroisoquinoline-3-carboxamide The titled compound was prepared analogously to the procedures described in step C of Example 42, using 4-(3-morpholinon-4-yl)piperidine in the place of 4-(2-piperidinon-1-yl)piperidine.

Example 45

Preparation of (3R) N-[4-(4-methyl-2-piperazinon-1-
yl)phenyl]-2N-(4-chlorophenylaminocarbonyl)-1,2,
3,4-tetrahydroisoquinoline-3-carboxamide

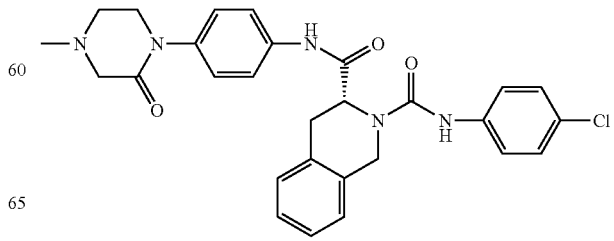

A. Preparation of 4-(4-methyl-2-piperazinon-1-yl)phenylamine

To a mixture of piperazin-2-one (200 mg, 2.00 mmol) and 37% aqueous HCHO (0.300 mL, 4.00 mmol) in dioxane (8 mL) and HOAc (0.100 mL) at room temperature, NaBH$_3$CN (252 mg, 4.00 mmol) was added. After being stirred at room temperature overnight, the mixture was concentrated in vacuo. The residue was partitioned between H$_2$O and n-BuOH. The n-BuOH phase was separated, washed with 5% NaHCO$_3$, then concentrated in vacuo to give the 4-methyl-2-piperazinone (211 mg). MS 115.5 (M+H).

A mixture of 4-methyl-2-piperazinone (200 mg, 1.75 mmol), 4-iodoaniline (384 mg, 1.75 mmol), K$_3$PO$_4$ (848 mg, 4.00 mmol) and 1,2-trans-diaminocyclohexane (98 uL, 0.80 mmol) in dioxane (6 mL) was degassed with Ar before being charged with CuI (76 mg, 0.40 mmol). The mixture in a sealed tube was heated at 110° C. for 4 h. It was then purified by a silica gel prep-TLC using CH2Cl2/MeOH (95/5) as solvents to give the desired product (25 mg). MS 206.2 (M+H).

B. Preparation of (3R) N-[4-(4-methyl-2-piperazinon-1-yl)phenyl]-2N-(4-chlorophenylaminocarbonyl)-1,2,3,4-tetrahydroisoquinoline-3-carboxamide The titled compound was prepared analogously to the procedure described in step C of Example 14, using 4-(4-methyl-2-piperazinon-1-yl)phenylamine in the place of 4-(3-oxo-morpholin-4-yl)phenylamine. MS 518.2 and 520.2 (M+H, Cl pattern).

Example 46

Preparation of (3R) N-[4-(4-methyl-2-homopiperazinon-1-yl)phenyl]-2N-(4-chlorophenylaminocarbonyl)-1,2,3,4-tetrahydroisoquinoline-3-carboxamide

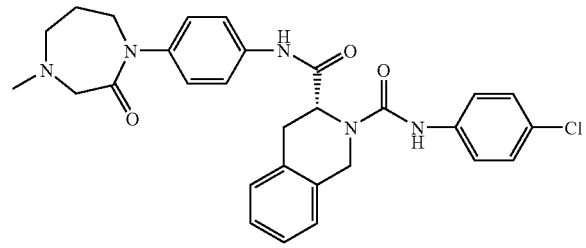

A. Preparation of 4-(4-methyl-2-homopiperazinon-1-yl)phenylamine

To a solution of sarcosine methyl ester hydrochloride (1.00 g, 7.16 mmol) in 5 N NaOH (1.5 mL, 7.50 mmol) and H$_2$O (8 mL), acrylonitrile (0.550 mL, 8.36 mmol) was added. The mixture was heated at 70° C. for 4 h. After being cooled to room temperature, H$_2$O and n-BuOH were added. The n-BuOH phase was separated, washed with 5% NaHCO$_3$, concentrated in vacuo to give an oily residue (443 mg). MS 157.5 (M+H).

A mixture of the oil (443 mg, 2.84 mmol) and PtO2 (152 mg) in HOAc (8 mL) was hydrogenated under balloon H$_2$ for 3 days. The mixture was filtered through celite. The filtrate was concentrated in vacuo. The residue was partitioned between 5% NaHCO$_3$ and EtOAc. However, it was found that the product went to the aqueous phase, and underwent the desired cyclization to give the titled compound, which was then obtained by lyophilizing the aqueous phase to give a powder. The products in the powder were extracted out with MeOH. The MeOH solution was purified by a silica gel prep-TLC using CH$_2$Cl$_2$/MeOH (95/5) as solvents to give the desired 4-methyl-2-homopiperazinone (35 mg). MS 129.5 (M+H).

A mixture of 4-iodoaniline (70 mg, 0.32 mmol), 4-methyl-2-homopiperazinone (35 mg, 0.27 mmol), K$_3$PO$_4$ (135 mg, 0.64 mmol) and 1,2-trans-diaminocyclohexane (16 uL, 0.13 mmol) in dioxane (4 mL) was degassed with Ar before being charged with CuI (18 mg, 0.095 mmol). The mixture in a sealed tube was heated at 110 C overnight. The mixture was then purified by a silica gel prep-TLC using CH$_2$Cl$_2$/MeOH (95/5) as solvents to give the titled compound (9 mg). MS 220.5 (M+H).

B. Preparation of (3R) N-[4-(4-methyl-2-homopiperazinon-1-yl)phenyl]-2N-(4-chlorophenylaminocarbonyl)-1,2,3,4-tetrahydroisoquinoline-3-carboxamide The titled compound was prepared analogously to the procedure described in step C of Example 14, using 4-(4-methyl-2-homopiperazinon-1-yl)phenylamine in the place of 4-(3-oxo-morpholin-4-yl)phenylamine. MS 532.5 and 534.5 (M+H, Cl pattern).

Example 47

Preparation of (3R) N-[4-(2-pyridon-1-yl)phenyl]-2N-(4-fluorophenylaminocarbonyl)-1,2,3,4-tetrahydroisoquinoline-3-carboxamide

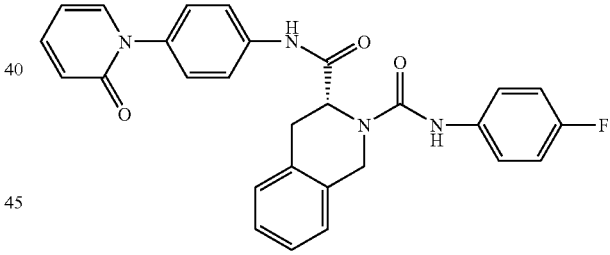

To a solution of D-tetrahydroisoquinoline-3-carboxylic acid hydrochloride (513 mg, 2.40 mmol) in 1N NaOH (10 mL), a solution of Boc$_2$O (0.717 mL, 3.12 mmol) in dioxane (6 mL) was added. After being stirred for 3 h, the mixture was washed with Et$_2$O. The aqueous phase was acidified with 1N HCl to pH 1-2. The product was extracted with EtOAc to give an oily residue (660 mg). MS 276.2 (M-H).

To a solution of the oil (110 mg, 0.40 mmol), 4-(2-pyridon-1-yl)phenylamine (89 mg, 0.48 mmol) and triethylamine (170 uL, 1.22 mmol) in DMF (3 mL), BOP (229 mg, 0.52 mmol) was added. After being stirred at room temperature overnight, H$_2$O and EtOAc were added. The organic phase was separated, washed with 5% NaHCO$_3$, dried over Na$_2$SO$_4$, concentrated in vacuo to give the desired carboxamide. The carboxamide was dissolved in TFA (4 mL). After being stirred for 1 h, TFA was removed in vacuo. The residue was partitioned between EtOAc and 5% NaHCO$_3$. The EtOAc phase was separated, dried over Na$_2$SO$_4$, concentrated in vacuo to give a solid (60 mg).

To a solution of the solid (30 mg, 0.087 mmol) in CH$_3$CN (2 mL), 4-fluorophenylisocyanate (20 uL, 0.178 mmol) was added. After being stirred for 30 min, the mixture was purified by HPLC to give the titled compound (17 mg). MS 483.3 (M+H).

Example 48

Preparation of (3R) N-[4-(2-pyridon-1-yl)phenyl]-2N-[5-(2-chlorothiophene)aminocarbonyl]-1,2,3,4-tetrahydroisoquinoline-3-carboxamide

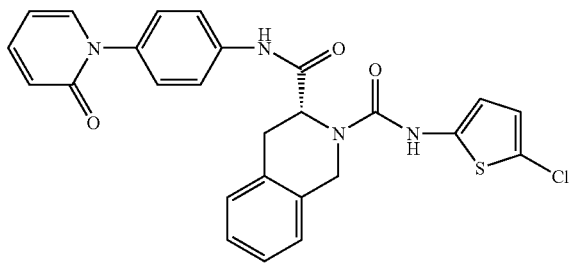

A. Preparation of 2-chlorothiophene-5-isocyanate

To a suspension of 5-chloro-2-thiophenecarboxylic acid (650 mg, 4.00 mmol) in CH$_2$Cl$_2$ (8 mL) containing 3 drops of DMF, oxalyl chloride (0.700 mL, 8.00 mmol) was added. The suspension became clear after 10 min of stirring. After being stirred for 1 h, the mixture was concentrated in vacuo. The residue was dissolved in toluene (8 mL). NaN$_3$ (540 mg, 8.31 mmol) was added. The mixture was stirred at room temperature overnight. It was then filtered. The filtrate was heated at 100° C. for 3 h. The solution was filtered, and used in the next reaction.

B. Preparation of (3R) N-[4-(2-pyridon-1-yl)phenyl]-2N-[5-(2-chlorothiophene)aminocarbonyl]-1,2,3,4-tetrahydroisoquinoline-3-carboxamide The titled compound was prepared analogously to the procedure described in Example 47, using 2-chlorothiophene-5-isocyanate in the place of 4-fluorophenylisocyanate. MS 505.1 and 507.1 (M+H, Cl pattern).

Example 49

Preparation of (3R) N-[4-(4-methyl-homopiperazin-1-yl)phenyl]-2N-[5-(2-chlorothiophene)aminocarbonyl]-1,2,3,4-tetrahydroisoquinoline-3-carboxamide

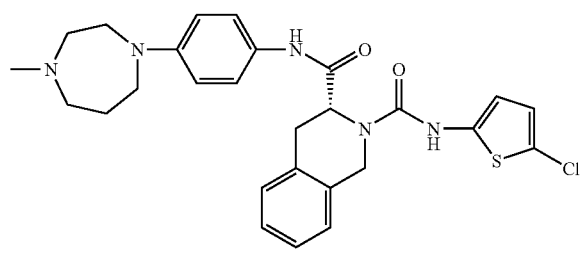

The titled compound was prepared analogously to the procedure described in Example 48, using 4-(4-methyl-homopiperazin-1-yl)phenylamine in the place of 4-(2-pyridon-1-yl)phenylamine. MS 524.2 and 526.2 (M+H, Cl pattern).

Example 50

This example illustrates methods for evaluating the compounds of the invention, along with results obtained for such assays. The in vitro and in vivo Factor Xa isoform activities of the inventive compounds can be determined by various procedures known in the art, such as a test for their ability to inhibit the activity of the Factor Xa isoform. The potent affinities for Factor Xa isoform exhibited by the inventive compounds can be measured by an IC$_{50}$ value (in nM). The IC$_{50}$ value is the concentration (in nM) of the compound required to provide 50% inhibition of Factor Xa isoform. The smaller the IC$_{50}$ value, the more active (potent) is a compound for inhibiting Factor Xa isoform.

An in vitro assay for detecting and measuring inhibition activity against Factor Xa is as follows:

IC$_{50}$ and Ki Determinations:

Substrate:

The substrate S-2765 (Z-D-Arg-Gly-Arg-pNA.HCl) was obtained from Diapharma (West Chester, Ohio).

Enzyme:

The human plasma protein factor Xa was purchased from Haematologic Technologies (Essex Junction, Vt.).

Methods

IC$_{50}$ Determinations

All assays, which are performed in 96-well microtiter plates, measure proteolytic activity of the enzyme (factor Xa) by following cleavage of paranitroanilide substrate. The assay buffer used for proteolytic assays was Tris buffered saline (20 mM Tris, 150 mM NaCl, 5 mM CaCl$_2$, 0.1% Bovine serum albumin (BSA), 5% Dimethly Sulfoxide (DMSO) pH 7.4). In a 96-well microtiter plate, inhibitor was serially diluted to give a range of concentrations from 0.01 nM to 10 μM (final). Duplicate sets of wells were assayed and control wells without inhibitor were included. Enzyme was added to each well, (fXa concentration=1 nM), the plate was shaken for 5 seconds and then incubated for 5 minutes at room temperature. S2765 was added (100 μM final) and the plate was shaken for 5 seconds (final liquid volume in each well was 200 μl). The degree of substrate hydrolysis was measured at 405 nm on a Thermomax plate reader (Molecular Devices, Sunnyvale, Calif.) for 2 minutes. The initial velocities (mOD/min), for each range of inhibitor concentrations, were fitted to a four parameter equation using Softmax data analysis software. The parameter C, derived from the resulting curve-fit, corresponded to the concentration for half maximal inhibition (IC$_{50}$).

K$_i$ Determination

The assay buffer for this series of assays was Hepes buffered saline (20 mM Hepes, 150 mM NaCl, 5 mM CaCl$_2$, 0.1% PEG-8000, pH 7.4). In a 96-well microtiter plate, inhibitor was serially diluted in a duplicate set of wells to give a range of final concentrations from 5 pM to 3 μM final. Controls without inhibitor (8 wells) were included. The enzyme, fXa (1 nM final) was added to the wells. The substrate S-2765 (200 μM final) was added and the degree of substrate hydrolysis was measured at 405 nm on a Thermomax plate reader for 5 minutes, using Softmax software. Initial velocities (mOD/min) were analyzed by non-linear least squares regression in the Plate K$_i$ software (BioKin Ltd, Pullman, Wash.)(Literature reference: Kusmic P, Sideris S, Cregar L M, Elrod K C, Rice K D, Janc J. High-throughput screening of enzyme inhibitors: Automatic determination of tight-binding inhibition constants. *Anal. Biochemistry* 2000, 281:62-67). The model used for fitting the inhibitor dose-response curves was the Morrison equation. An apparent $K_i$ (Ki*) was determined. The overall $K_i$ was calculated using the following equation:

$$Ki = \frac{Ki^*}{1+\frac{[S]}{Km}}$$

where [S] is substrate concentration (200 μM) and $K_m$, the Michaelis constant for S2765.

The hERG (Human Ether-a-go-go Related Gene Protein) Membrane Binding Assay

Human embryonic kidney (HEK293) cells stably transfected with hERG cDNA were used for preparation of membranes (Literature reference: Zhou, Z., Gong, Q., Ye, B., Fan, Z., Makielski, C., Robertson, G., January, C. T., Properties of HERG stably expressed in HEK293 cells studied at physiological temperature. *Biophys. J*, 1998, 74:230-241). The assay buffer was comprised of 50 mM Tris, 10 mM KCl, 1 mM $MgCl_2$, pH 7.4. Competition assays for hERG binding were performed, in a 96 well plate, with 50 μL $^3$H-dofetilide, at a concentration of 3.5 nM (final concentration of 0.01% ethanol). Test compound was added at final concentrations of 100 μM, 33.33 μM, 11.11 μM, 3.70 μM, 1.23 μM, 0.41 μM, 0.14 μM, 0.046 μM, 0.015 μM, and 0.005 μM (1.0% DMSO). Each compound was run in duplicate on each of two plates. Total binding was determined by addition of 50 μL of assay buffer in place of compound. Non-specific binding was determined by addition of 50 μL of 50 μM terfenadine in place of test compound. All assays were initiated by addition of 150 μL of membrane homogenates (15 ug protein/well as final concentration) to the wells (total volume=250 μL per well), and the plates were incubated at room temperature for 80 minutes on a shaking platform. All assays were terminated by vacuum filtration on to glass fiber filters, followed by two washes with cold assay buffer. The filter plates were dried at 55° C. for 90 minutes, after which, Microscint 0 (50 μL) was added to each well of the dried filter plate. The plates were counted on a Packard Topcount (Perkin Elmer, Boston, Mass.) using a one minute protocol. Scintillation reading (counts per minute, CPM) data generated by the Packard TopCount was used to calculate the percent inhibition of $^3$H-dofetilide binding, for each compound at each concentration, using the total binding control value corrected for non-specific binding. The $IC_{50}$ value was calculated from the percent inhibition curve generated using Excel XL Fit software (Microsoft). The equilibrium dissociation constant ($K_i$) was calculated using the equation of Cheng and Prusoff (see "Relationship between the inhibition constant ($K_i$) and the concentration of inhibitor which causes 50 percent inhibition ($I_{50}$) of an enzymatic reaction," *Biochem Pharmacol.*, 1973, 22(23):3099-108.

$$K_i=IC_{50}/[1+([L]/K_D)].$$

A compound can be run through this assay and its corresponding $IC_{50}$ inhibition value can be calculated from the assay data.

The following examples exhibited Factor Xa $IC_{50}$ values less than or equal to 100 nM: 1, 2, 3(S), 3(R), 4, 5, 8, 10, 11, 13, 14, 15, 16, 17, 18, 19, 20, 24, 25, 26, 27, 28, 29, and 31, 33, 35, 36, 37, 38, 39, 40, 41, 42, 43, 44, 46, 47, 48 and 49.

The following examples exhibited Factor Xa $IC_{50}$ values greater than 100 nM and less than 500 nM: 9, 22, 30, 32, 34 and 45.

The following examples exhibited Factor Xa $IC_{50}$ values greater than or equal to 500 nM: 6, 7, 12, 21 and 23.

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

What is claimed is:

1. A compound having the formula:

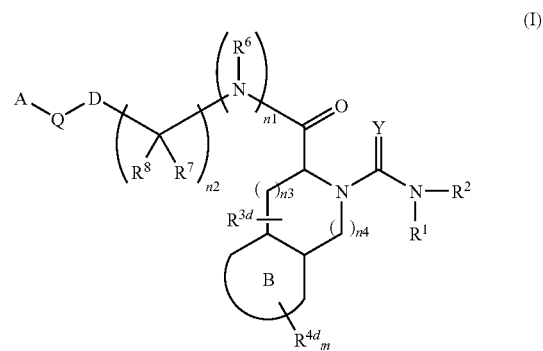

(I)

wherein:

Y is O or S;

B is a 5-7 membered aryl or heteroaryl comprising 1 to 3 heteroatoms selected from the group consisting of N, O, and S, each aryl or heteroaryl optionally substituted with 1 to 3 $R^{4d}$ substiuents;

$R^1$ is a member selected from the group consisting of: hydrogen, —$C_{1-6}$alkyl, —$C_{0-6}$alkyl-aryl, heteroaryl and —$C_{2-6}$alkenyl;

$R^2$ is a member selected from the group consisting of: thienyl and phenyl, optionally substituted with from 1 to 3 $R^{2a}$ substituents, wherein each heterocyclyl comprises 5 to 12 ring atoms, 1 to 4 of which are members independently selected from the group consisting of N, O and S, wherein, if $R^2$ is phenyl a $R^{2a}$ is attached to the phenyl ring at a position para to the rest of the molecule;

A-Q-D-$(CR^7R^8)_{n2}$—$NR^6{}_{n1}$ is selected from the group consisting of:

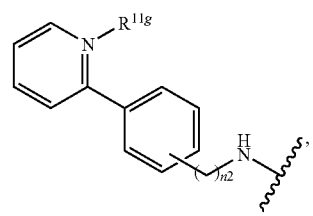

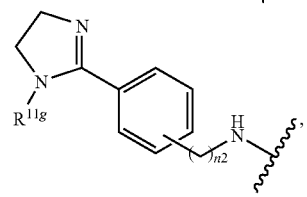

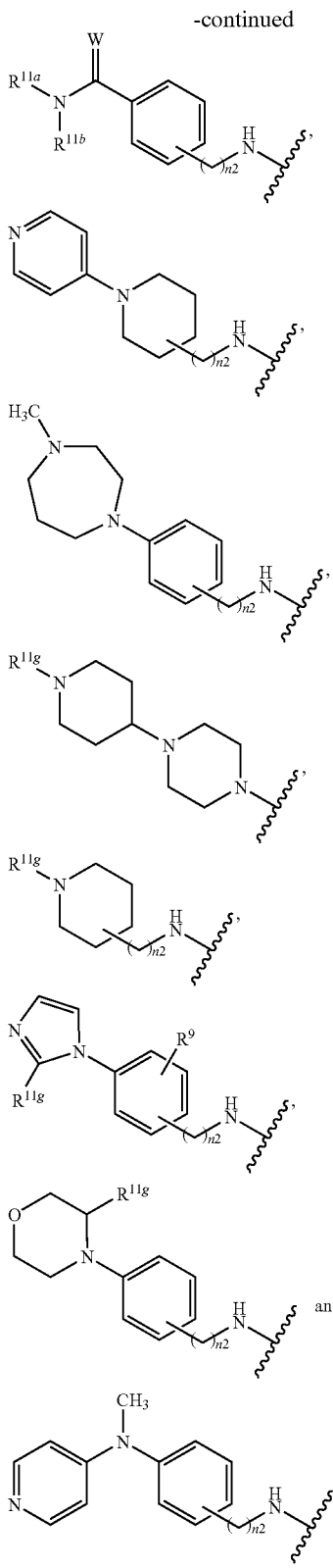

wherein W is O, S or NH; each dashed line independently indicates a single or double bond; and the wavy line indicates the point of attachment to the rest of the molecule;

each $R^{3d}$, $R^{4d}$ and $R^{11g}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —O—$CH_2$—$CO_2R^{12a}$, —N($R^{12a}$)—$CH_2$—$CH_2$—$OR^{12b}$, —$C_{0-2}$alkyl-C(O)$NR^{12a}R^{12b}$, —$C_{0-2}$alkyl-$C_{0-2}R^{12a}$, —($CH_2$)$_m$N($R^{12a}$)—C(O)$R^{12b}$, —$C_{0-2}$alkyl-N($R^{12c}$)—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-N($R^{12d}$)C(=$NR^{12c}$)$NR^{12a}R^{12b}$, —$C_{0-2}$alkyl-N($R^{12a}$)—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CONR^{12a}R^{12b}$, =O, =S, —OH, —CN and —$NO_2$; wherein each heteroaryl or heterocyclyl comprises 1 to 4 heteroatoms, independently selected from the group consisting of N, O and S, $R^{2a}$ is a member independently selected from the group consisting of: H, halo, $C_{1-6}$alkyl, $C_{2-6}$alkenyl, $C_{2-6}$alkynyl, $C_{0-4}$alkyl $C_{3-8}$cycloalkyl, —$C_{0-2}$alkyl-$CF_3$, —$C_{0-2}$alkyl-CN, —$C_{0-2}$alkyl-$NO_2$, $C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —O—$CH_2$—$CO_2R^{12a}$, —N($R^{12a}$)—$CH_2$—$CH_2$—$OR^{12b}$, —$C_{0-2}$alkyl-C(O)$NR^{12a}R^{12b}$, —$C_{0-2}$alkyl-$C_{0-2}R^{12a}$, —($CH_2$)$_m$N($R^{12a}$)—C(O)$R^{12b}$, —$C_{0-2}$alkyl-N($R^{12c}$)—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-N($R^{12d}$)C(=$NR^{12c}$)$NR^{12a}R^{12b}$, —$C_{0-2}$alkyl-N($R^{12a}$)—$SO_2R^{12b}$, =O, =S, $NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, —$C_{1-6}$alkyl, —$C_{2-6}$alkenyl, —$C_{2-6}$alkynyl, —$C_{0-4}$alkyl-$C_{3-8}$cycloalkyl, —$C_{1-4}$alkoxy, $CO_2H$, —$CO_2C_{1-4}$alkyl, $CONR^{12a}R^{12b}$, =O, =S, —OH, —CN, and $NO_2$; wherein each heteroaryl or heterocyclyl comprises 1 to 4 heteroatoms, independently selected from the group consisting of N, O and S, each $R^{11a}$, $R^{11b}$, $R^{12a}$, $R^{12b}$, $R^{12c}$, and $R^{12d}$, are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-COC$_{1-4}$alkyl, —$C_{0-6}$alkyl-$SO_{0-2}$—$C_{1-4}$alkyl, —$C_{0-6}$alkyl-$SO_2$—N($C_{1-4}$alkyl, $C_{1-4}$alkyl), —$C_{0-6}$alkyl-N($C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2$H, —$CO_2C_{1-4}$alkyl, —CON($C_{1-4}$alkyl, $C_{1-4}$alkyl), =O, =S, —OH, —CN and $NO_2$;

$R^6$ is selected from the group consisting of: hydrogen, $C_{1-6}$alkyl, $C_{2-6}$alkenyl, $C_{2-6}$alkynyl and $C_{0-4}$alkyl $C_{3-8}$cycloalkyl, —$C_{0-6}$alkyl-aryl and —$C_{0-6}$alkyl-heteraryl;

each subscript n1 and n2 is an integer of 0 to 1;

each subscript n3 and n4 is an integer of 0 to 2;

the subscript m is an integer of 0 to 3; and pharmaceutically acceptable salts thereof.

2. A compound having the formula:

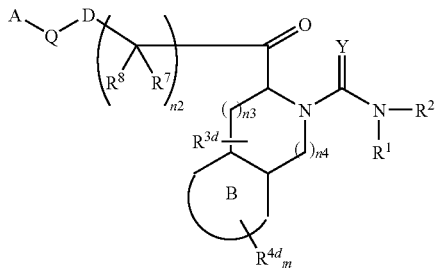

wherein:

Y is O or S;

B is a 5-7 membered aryl or heteroaryl comprising 1 to 3 heteroatoms selected from the group consisting of N, O, and S, each aryl or heteroaryl optionally substituted with 1 to 3 $R^{4d}$ substituents;

$R^1$ is a member selected from the group consisting of: hydrogen, —$C_{1-6}$alkyl, —$C_{0-6}$alkyl-aryl, heteroaryl and —$C_{2-6}$alkenyl;

$R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substiuents, wherein each heterocyclyl comprises 5 to 12 ring atoms, 1 to 4 of which are members independently selected from the group consisting of N, O and S;

A-Q-D-$(CR^7R^8)_{n2}$—$NR^6_{n1}$ is selected from the group consisting of:

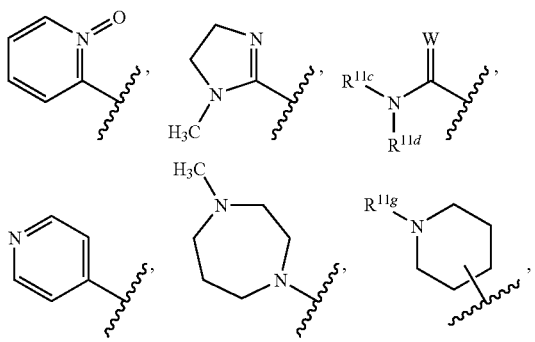

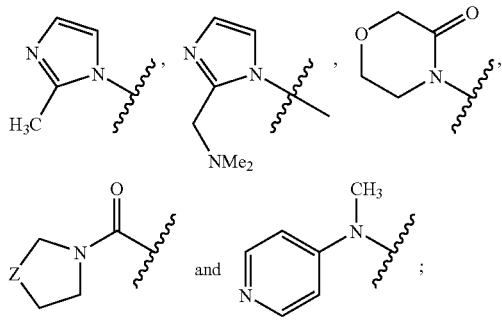

wherein W is O, S or NH; each dashed line independently indicates a single or double bond; and the wavy line indicates the point of attachment to the rest of the molecule;

each $R^{2a}$, $R^{3d}$, $R^{4d}$ and $R^{11g}$ member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —$C_{0-2}$$CH_2$—$CO_2R^{12a}$, —N($R^{12a}$)—$CH_2$—$CH_2$—$OR^{12b}$, —$C_{0-2}$alkyl-C(O)$NR^{12a}R^{12b}$, —$C_{0-2}$alkyl-$CO_2R^{12a}$, —$(CH_2)_mN(R^{12a})$—C(O)$R^{12b}$, —$C_{0-2}$alkyl-$N(R^{12c})$—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-$N(R^{12d})$C(=$NR^{12c}$)$NR^{12a}R^{12b}$, —$C_{0-2}$alkyl-N$(R^{12a})$—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$C_{0-2}$H, —$CO_2C_{1-4}$alkyl, —$CONR^{12a}R^{12b}$, =O, =S, —OH, —CN and —$NO_2$,; wherein each heteroaryl or heterocyclyl comprises 1 to 4 heteroatoms, independently selected from the group consisting of N, O and S, each $R^{11a}$, $R^{11b}$, $R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$SO_2$-$C_{1-4}$alkyl, —$C_{0-6}$alkyl-$SO_2$—N($C_{1-4}$alkyl, $C_{1-4}$alkyl), —$C_{0-6}$alkyl-N($C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2$H, —$CO_2C_{1-4}$alkyl, —CON($C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, =S, —OH, —CN and $NO_2$;

the subscript n2 is an integer of 0 to 1;

each subscript n3 and n4 is an integer of 0 to 2;

the subscript m is an integer of 0 to 3; and pharmaceutically acceptable salts thereof.

3. A compound having the formula:

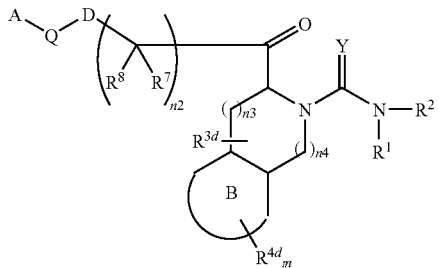

wherein:

Y is O or S;

B is a 5-7 membered aryl or heteroaryl comprising 1 to 3 heteroatoms selected from the group consisting of N, O, and S, each aryl or heteroaryl optionally substituted with 1 to 3 $R^{4d}$ substiuents;

$R^1$ is a member selected from the group consisting of: hydrogen, —$C_{1-6}$alkyl, —$C_{0-6}$alkyl-aryl, heteroaryl and —$C_{2-6}$alkenyl;

$R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S;

A-Q-D-$(CR^7R^8)_{n2}$—$NR^6_{n1}$ is selected from the group consisting of:

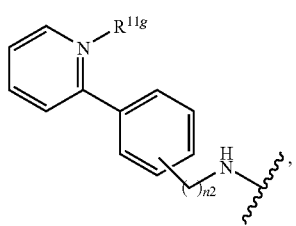

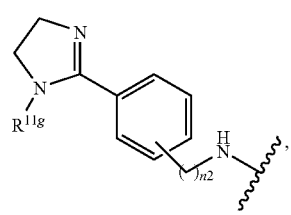

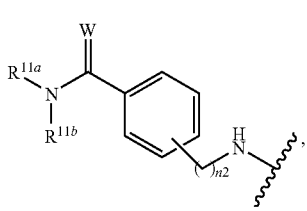

-continued

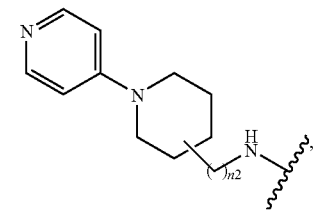

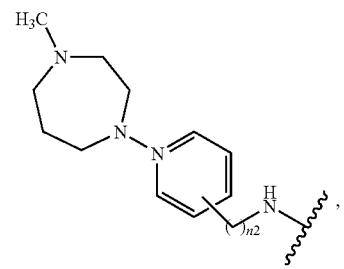

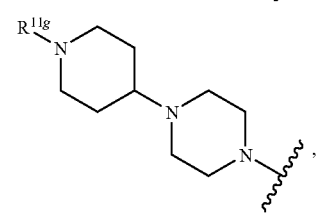

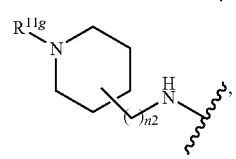

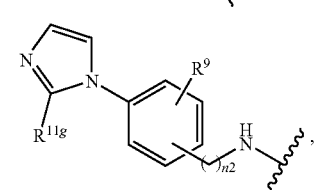

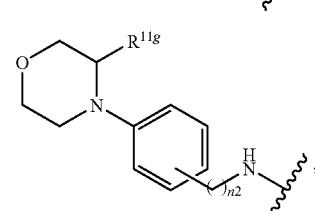

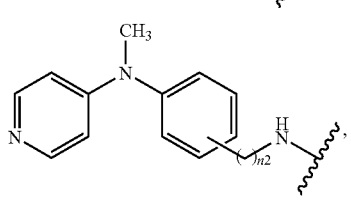

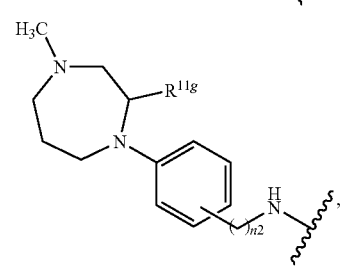

-continued

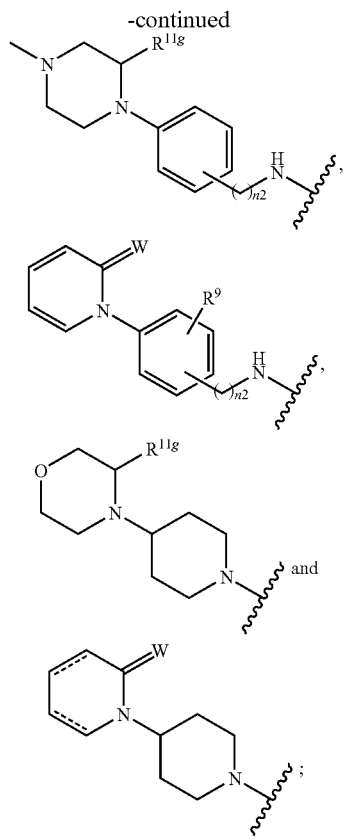

wherein W is O, S or NH; each dashed line independently indicates a sinizle or double bond; and the wavy line indicates the point of attachment to the rest of the molecule;

each $R^{2a}$, $R^{3d}$, $R^{4d}$ and $R^{11g}$ member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —O—$C_{0-2}$alkyl-$CF_3$, —$C_{0-2}$alkyl-$CF_3$, —$C_{0-2}$alkyl-CN, —$C_{0-2}$alkyl-$NR^{12a}R^{12b}$, —$C_{0-2}$alkly-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$-$OR^{12a}$, —O—$CH_2$—$CO_2R^{12a}$, —$N(R^{12a})$—$CH_2$—$CH_2$—$OR^{12b}$, —$C_{0-2}$alkyl-$C(O)NR^{12a}R^{12b}$, —$C_{0-2}$alkyl-$CO_2R^{12a}$, —(C$H_2$)$_m$$N(R^{12a})$—$C(O)R^{12b}$, —$C_{0-2}$alkyl-$N(R^{12c})$—$C(O)NR^{12a}R^{12b}$, —$C_{0-2}$alkyl-$C(=NR^{12c})NR^{12a}R^{12b}$, —$C_{0-2}$alkyl-$C(=NR^{12a})R^{12b}$, —$C_{0-2}$alkyl-$N(R^{12d})C(=NR^{12c})NR^{12a}R^{12b}$, —$C_{0-2}$alkyl-$N(R^{12a})$—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$C_{0-2}H$, —$CO_2C_{1-4}$alkyl, —$CONR^{12a}R^{12b}$, =O, =S, —OH, —CN and —$NO_2$,; wherein each heteroaryl or heterocyclyl comprises 1 to 4 heteroatoms, independently selected from the group consisting of N, O and S;

each $R^{11a}$, $R^{11b}$, $R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-SO—$C_{1-4}$alkyl, —$C_{0-6}$alkyl-$SO_2$—$N(C_{1-4}$alkyl, $C_{1-4}$alkyl), —$C_{0-6}$alkyl-N(C$_{1-4}$alkvl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_1$alkyl), —OH, —CN and $NO_2$,; or can be taken together with the nitrogen atom to which they are attached to form a 3-8 membered heterocyclyl group, comprising 1 to 4 heteroatoms selected from the group consisting of N, O and 5, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), =O, =S, —OH, —CN and $NO_2$;

$R^6$ is selected from the group consisting of: hydrogen, $C_{1-6}$alkyl, $C_{2-6}$alkenyl, $C_{2-6}$alkynyl and $C_{0-4}$alkyl $C_{3-8}$cycloalkyl, —$C_{0-6}$alkyl-aryl and —$C_{0-6}$alkyl-heteroaryl;

the subscript ni is an integer of 0 to 1;

each subscript n3 and n4 is an integer of 0 to 2;

the subscript m is an integer of 0 to 3; and pharmaceutically acceptable salts thereof.

4. A compound having the formula:

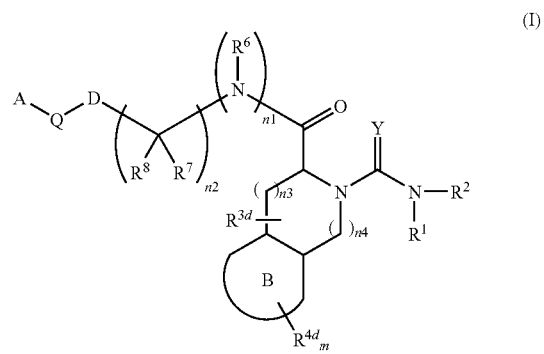

(I)

wherein:

Y is O or S;

B is a 5-7 membered aryl or heteroaryl comprising 1 to 3 heteroatoms selected from the group consisting of N, O, and S, each aryl or heteroaryl optionally substituted with 1 to 3 $R^{4d}$substiuents;

$R^1$ is a member selected from the group consisting of: hydrogen, —$C_{1-6}$alkyl, —$C_{0-6}$alkyl-aryl, heteroaryl and —$C_{2-6}$alkenyl;

$R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S;

A-Q-D-$(CR^7R^8)_{n2}$—$NR^6_{n1}$ is selected from the group consisting of:

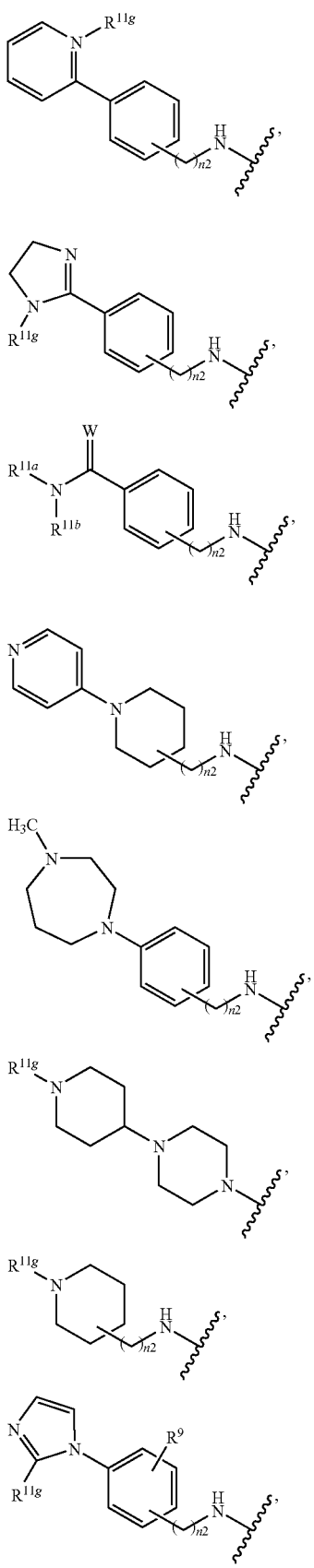

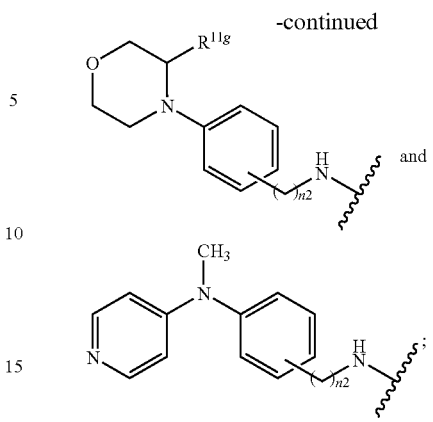

wherein W is O, S or NH; each dashed line independently indicates a single or double bond; and the wavy line indicates the point of attachment to the rest of the molecule;

each $R^{2a}$, $R^{3d}$ and $R^{4d}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$SR^{12a}$, —O—$CH_2$—$CH_2$—$OR^{12a}$, —O—$CH_2$—$CO_2R^{12a}$, —N($R^{12a}$)—$CH_2$—$CH_2$—$OR^{12b}$, —$C_{0-2}$alkyl-C(O)$NR^{12a}R^{12b}$, —$C_{0-2}$alkyl-$CO_2R^{12a}$, —$(CH_2)_mN(R^{12a})$—C(O)$R^{12b}$, —$C_{0-2}$alkyl-N($R^{12c}$)—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-N($R^{12d}$)C(=$NR^{12c}$)$NR^{12a}R^{12b}$, —$C_{0-2}$alkyl-N($R^{12a}$)—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, $CONR^{12a}R^{12b}$, =O, =S, —OH, —CN and —$NO_2$; wherein each heteroaryl or heterocyclyl comprises 1 to 4 heteroatoms, independently selected from the group consisting of N, O and S, each $R^{11g}$ is independently selected from the group consisting of $C_{1-6}$alkyl, —$C_{0-2}$alkyl-$NR^{12a}R^{12b}$ and =O;

each $R^{11a}$, $R^{11b}$, $R^{12a}$, $R^{12b}$, $R^{12c}$, and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$SO_2$—$C_{1-4}$alkyl, —$C_{0-6}$alkyl-$SO_2$—N($C_{1-4}$alkyl, $C_{1-4}$alkyl), —$C_{0-6}$alkyl-N($C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$;

$R^6$ is selected from the group consisting of: hydrogen, $C_{1-6}$alkyl, $C_{2-6}$alkenyl, $C_{2-6}$alkynyl and $C_{0-4}$alkyl $C_{3-8}$cycloalkyl, —$C_{0-6}$alkyl-aryl and —$C_{0-6}$alkyl-heteroaryl;

each subscript n1 and n2 is an integer of 0 to 1;
each subscript n3 and n4 is an integer of 0 to 2;
the subscript m is an integer of 0 to 3; and
pharmaceutically acceptable salts thereof.

5. A compound of any one of claims 1, 2, 3 and 4, wherein A-Q- is selected from the group consisting of:

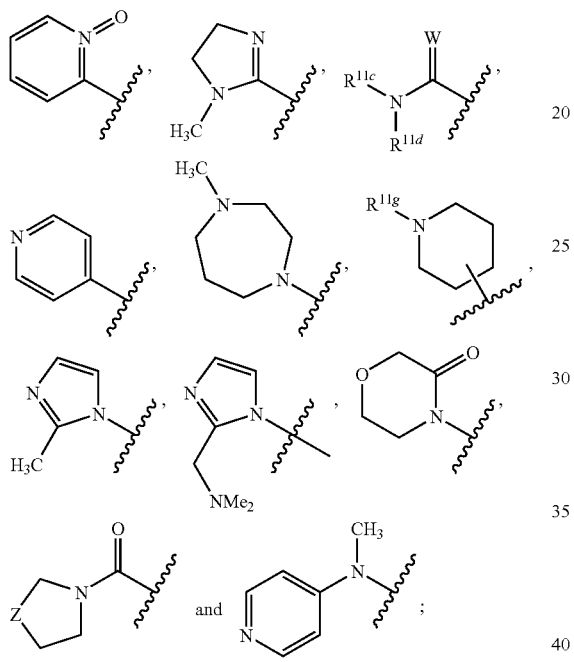

wherein W is O, S or NH;
Z is O, S, or NH; and
the wavy line indicates the point of attachment to the rest of the molecule.

6. A compound of having the formula:

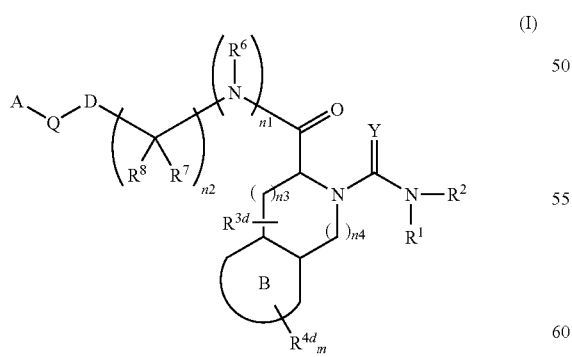

(I)

wherein:
Y is O or S;
B is a 5-7 membered aryl or heteroaryl comprising 1 to 3 heteroatoms selected from the group consisting of N, O, and S, each aryl or heteroaryl optionally substituted with 1 to 3 $R^{4d}$ substituents;

$R^1$ is a member selected from the group consisting of: hydrogen, —$C_{1-6}$alkyl, —$C_{0-6}$alkyl-aryl, heteroaryl and —$C_{2-6}$alkenyl;

$R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S;

A-Q-D-$(CR^7R^8)_{n2}$—$NR^6_{n1}$ is selected from the group consisting of:

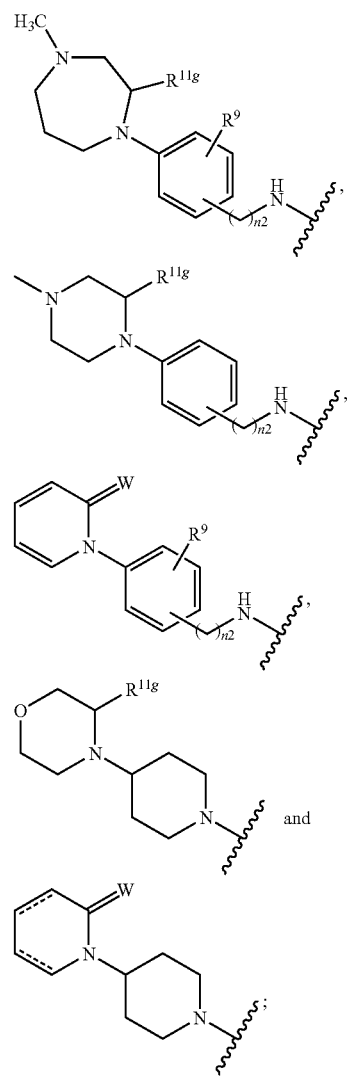

wherein W is O, S or NH; and
the wavy line indicates the point of attachment to the rest of the molecule; and each dashed line independently indicates a single or double bond;

each $R^{2a}$, $R^{3d}$, $R^{4d}$ and $R^{11g}$ member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —C$_{0-2}$alkly-SO$_2$NR$^{12a}$R$^{12b}$, —C$_{0-2}$alkyl-SO$_2$R$^{12a}$, —C$_{0-2}$alkyl-SOR$^{12a}$, —C$_{0-2}$alkyl-CF$_3$, —C$_{0-2}$alkyl-OR$^{12a}$, —C$_{0-2}$alkyl-SR$^{12a}$, —O—CH$_2$—CH$_2$-OR$^{12a}$, —O—CH$_2$—CO$_2$R$^{12a}$, —N(R$^{12a}$)—CH$_2$—CH$_2$—OR$^{12b}$, —C$_{0-2}$alkyl-C(O)NR$^{12a}$R$^{12b}$, —C$_{0-2}$alkyl-CO$_2$R$^{12a}$, —(CH$_2$)$_m$N(R$^{12a}$)—C(O)R$^{12b}$, —C$_{0-2}$alkyl-N(R$^{12c}$)—C(O)NR$^{12a}$R$^{12b}$, —C$_{0-2}$alkyl-C(=NR$^{12c}$)NR$^{12a}$R$^{12b}$, —C$_{0-2}$alkyl-C(=NR$^{12a}$)R$^{12b}$, —C$_{0-2}$alkyl-N(R$^{12d}$)C(=NR$^{12c}$)NR$^{12a}$R$^{12b}$, —C$_{0-2}$alkyl-N(R$^{12a}$)—SO$_2$—R$^{12b}$, =O, =S, =NR$^{12a}$, 5- or 6-membered aryl, 5- or 6-membered heteroaryl and 5- to 7-membered heterocyclyl, each of which is optionally substituted with a member independently selected from the group consisting of halo, CF$_3$, OCF$_3$, SCF$_3$, C$_{1-6}$alkyl, C$_{2-6}$alkenyl, C$_{2-6}$alkynyl, C$_{0-4}$alkylC$_{3-8}$cycloalkyl, C$_{1-4}$alkoxy, —CO$_2$H, —CO$_2$C$_{1-4}$alkyl, —CONR$^{12a}$R$^{12b}$, =O, =S, —OH, —CN and —NO$_2$; wherein each heteroaryl or heterocyclyl comprises 1 to 4 heteroatoms, independently selected from the group consisting of N, O and S, each R$^{11a}$, R$^{11b}$, R$^{12a}$, R$^{12b}$, R$^{12c}$ and R$^{12d}$ are members independently selected from the group consisting of: H, C$_{1-6}$alkyl, C$_{2-6}$alkenyl, C$_{2-6}$alkynyl, C$_{0-4}$alkylC$_{3-8}$cycloalkyl, C$_{0-4}$alkylaryl, C$_{0-4}$alkyl-heteroaryl, —C$_{0-6}$alkyl-COC$_{1-4}$alkyl, —C$_{0-6}$alkyl-SO$_2$-C$_{1-4}$alkyl, —C$_{0-6}$alkyl-SO$_2$—N(C$_{1-4}$alkyl, C$_{1-4}$alkyl), —C$_{0-6}$alkyl-N(C$_{1-4}$alkyl, C$_{1-4}$alkyl) and —C$_{1-6}$alkyl-O—C$_{0-6}$alkyl, wherein 1-3 hydrogen atoms on the aryl or heteroaryl ring may be independently replaced with a member selected from the group consisting of halo, C$_{1-6}$alkyl, C$_{2-6}$alkenyl, C$_{2-6}$alkynyl, C$_{0-4}$alkylC$_{3-8}$cycloalkyl, C$_{1-4}$alkoxy, —CO$_2$H, —CO$_2$C$_{1-4}$alkyl, —CON(C$_{1-4}$alkyl, C$_{1-4}$alkyl), —OH, —CN and NO$_2$; or can be taken together with the nitrogen atom to which they are attached to form a 3-8 membered heterocyclyl group, comprising 1 to 4 heteroatoms selected from the group consisting of N, O and S, optionally substituted with 1 to 4 R$^{13}$ substituents selected from the group consisting of halo, C$_{1-6}$alkyl, C$_{2-6}$alkenyl, C$_{2-6}$alkynyl, C$_{0-4}$alkyl C$_{3-8}$cycloalkyl, C$_{1-4}$alkoxy, —CO$_2$H, —CO$_2$C$_{1-4}$alkyl, —CON(C$_{1-4}$alkyl, C$_{1-4}$alkyl), =O, =S, —OH, —CN and NO$_2$;

R$^6$ is selected from the group consisting of: hydrogen, C$_{1-6}$alkyl, C$_{2-6}$alkenyl, C$_{2-6}$alkynyl and C$_{0-4}$alkyl C$_{3-8}$cycloalkyl, —C$_{0-6}$alkyl-aryl and —C$_{0-6}$alkyl-heteraryl;

each subscript n1 and n2 is an integer of 0 to 1;
each subscript n3 and n4 is an integer of 0 to 2;
the subscript m is an integer of 0 to 3; and
pharmaceutically acceptable salts thereof.

7. A compound selected from the group consisting of: N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide; N-[4-(1N-oxo-pyridin-2-yl)phenyl]-2N-(4-chlorophenylaminocarbonyl)-1,2,3,4-tetrahydroisoquinoline-3-carboxamide; (3S)-N-[4-(1-methyl-4,5-dihydro-1H-imidazol-2-yl)phenyl]-2N-(4-chlorophenylaminocarbonyl)-1,2,3,4-tetrahydroisoquinoline-3-carboxamide; N-[4-(pyrrolidinylimino)phenyl]-2N-(4-chlorophenylaminocarbonyl)-1,2,3,4-tetrahydroisoquinoline-3-carboxamide; N-[4-(dimethylaminoimino)phenyl]-2N-(4-chlorophenylaminocarbonyl)-1,2,3,4-tetrahydroisoquinoline-3-carboxamide; N-[3-(dimethylaminoimino)benzyl]-2N-(4-chlorophenylaminocarbonyl)-1,2,3,4-tetrahydroisoquinoline-3-carboxamide, and N-[3-(1-methyl-4,5-dihydro-1H-imidazol-2-yl)benzyl]-2N-(4-chlorophenylaminocarbonyl)-1,2,3,4-tetrahydroisoquinoline-3-carboxamide; N-[4-(pyrrolidinylcarbonyl)phenyl]-2N-(4-chlorophenylaminocarbonyl)-1,2,3,4-tetrahydroisoquinoline-3-carboxamide; N-[1-(pyridin-4-yl)piperidin-4-yl]methyl-2N-(4-chlorophenylaminocarbonyl)-1,2,3,4-tetrahydroisoquinoline-3-carboxamide; N-[4 (4methyl-homopiperazinyl)]phenyl-2N-(4-chlorophenylaminocarbonyl)-1,2,3,4-tetrahydroisoquinoline-3-carboxamide; 4-(1-methylpiperidin-4-yl)piperazinyl 2N-(4-chlorophenylaminocarbonyl)-1,2,3,4-tetrahydroisoquinoline-3-carboxamide; N-(1isopropylpiperidin 4-yl) 2N-(4-chlorophenylaminocarbonyl)-1,2,3,4-tetrahydroisoquinoline-3-carboxamide; N-[4-(2-dimethylaminomethyl-imidazol-1-yl)-2-fluorophenyl]-2N-(4-chlorophenylaminocarbonyl)-1,2,3,4-tetrahydroisoquinoline-3-carboxamide; N-[4-(3-oxo-morpholin-4-yl)phenyl]-2N-(4-chlorophenylaminocarbonyl)-1,2,3,4-tetrahydroisoquinoline-3-carboxamide; N-[4-(3thiazolidinylcarbonyl)phenyl]-2N-(4-chlorophenylaminocarbonyl)-1,2,3,4-tetrahydroisoquinoline-3-carboxamide; N-[4-(3-oxazolidinylcarbonyl)phenyl]-2N-(4-chlorophenylaminocarbonyl)-1,2,3,4-tetrahydroisoquinoline-3-carboxamide; N-[4-(N-methyl-N-pyridin-4-yl-amino)phenyl]-2N-(4-chlorophenylaminocarbonyl)-1,2,3,4-tetrahydroisoquinoline-3-carboxamide; N-[4-(1-methyl-4,5-dihydro-1H-imidazol-2-yl)phenyl]-2N-(4-chlorophenylaminocarbonyl)-5-methyl-1,2,3,4-tetrahydroisoquinoline-3-carboxamide; N-[4-(pyrrolidinylimino)phenyl]-2N-(4-chlorophenylaminocarbonyl)-5-methyl-1,2,3,4-tetrahydroisoquinoline-3-carboxamide; N-[4-(dimethylaminoimino)phenyl]-2N-(4-chlorophenylaminocarbonyl)-5-methyl-1,2,3,4-tetrahydroisoquinoline-3-carboxamide; (3S)-N-[4-(1-methyl-4,5-dihydro-1H-imidazol-2-yl)phenyl]-2N-(4-chlorophenylaminocarbonyl)-6,7-dimethoxy-1,2,3,4-tetrahydroisoquinoline-3-carboxamide; (3S)-N-[4-(pyrrolidinylimino)phenyl]-2N-(4-chlorophenylaminocarbonyl)-6,7-dimethoxy-1,2,3,4-tetrahydroisoquinoline-3-carboxamide; (3S)-N-[4-(dimethylaminoimino)phenyl]-2N-(4-chlorophenylaminocarbonyl)-6,7-diemthoxy-1,2,3,4-tetrahydroisoquinoline-3-carboxamide; N-[4-(1-methyl-4,5-dihydro-1H-imidazol-2-yl)phenyl]-2N-(4-chlorophenylaminocarbonyl)-6-hydroxy-1,2,3,4-tetrahydroisoquinoline-3-carboxamide; N-[4-(1-methyl-4,5-dihydro-1H-imidazol-2-yl)phenyl]-5N-(4-chlorophenylaminocarbonyl)-4,5,6,7-tetrahydro-thieno [3,2-c]pyridine-6-carboxamide; N-[4-(dimethylaminoimino)phenyl]-5N-(4-chlorophenylaminocarbonyl)-4,5,6,7-tetrahydro-thieno [3,2-c]pyridine-6-carboxamide; N-[4-(4-methyl-homopiperazinyl)]phenyl-5N-(4-chlorophenylaminocarbony)-4,5,6,7-tetrahydro-thieno[3,2-c]pyridine-6-carboxamide; N-[4-(4-methyl-4,5-dihydro-1H-imidazol-2-yl)phenyl]-2N-(4-chlorophenylaminocarbonyl)-2,3-dihydro-1H-isoindole-1-carboxamide; N-[4-(1 N-oxopyridin-2-yl)phenyl]-2N-(4-chlorophenylaminocarbonyl)-2,3-dihydro-1H-isoindole-1-carboxamide; N-[4-(4-methyl-homopiperazinyl)phenyl]-2N-(4-chlorophenylaminocarbonyl)-2,3-dihydro-1H-isoindole-1-carboxamide; N-[4-(3-oxo-morpholin-4yl)phenyl]-2N-(4-chlorophenylaminocarbonyl)-2,3-dihydro-1H-isoindole-1- carboxamide; N-[4-(1N-oxo-pyridin-2-yl)phenyl]-1N-(4-chlorophenylaminocarbonyl)-indoline-2-carboxamide; (3S) N-[4-(4-methyl-homopiperazinyl)]phenyl-2N-(4-chlorophenylaminocarbonyl)-1,2,3,4-tetrahydroisoquinoline-3-carboxamide; (3R) N-[4-(4-methyl-homopiperazinyl)-2-fluorophenyl]-2N-(4-chlorophenylaminocarbonyl)-1,2,3,4-tetrahydroisoquinoline-3-carboxamide; (3R) N-[4-(2-pyridon-1-yl)phenyl]-2N-(4-chlorophenylaminocarbonyl)-1,2,3,4-tetrahydroisoquinoline-3-carboxamide; (3S) N-[4-(2-pyridon-1-yl)phenyl]-2N-(4-chlorophenylaminocarbonyl)-1,2,3,4-tetrahydroisoquinoline-3-carboxamide; (3R) N-[4-(2-pyridon-1-yl)-2-fluorophenyl]-2N-(4-chlorophenylaminocarbonyl)-1,2,3,4-tetrahydroisoquinoline-3-carboxamide; N-[4-(2-pyridon-1-yl)phenyl]-2N-(4-chlorophenylaminocarbonyl)-6-hydroxy-1,2,3,4-tetrahydroisoquinoline-3-carboxamide; N-[4-(4-methyl-homopiperazinyl)phenyl]-2N-(4-chlorophenylaminocarbonyl)-6-hydroxy-1,2,3,4-tetrahydroisoquinoline-3-carboxamide; N-[4-(2-thiopyridon-1-yl)phenyl]-2N-(4-chlorophenylaminocarbonyl)-6-hydroxy-1,2,3,4-tetrahydroisoquinoline-3-carboxamide; (3R)4-(2-piperidinon-1-yl)piperidin-1-yl 2N-(4-chlorophenylaminocarbonyl)-1,2,3,4-tetrahydroisoquinoline-3-carboxamide; (3R) 4-(2-pyridon-1-yl)piperidin-1-yl 2N-(4-chlorophenylaminocarbonyl)-1,2,3,4-tetrahydroisoquinoline-3-carboxamide; (3R) 4-(3-morpholinon-4-yl)piperidin-1-yl 2N-(4-chlorophenylaminocarbonyl)-1,2,3,4-tetrahydroisoquinoline-3-carboxamide; (3R) N-[4-(4-methyl-2-piperazinon-1-yl)phenyl]-2N-(4-chlorophenylaminocarbonyl)-1,2,3,4-tetrahydroisoquinoline-3-carboxamide; (3R) N-[4-(4-methyl-2-homopiperazinon-1-yl)phenyl]-2N-(4-chlorophenylaminocarbonyl)-1,2,3,4-tetrahydroisoquinoline-3-carboxamide; (3R) N-[4-(2-pyridon-1-yl)phenyl]-2N-(4-fluorophenylaminocarbonyl)-1,2,3,4-tetrahydroisoquinoline-3-carboxamide; (3R) N-[4-(2-pyridon-1-yl)phenyl]-2N-[5-(2-chlorothiophene)aminocarbonyl]-1,2,3,4-tetrahydroisoquinoline-3-carboxamide; and (3R) N-[4-(4-methyl-homopiperazin-1-yl)phenyl]-2N-[5-(2-chlorothiophene)aminocarbonyl]-1,2,3,4-tetrahydroisoquinoline-3-carboxamide.

8. A composition comprising a pharmaceutically acceptable excipient and a compound of claim 1.

9. A compound of any one of claims 1, 2, 3, 4 and 6, wherein $R^1$ is H.

10. A compound of any one of claims 1, 2, 3, 4 and 6, wherein the optional substituent $R^{2a}$ is halo.

11. A compound of any one of claims 1, 2, 3, 4 and 6, wherein the moiety

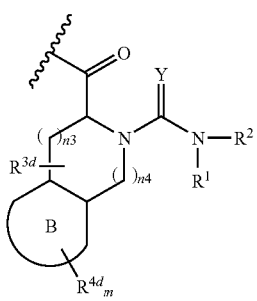

is selected from the group consisting of:

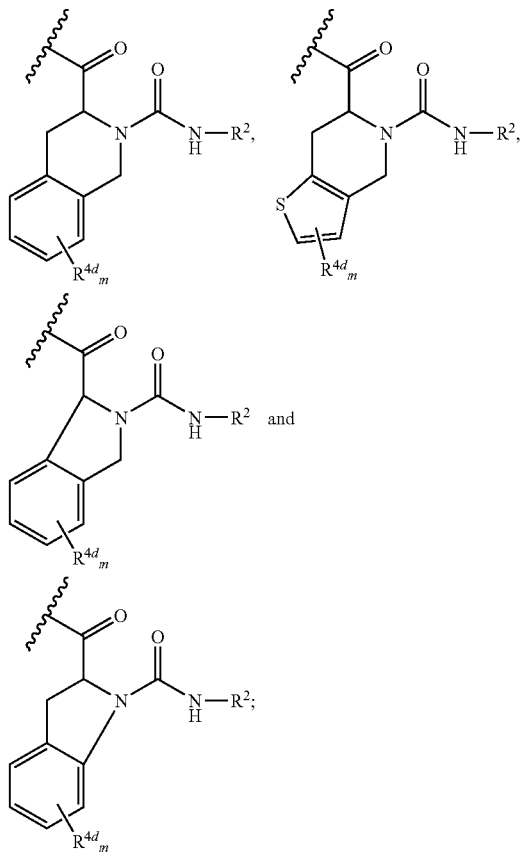

wherein the subscript m is an integer of 0 to 3.

12. A compound of any one of claims 1, 2, 3, 4 and 6, wherein the moiety

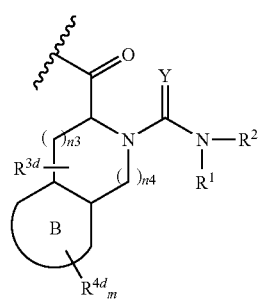

is selected from the group consisting of:

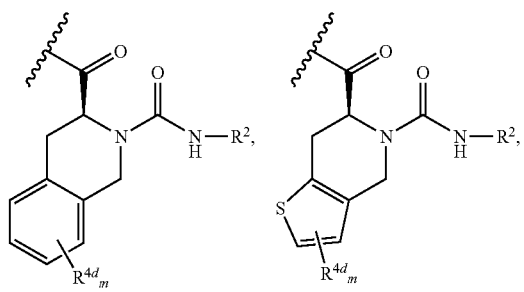

-continued
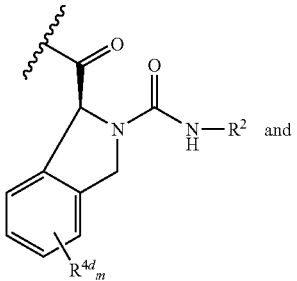
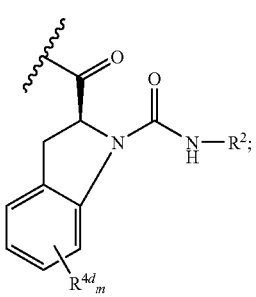
wherein the subscript m is an integer of 0 to 3.
13. A compound of any one of claims 1, 2, 3, 4 and 6, wherein the moiety
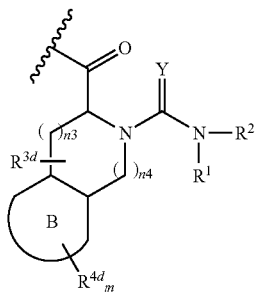
is selected from the group consisting of:
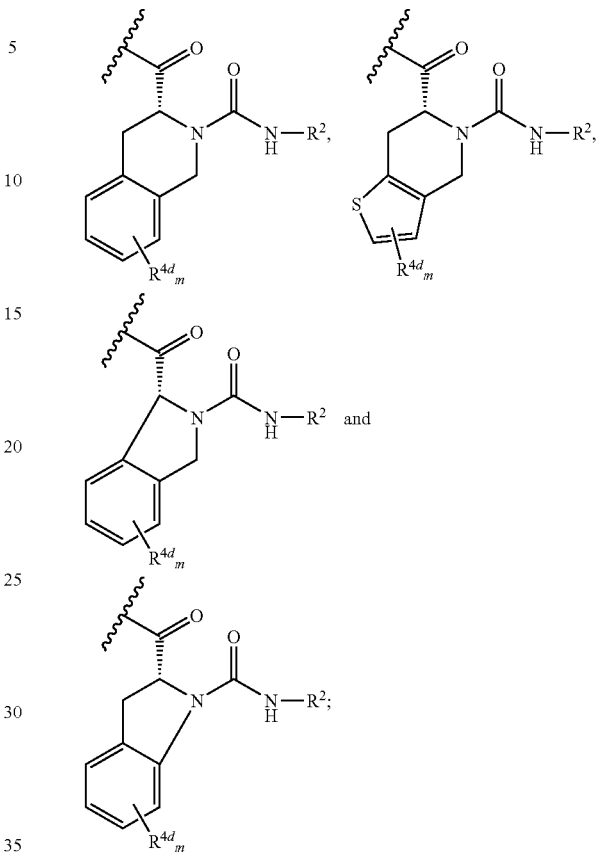
wherein the subscript m is an integer of 0 to 3.
14. A compound of any one of claims 1, 3, 4 and 6, wherein n1 is 1.
15. A compound of any one of claims 1, 3, 4 and 6, wherein $R^6$ is H.
16. A compound of any one of claims 1, 2, 4 and 6, wherein n2 is 0.
* * * * *

UNITED STATES PATENT AND TRADEMARK OFFICE
CERTIFICATE OF CORRECTION

PATENT NO.         : 7,612,089 B2                                           Page 1 of 1
APPLICATION NO.    : 11/284805
DATED              : November 3, 2009
INVENTOR(S)        : Song et al.

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (316) days Delete the phrase "by 316 days" and insert -- by 663 days --

Signed and Sealed this

Twentieth Day of April, 2010

David J. Kappos
*Director of the United States Patent and Trademark Office*